US012201752B2

(12) United States Patent
Dang et al.

(10) Patent No.: US 12,201,752 B2
(45) Date of Patent: Jan. 21, 2025

(54) MEDICATION INFUSION COMPONENTS AND SYSTEMS

(71) Applicant: Medtronic MiniMed, Inc., Northridge, CA (US)

(72) Inventors: Kiem H. Dang, Thousand Oaks, CA (US); Sarnath Chattaraj, Simi Valley, CA (US); Hsi C. Fusselman, Simi Valley, CA (US); Lance P. Hoffman, West Hollywood, CA (US); Guangping Zhang, Calabasas, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 336 days.

(21) Appl. No.: 17/499,612

(22) Filed: Oct. 12, 2021

(65) Prior Publication Data
US 2022/0031941 A1 Feb. 3, 2022

Related U.S. Application Data

(62) Division of application No. 15/874,757, filed on Jan. 18, 2018, now Pat. No. 11,197,949.
(Continued)

(51) Int. Cl.
*A61L 29/14* (2006.01)
*A61K 9/00* (2006.01)
(Continued)

(52) U.S. Cl.
CPC .......... *A61L 29/146* (2013.01); *A61K 9/0019* (2013.01); *A61K 31/727* (2013.01);
(Continued)

(58) Field of Classification Search
CPC .... A61L 29/146; A61L 29/049; A61M 39/10; A61M 5/142; A61M 39/162;
(Continued)

(56) References Cited

U.S. PATENT DOCUMENTS 3,003,500 A 10/1961 Barton et al.
3,631,654 A 1/1972 Riely et al.
(Continued)

FOREIGN PATENT DOCUMENTS

CN 1583188 A 2/2005
CN 1795932 7/2006
(Continued)

OTHER PUBLICATIONS

PCT International Search Report & Written Opinion dated May 22, 2018, International Application No. PCT/US2018/014526.

*Primary Examiner* — Lauren P Farrar
(74) *Attorney, Agent, or Firm* — Fortem IP LLP

(57) ABSTRACT

This invention pertains to systems and components useful for infusing medications such as insulin. Typically, the components are used to deliver insulin to a diabetic patient at a site of infusion over a period of time greater than 4 days. The system components typically comprise a cannula adapted for subcutaneous insertion into a diabetic patient. The system further comprises a fluid conduit adapted to deliver the insulin solution from a medication reservoir to the site of infusion and a depot in operable contact with the fluid conduit. The depot comprises selected materials including a site-loss mitigating agent (such as heparin) which inhibits inflammation at the site of infusion, and encapsulation of the cannula at the site of infusion. The site-loss mitigating agent is not premixed with the insulin, and instead is adapted to contact the insulin solution in the depot as the insulin solution flows from the medication reservoir to the site of infusion.

11 Claims, 57 Drawing Sheets

Related U.S. Application Data

(60) Provisional application No. 62/448,306, filed on Jan. 19, 2017.

(51) Int. Cl.

| | | |
|---|---|---|
| *A61K 31/727* | (2006.01) | |
| *A61K 38/28* | (2006.01) | |
| *A61L 29/04* | (2006.01) | |
| *A61M 5/142* | (2006.01) | |
| *A61M 5/158* | (2006.01) | |
| *A61M 5/38* | (2006.01) | |
| *A61M 25/00* | (2006.01) | |
| *A61M 39/10* | (2006.01) | |
| *A61M 39/16* | (2006.01) | |

(52) U.S. Cl.
CPC ............ *A61K 38/28* (2013.01); *A61L 29/049* (2013.01); *A61M 5/142* (2013.01); *A61M 5/14248* (2013.01); *A61M 5/14276* (2013.01); *A61M 5/38* (2013.01); *A61M 25/005* (2013.01); *A61M 39/10* (2013.01); *A61M 39/162* (2013.01); *A61M 5/158* (2013.01); *A61M 2005/1586* (2013.01); *A61M 2025/0059* (2013.01); *A61M 2205/0272* (2013.01); *A61M 2205/3334* (2013.01); *A61M 2205/584* (2013.01); *A61M 2205/7545* (2013.01); *A61M 2207/00* (2013.01); *A61M 2230/201* (2013.01)

(58) Field of Classification Search
CPC .......... A61M 5/14276; A61M 5/14248; A61M 5/38; A61M 2205/7545; A61M 5/158; A61M 2205/584; A61M 2205/0272; A61M 2005/1586; A61M 2207/00; A61M 2205/3334; A61M 2230/201; A61K 38/28; A61K 31/727; A61K 9/0019
See application file for complete search history.

(56) References Cited

U.S. PATENT DOCUMENTS

| | | |
|---|---|---|
| 3,650,093 A | 3/1972 | Rosenberg |
| 3,827,562 A | 8/1974 | Esmond |
| 3,882,026 A | 5/1975 | McPhee |
| 3,978,857 A | 9/1976 | McPhee |
| 4,004,587 A | 1/1977 | Jess |
| 4,013,072 A | 3/1977 | Jess |
| 4,116,646 A | 9/1978 | Edwards |
| 4,190,426 A | 2/1980 | Ruschke |
| 4,459,139 A | 7/1984 | Vonreis et al. |
| 4,562,751 A | 1/1986 | Nason et al. |
| 4,571,244 A | 2/1986 | Knighton |
| 4,678,408 A | 7/1987 | Nason et al. |
| 4,685,903 A | 8/1987 | Cable et al. |
| 4,755,173 A | 7/1988 | Konopka et al. |
| 4,804,360 A | 2/1989 | Kamen |
| 5,080,653 A | 1/1992 | Voss et al. |
| 5,097,122 A | 3/1992 | Colman et al. |
| 5,183,472 A | 2/1993 | Jaehrling et al. |
| 5,195,986 A | 3/1993 | Kamen |
| 5,308,333 A | 5/1994 | Skakoon |
| 5,391,250 A | 2/1995 | Cheney, II et al. |
| 5,485,408 A | 1/1996 | Blomquist |
| 5,505,709 A | 4/1996 | Funderburk et al. |
| 5,522,769 A | 6/1996 | Deguiseppi |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,902,281 A | 5/1999 | Kraus et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,376,211 B1 | 4/2002 | Little et al. |
| 6,379,301 B1 | 4/2002 | Worthington et al. |
| 6,471,689 B1 * | 10/2002 | Joseph ................ A61M 5/1723 424/424 |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |

(56) References Cited

U.S. PATENT DOCUMENTS

| | | |
|---|---|---|
| 9,901,514 B2 | 2/2018 | Kavazov |
| 10,279,126 B2 | 5/2019 | Chattaraj et al. |
| 11,090,446 B2 | 8/2021 | Chattaraj et al. |
| 11,197,949 B2 | 12/2021 | Dang et al. |
| 11,786,673 B2 | 10/2023 | Chattaraj et al. |
| 2002/0077598 A1 | 6/2002 | Yap et al. |
| 2002/0173748 A1 | 11/2002 | McConnell et al. |
| 2003/0032945 A1 | 2/2003 | Jayaraman |
| 2003/0044555 A1* | 3/2003 | Ding .................. B32B 25/16 525/247 |
| 2003/0100563 A1* | 5/2003 | Edmondson ......... A61K 38/28 514/249 |
| 2005/0161042 A1 | 7/2005 | Fudge et al. |
| 2006/0229530 A1 | 10/2006 | Hosoda et al. |
| 2006/0246272 A1 | 11/2006 | Zhang et al. |
| 2007/0123819 A1 | 5/2007 | Mernoe et al. |
| 2007/0125374 A1 | 6/2007 | Smith et al. |
| 2008/0097407 A1 | 4/2008 | Plishka |
| 2008/0105618 A1 | 5/2008 | Beckius et al. |
| 2010/0160861 A1 | 6/2010 | Causey, III et al. |
| 2010/0234824 A1 | 9/2010 | Christoph et al. |
| 2011/0184382 A1 | 7/2011 | Cady |
| 2013/0303987 A1 | 11/2013 | Esnouf |
| 2015/0112302 A1* | 4/2015 | Chattaraj ............... A61P 43/00 604/257 |
| 2016/0095987 A1 | 4/2016 | Chattaraj et al. |
| 2016/0339226 A1 | 11/2016 | Sealfon |
| 2017/0143950 A1 | 5/2017 | Koch et al. |
| 2021/0338943 A1 | 11/2021 | Chattaraj et al. |
| 2022/0409777 A1 | 12/2022 | Dang et al. |
| 2023/0108058 A1 | 4/2023 | Dang et al. |
| 2024/0001046 A1 | 1/2024 | Chattaraj et al. |

FOREIGN PATENT DOCUMENTS

| | | |
|---|---|---|
| CN | 201969126 U | 9/2011 |
| CN | 103100131 A | 5/2013 |
| CN | 103418053 A | 12/2013 |
| CN | 105848693 A | 8/2016 |
| EP | 2229970 A1 | 9/2010 |
| EP | 3570932 A1 | 11/2019 |
| WO | 2012033847 | 3/2012 |
| WO | 2015061493 | 4/2015 |
| WO | 2016057093 | 4/2016 |
| WO | 2018136799 A1 | 7/2018 |

\* cited by examiner (A) In-line Chamber (B) In-line Plug

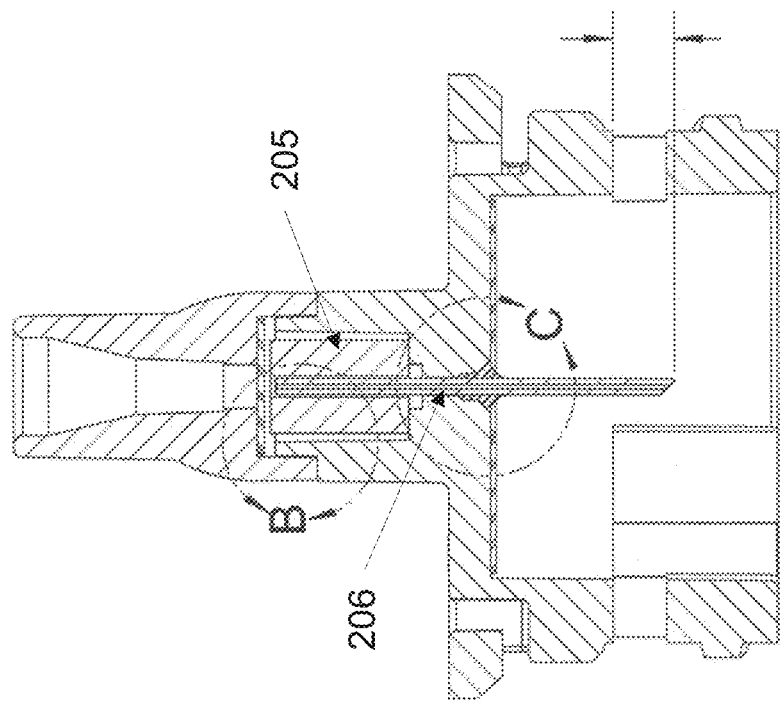
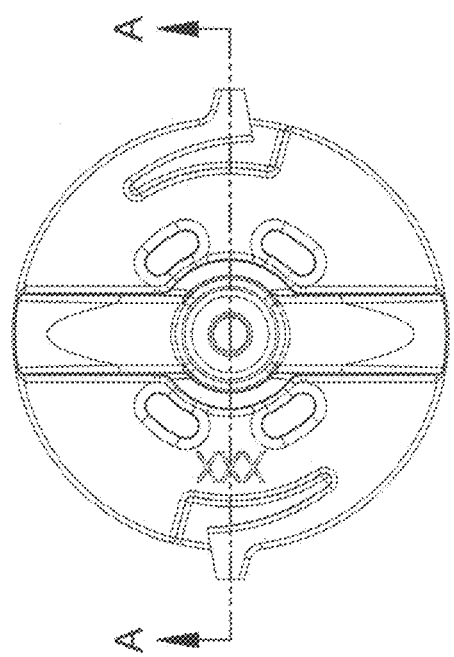
FIG. 28B
FIG. 28A

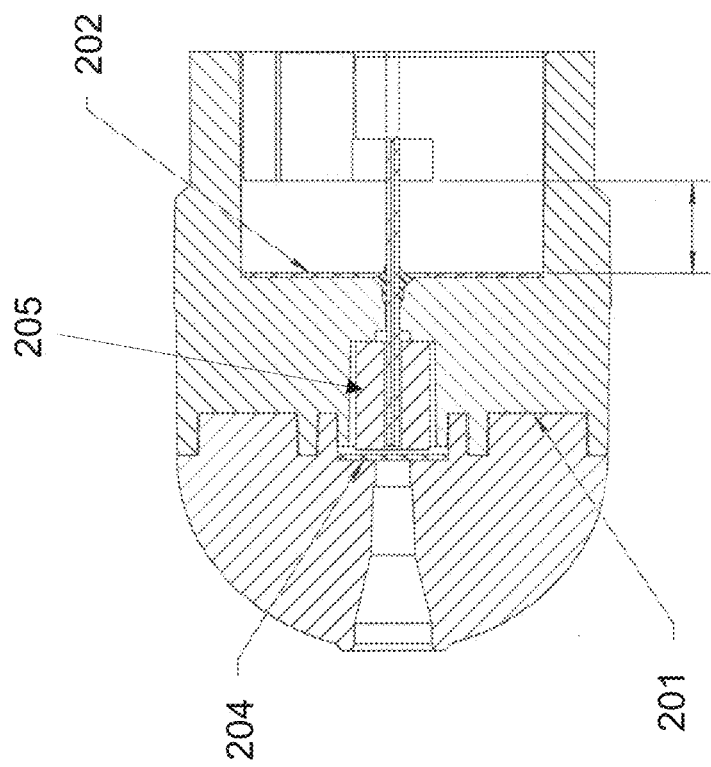
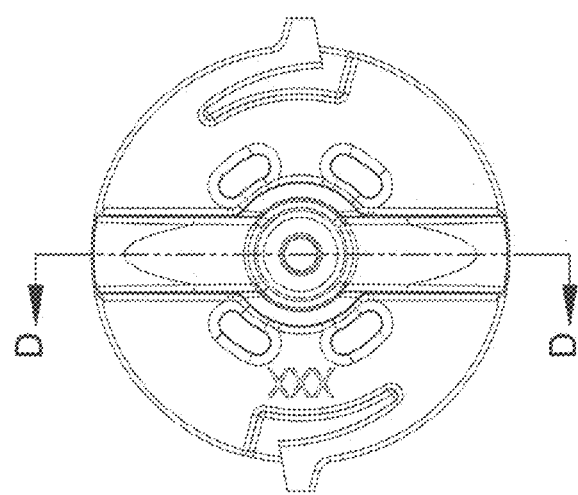
FIG. 29B
FIG. 29A

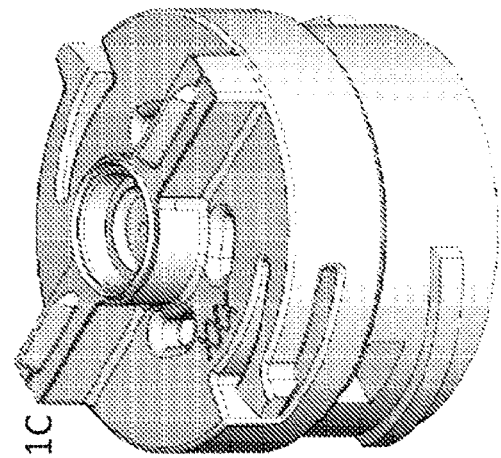
FIG. 31A
FIG. 31B
FIG. 31C
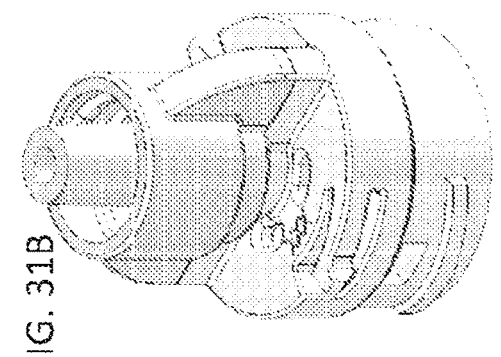
FIG. 31D
Luer connection, Exploded view
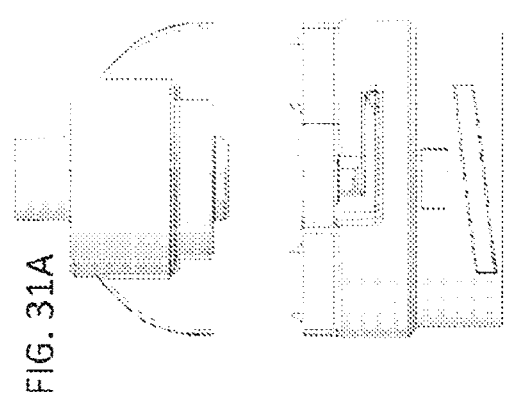
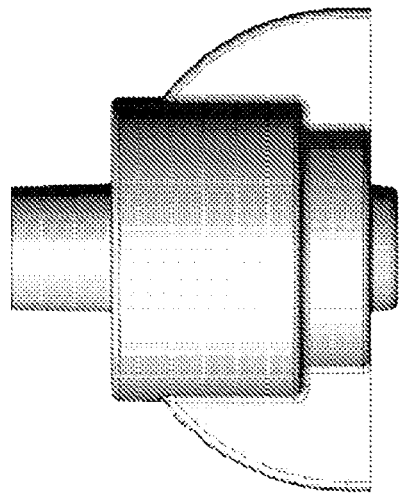
FIG. 31F
Luer Body
Luer Top
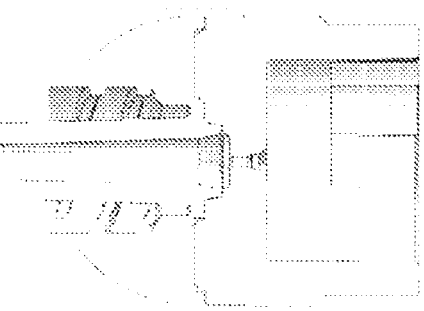
FIG. 31E
Luer
Luer Section View
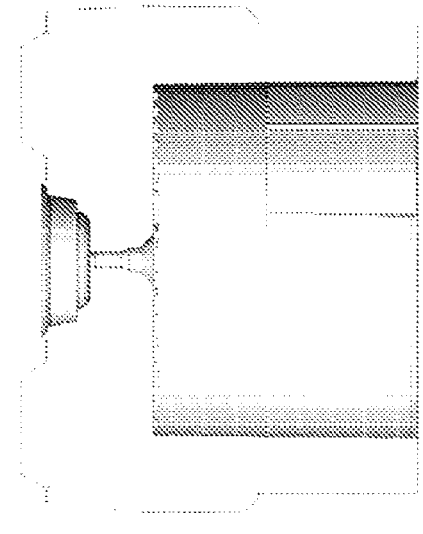
Luer Body Section

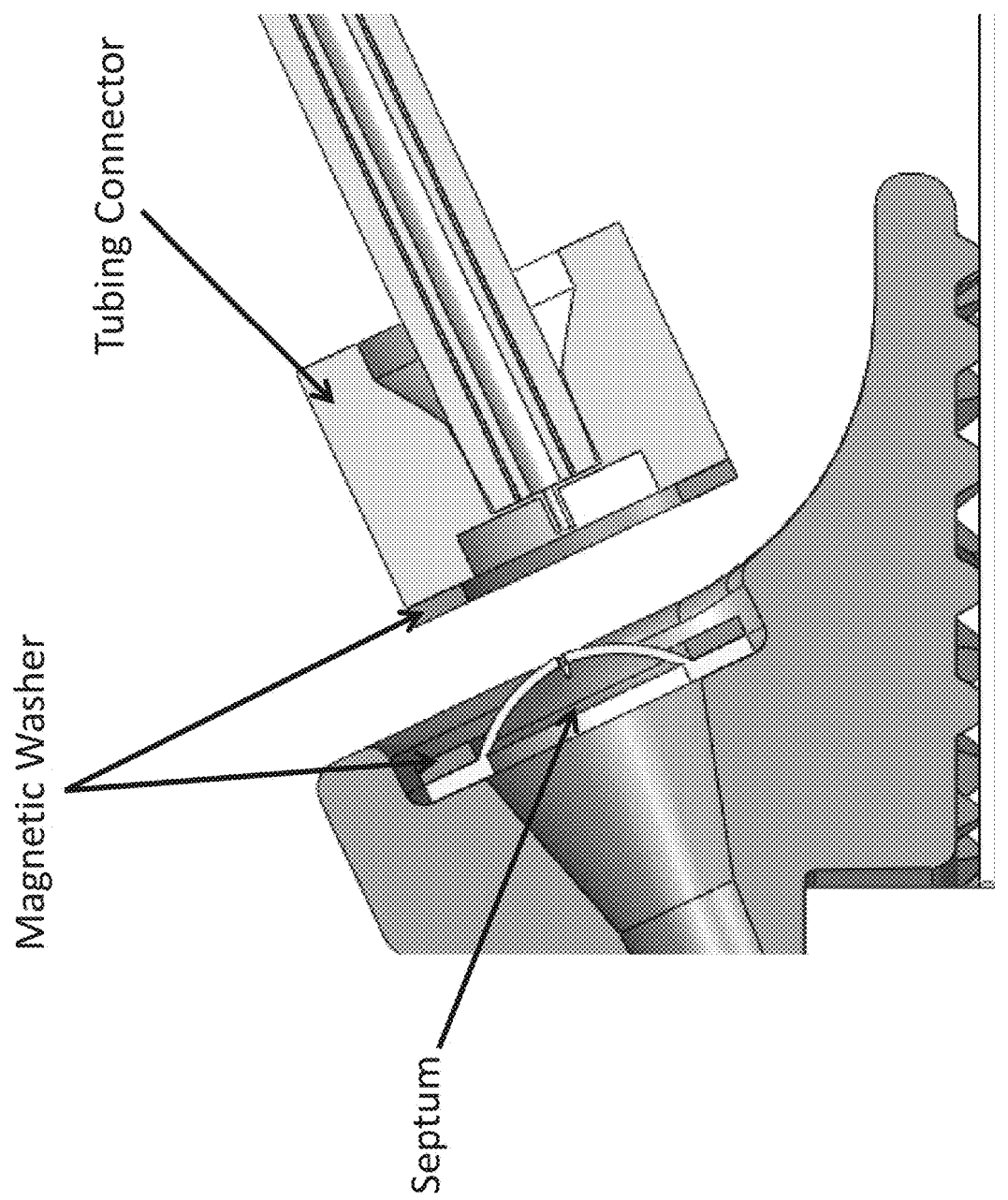

Septum

Tubing Connector

MEDICATION INFUSION COMPONENTS AND SYSTEMS

CROSS-REFERENCE TO RELATED APPLICATIONS

This application is a divisional application which claims the benefit under 35 U.S.C. § 120 and § 121 of U.S. patent application Ser. No. 15/874,757, filed Jan. 18, 2018, which claims priority under Section 120 from U.S. Patent Application Ser. No. 62/448,306, filed Jan. 19, 2017, titled "MEDICATION INFUSION COMPONENTS AND SYSTEMS", the contents of which are incorporated herein by reference.

This application is related to U.S. patent application Ser. No. 14/512,788, filed Oct. 13, 2014, by Chattaraj et al., entitled "Methods and Systems for Inhibiting Foreign-Body Responses in Diabetic Patients," which claims priority under 35 U.S.C. § 119(e) from U.S. Provisional Application Ser. No. 61/894,088, filed on Oct. 22, 2013, by Chattaraj et al., entitled "Methods and Systems for Inhibiting Foreign-Body Responses in Diabetic Patients," U.S. Provisional Application Ser. No. 61/935,010, filed on Feb. 3, 2014, by Chattaraj et al., entitled "Methods and Systems for Inhibiting Foreign-Body Responses in Diabetic Patients," and U.S. Provisional Application Ser. No. 62/032,101, filed on Aug. 1, 2014, by Chattaraj et al., entitled "Methods and Systems for Inhibiting Foreign-Body Responses in Diabetic Patients," the contents of which are incorporated herein by reference.

TECHNICAL FIELD

This invention relates to components and systems for infusing medications such as insulin to patients such as those suffering from diabetes.

BACKGROUND OF THE INVENTION

Infusion pumps are devices used to pump fluid medications into a patient in a controlled manner. One specific type of infusion pump is the insulin pump, which is used for the administration of insulin in treating patients with diabetes mellitus, a process also known as continuous subcutaneous insulin infusion (CSII) therapy. Typically, an infusion pump includes a pump (which includes controls, a processing module, and batteries), a reservoir containing fluid medication (e.g. insulin), an infusion set (which includes a cannula and/or catheter) for subcutaneous insertion into the patient and a tubing system connecting the reservoir to the cannula/catheter. Upon insertion into a patient, the infusion set (more particularly the inserted cannula) is typically maintained in a transcutaneous position at the infusion site for multiple days to allow for continuous delivery of fluid medication. Cannulas and catheters provide passageways for delivering the medication to the patient.

Persistent problems associated with systems designed to infuse medication include having components that can be difficult for some patients to use, and also that the human body spontaneously reacts against foreign bodies which are introduced into the body, such as an implanted cannula (including plastic catheter or metal needle) (see, e.g. U.S. Pat. No. 5,219,361). Among the various responses of a body to foreign bodies, inflammation and the build-up of fibrous tissue at the infusion site significantly shortens the duration that an infusion set may be maintained at a single infusion site (i.e. "site-loss"). Moreover, tissue encapsulation and blockage of the implanted cannula or catheter (i.e. "occlusion") often occurs, thereby impeding or halting infusion of medication. Thus, frequent re-positioning of the infusion site for continued usage of the infusion pump is required. Currently, wear times of all the commercial insulin infusion sets are labeled for ≤3 days.

Patients may also experience scar tissue buildup around an inserted cannula, resulting in a hard bump under the skin after the cannula is removed. The scar tissue does not heal particularly fast, so years of wearing an infusion pump and changing the infusion site will result in a decrease of viable infusion sites. Furthermore, for example with diabetic patients, the areas with scar tissue build-up generally have lower insulin sensitivity, which in turn may affect basal rates and bolus amounts. In some extreme cases, the delivery of insulin will appear to have little to no effect on lowering blood glucose levels and require a change in the infusion site location.

SUMMARY OF THE INVENTION

As noted above, problematical foreign-body responses to cannulas (e.g. plastic catheters or metal needles) inserted in vivo can include coagulation, occlusion, inflammation, and/or encapsulation of the cannula/catheter. The invention disclosed herein is designed to address problems associated with such phenomena through optimized infusion system components including fluid depot materials. tubing, tubing connector interfaces and the like. Embodiments of the invention include components and systems that utilize materials comprising agents identified as having an ability to inhibit foreign body responses at a cannula insertion site (e.g. heparin), thereby inhibiting such problematic phenomena. Typical embodiments of the invention are useful for diabetic patients that are infusing insulin via a cannula in order to regulate blood sugar levels.

Illustrative embodiments of the invention include systems and system components having one or more depots/reservoirs filled with a polyvinyl alcohol foam material that is connected to fluid conduits for delivering insulin to a diabetic patient at a single site of infusion over a period of time. Such systems and components can further include a site loss mitigating agent within the one or more depots that inhibits at least one of coagulation at the single site of infusion, inflammation at the single site of infusion, and encapsulation of the cannula at the single site of infusion. These systems and components can include additional components such as a medication reservoir comprising an insulin solution, a cannula adapted for subcutaneous insertion into a tissue of a diabetic patient at the single site of infusion, and flexible yet kink resistant tubing in operable contact with the medication reservoir and the cannula. These systems are useful in methods for inhibiting a foreign body response in a diabetic patient receiving insulin at a single infusion site over an extended time period, such as least four or more days.

Embodiments of the invention include a fluid conduit adapted to transport an insulin solution from a medication reservoir to a diabetic patient, and a depot in operable contact with the fluid conduit through which to insulin solution flows. This depot includes a foam/sponge and other materials disposed therein that are selected to have one or more material properties that have been discovered to facilitate the infusion of insulin at a single site over an extended period of time (e.g. at least 4, 5, 6, 7, 8 or 9 days). The foam/sponge material may be a polyvinyl alcohol (PVA, used mostly in the illustrative examples), a cellulose, a polyurethane, a polyester, a polyether, a collagen or the like.

This foam material is typically crosslinked and comprises a plurality of pores that are connected three dimensionally through which fluid flows from a conduit on one area of the depot, through the foam material to a conduit on another area of the depot. In some embodiments of the invention, the crosslinked foam material comprises pores having sizes between 0.1 and 5 mm (e.g. pores having sizes from 0.3 mm to 1 mm). In some embodiments of the invention, the foam material exhibits a porosity of from 50% to 95% (e.g. a porosity from 90% to 95%). In some embodiments of the invention, the foam material exhibits a dry density of between 0.1 and 1.5 grams per cubic inch (e.g. a dry density of between 0.8 and 1.5 grams per cubic inch). In some embodiments of the invention, the foam material absorbs an aqueous solution so as to saturate the material by at least 95% in a time between 0.1 and 1 minutes (e.g. a time between 3 and 30 seconds). In some embodiments of the invention, the foam material exhibits an ability to retain a liquid insulin solution such that the weight of the retained insulin solution is from 5 to 100 times (e.g. from 10 to 25 times) the weight of the foam material in the absence of an insulin solution. The foam material typically exhibits an ability to trap: (1) insulin aggregates that occur in insulin solutions; (2) air bubbles that occur in insulin solutions; and/or (3) particulates such as dust that occur in insulin solutions. Typically, the foam material forms a layer within the depot that is of a certain thickness, for example from 5 to 5000 mils thick (e.g. from 100 to 200 mils thick).

In typical embodiments of the invention, a site-loss mitigating agent is disposed in the depot and adapted to contact the insulin solution as the insulin solution flows through the depot. Typically, this site-loss mitigating agent is selected to inhibit at least one of: coagulation at the site of infusion, inflammation at the site of infusion, and encapsulation of the cannula at the site of infusion. In an exemplary embodiment, the site-loss mitigating agent comprises heparin in an amount sufficient to inhibit inflammation at the single site of infusion for at least 4, 5, 6, 7, 8 or 9 days.

The system can also include a membrane in operable contact with the fluid conduit (either upstream or downstream of fluid flow), for example a membrane is formed from a polymeric material having pores that are between 0.1 μm to 10 μm in diameter, and the membrane exhibits an ability to trap particulates in insulin solutions, and also an ability to trap insulin aggregates that form in insulin solutions. Optionally for example, the membrane comprises at least one of: an acrylic copolymer membrane with pore sizes of about 0.1 to 10 μm, a polyethersulfone membrane with pore sizes of about 0.1 to 10 μm, a mixed cellulose esters membrane with pore sizes of about 0.1 to 10 μm, a cellulose acetate membrane with pore sizes of about 0.1 to 10 μm, a cellulose nitrate membrane with pore sizes of about 0.1 to 10 μm, a nylon membrane with pore sizes of about 0.21 to 10 μm, a hydrophilic polytetrafluoroethylene (PTFE) membrane with pore sizes of about 0.1 to 10 μm, or a polycarbonate membrane with pore sizes of about 0.1 to 10 μm.

Embodiments of the system for delivering insulin to a diabetic patient include additional components such as at least one of: (a) medical tubing preventing loss of ingredients (such as preservatives) and protecting formulation integrity during insulin infusion; (b) medical tubing formed from a plurality of layers of polymeric materials, optionally wherein a polymeric material is formed with internal ribs designed to inhibit kinking; (c) medical tubing formed to include an area of color or opacity that facilitates visualization of fluid flow through the tubing; (d) medical tubing comprising a connector at an end of the tubing, wherein: the connector comprises a matrix impregnated with a site loss reducing agent such as heparin, (e) medical tubing comprising a tubing connector coupled to the heparin depot so at to allow a first tubing conduit component to connect to a second tubing conduit component; wherein the depot comprises a matrix impregnated with heparin, (f) an infusion hub adapted to be affixed to the skin of a patient and infuse insulin, wherein the infusion hub comprises a matrix impregnated with heparin, (g) an adhesive transdermal patch designed to affix an infusion catheter to a site of infusion, wherein the transdermal patch is formed from a plurality of layered materials and a movable liner, and the adhesive transdermal patch comprises a matrix impregnated with heparin, (h) a reservoir connector adapted to operably connect infusion tubing to a medication reservoir, wherein the reservoir connector comprises a matrix impregnated with heparin, and a luer connector, or (i) a medication reservoir comprising an insulin solution having selected properties (e.g. an insulin solution that does not include a protease inhibitor and/or one comprising human insulin and not an insulin analog).

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 7A is an enlarged, partial sectional view of a cannula inserted in a patient for directly infusing medication into the patient's tissue. FIG. 7B is an enlarged, partial longitudinal sectional view of the distal end of a drug-coated cannula. FIG. 7C is a view similar to that of FIG. 7B, but of another embodiment of the cannula according to the invention. FIG. 7D is a view similar to that of FIG. 7B, but of another embodiment of the cannula according to the invention.

FIGS. 28A-D are views showing an embodiment of a connector. FIG. 28A is a top-down view of the connector. FIG. 28B is a cross-sectional view of the connector taken along the line A-A in FIG. 28A. FIG. 28C is an enlarged view of circled portion B in FIG. 28B. FIG. 28D is an enlarged view of circled portion C in FIG. 28B.

FIGS. 29A-C are views showing an embodiment of a connector. FIG. 29A is a top-down view of the connector. FIG. 29B is a cross-sectional view of the connector taken along the line D-D in FIG. 29A. FIG. 29C is a side view of the connector.

FIGS. 31A-31F show views of a luer connection embodiment.

FIGS. 32A-32H show views of embodiments of connectors and connector interfaces, elements which can comprise the drug loaded materials (e.g. heparin) disclosed herein. FIG. 32A-32C shows embodiments of reservoir and infusion site connectors; FIG. 32D shows embodiments of a connector to a medication (e.g. insulin) reservoir such as one disposed in an infusion pump; FIG. 32E shows embodiments of a tubing connector and infusion site connector interface; FIG. 32F shows an embodiment of a septum such as one disposed in an infusion pump medication reservoir; FIG. 32G shows embodiments of a tubing connector; and FIG. 32H shows embodiments of a tubing connector and infusion site connector interface.

In FIG. 37A, the panel on the left shows a schematic of an embodiment of the invention having the membrane, while the upper panel on the right provides a cartoon showing this membrane filtering a solution such as an insulin formulation. In FIG. 37A, the lower panel on the right provides data showing the reduction of particle counts that occurs via this membrane filtration. In FIG. 37B, the panel on the left shows a schematic of an embodiment of the invention having the two depots comprising a polyvinyl alcohol foam material, while the panel on the right provides a cartoon showing the polyvinyl alcohol foam material trapping gas in a solution such as an insulin formulation.

DETAILED DESCRIPTION OF THE INVENTION

Figure 1:
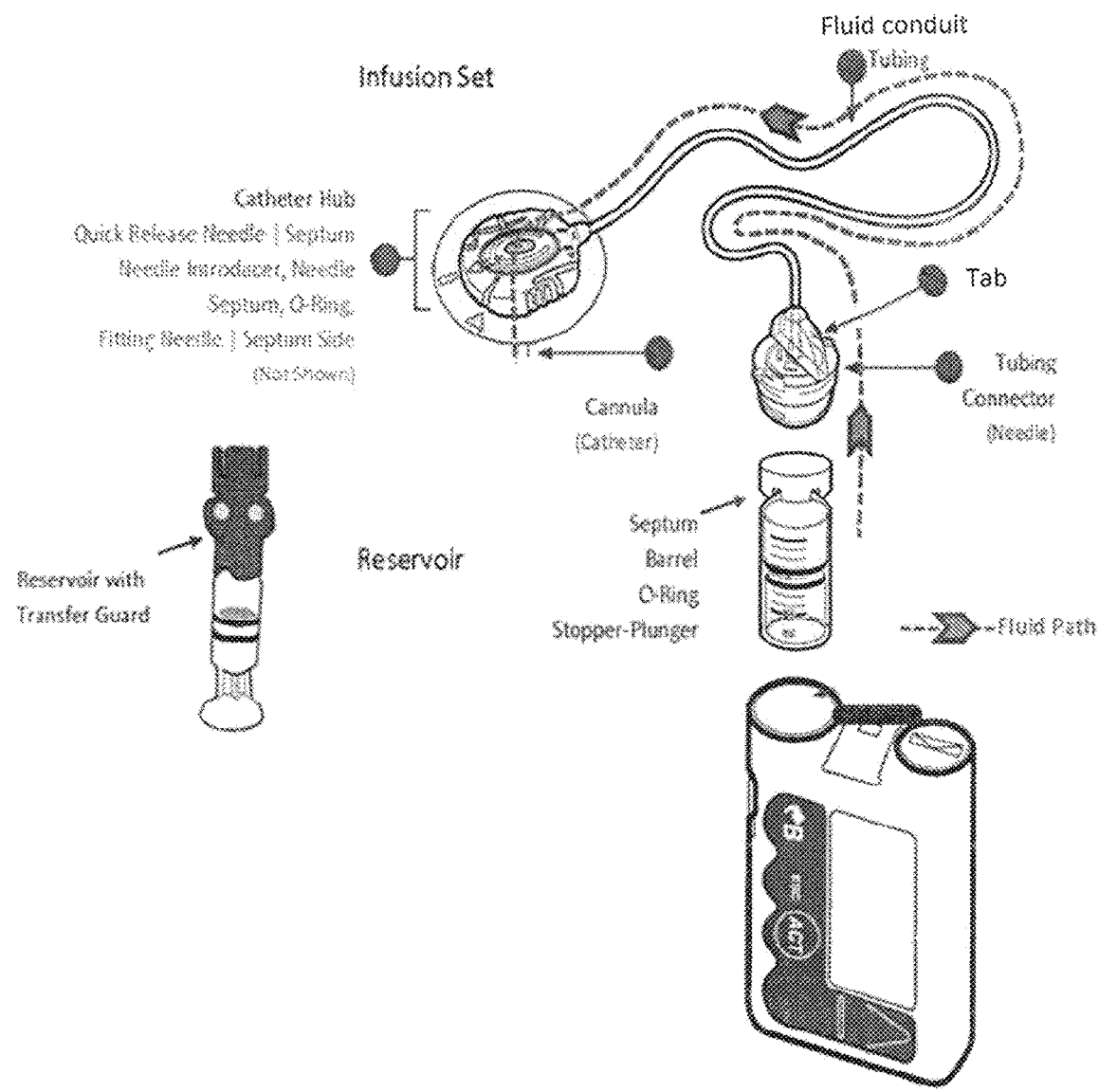
FIG. 1 is a schematic of the components included in an infusion pump and the fluid path for delivering a fluid medication.

In the description of preferred embodiments, reference is made to the accompanying drawings which form a part hereof, and in which is shown by way of illustration a specific embodiment in which the invention may be practiced. It is to be understood that other embodiments may be utilized and structural changes may be made without departing from the scope of the present invention. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

While the invention described herein is useful in a variety of contexts, embodiments disclosed herein are primarily designed for use with insulin infusion systems such as an infusion pump for delivery of fluid medication comprising a combined fluid pump and reservoir and an infusion catheter. It is also within the scope of the invention to use a catheter access port or additional forms of implantable pump systems in place of a combined fluid pump and reservoir disclosed. An example of a suitable catheter access port is disclosed in U.S. Pat. No. 5,137,529 issued to David A. Watson, Mark J. Licata, Alfons Heindl and Edward C. Leicht on Aug. 11, 1992 entitled "Injection Port" and assigned to Medtronic-PS Medical, the disclosure of which is incorporated herein by reference in its entirety. Examples of additional implantable pump systems are disclosed in U.S. Pat. No. 4,588,394 issued to Rudolf R. Schultz, Gary P. East and Alfons Heindle on May 13, 1986 entitled "Infusion Reservoir and Pump System", U.S. Pat. No. 4,681,560 issued to Rudolf R. Schultz, Gary P. East and Alfons Heindle on Jul. 21, 1987 entitled "Subcutaneous Infusion Reservoir and Pump System", U.S. Pat. No. 4,761,158 issued to Rudolf R. Schultz, Gary P. East and Alfons Heindle on Aug. 2, 1988 entitled "Subcutaneous Infusion Reservoir and Pump System", U.S. Pat. No. 4,816,016 issued to Rudolf R. Schultz, Gary P. East and Alfons Heindle on Mar. 28, 1989 entitled "Subcutaneous Infusion Reservoir and Pump System", U.S. Pat. No. 4,867,740 issued to Gary P. East on Sep. 19, 1989 entitled "Multiple-Membrane Flow Control Valve and Implantable Shunt System", U.S. Pat. No. 5,085,644 issued to David A. Watson and Mark J. Licata on Feb. 4, 1992 entitled "Sterilizable Medication Infusion Device with Dose Recharge Restriction" and U.S. Pat. No. 5,152,753 issued to Stephen W. Laguette, Gary P. East, David A. Watson and Thomas J. Carlisle on Oct. 6, 1992 entitled "Medication Infusion Device with Dose Recharge Restriction", all of which are assigned to Medtronic-PS Medical, the disclosures of which are incorporated herein by reference in their entirety.

Additionally, the infusion pumps and systems described in U.S. Pat. No. 6,110,155, titled "Anti-inflammatory-agent-loaded catheter and method for preventing tissue fibrosis," U.S. patent application Ser. No. 11/897,106, titled "Combined sensor and infusion set using separated sites," U.S. patent application Ser. No. 12/184,046, titled "Analyte sensor apparatuses having improved electrode configurations and methods for making and using them," and U.S. patent application Ser. No. 13/010,640, titled "Layered enzyme compositions for use with analyte sensors" are incorporated herein by reference in their entirety.

Aspects and Embodiments of the Invention

Diabetes mellitus (DM) is the most common cause of hyperglycemia, a condition of high blood glucose that occurs when the body has too little insulin (type 1 and some type 2 DM) or is unable to utilize insulin properly (type 2 DM). One method of treating a diabetic patient is with the use of an infusion system, typically an insulin pump. An infusion pump provides for the infusion of a medication or drug composition, such as insulin or an insulin analog, to a patient. The infusion pump is typically worn by the patient, but may also be attached to or implanted in the patient. The infusion pump comprises any suitable means for conveying fluid medication to a targeted location (i.e. infusion site) on a patient's body by way of a cannula (e.g. a plastic catheter or a metal needle).

Typically, the infusion pump systems comprise a combined fluid pump and insulin reservoir and an infusion set, which comprises a cannula/catheter. In one embodiment, as shown in FIG. 1, the infusion pump includes a self-contained reservoir for storing medication, a pump for drawing the fluid medication from the reservoir and advancing it by way of an infusion cannula to the tissue of the patient to be treated. A suitable power source, such as a battery, is used to energize the pump. The infusion pump may be programmed to deliver prescribed amounts of medication continuously (e.g. basal insulin rate), on demand (e.g. bolus of insulin) or at regularly scheduled intervals. The infusion pump also includes an infusion set which comprises components to be inserted into the patient, such as an insertion needle and a cannula (or catheter). The cannula is a thin tube used for the introduction of fluid medication to the target site. Generally, a proximal end of the cannula is attached via a tubing system and connector to the reservoir and fluid pump, located outside the patient's body. An opposite, distal end of the cannula is inserted into the patient trans/subcutaneously and adapted to be positioned in close proximity to the tissue intended to receive the fluid medication. A lumen extends from the proximal end to the distal end of the cannula to conduct the flow of fluid therebetween. The infusion set also includes an insertion needle, which is assembled with the soft cannula (catheter) and is adapted to pierce the patient's skin for trans/subcutaneous cannula placement. The insertion needle is left inside as hard cannula or thereafter withdrawn to leave the soft cannula in place for subcutaneous fluid infusion.

As shown in the Figures and discussed in detail below, components of the systems include kink resistant tubing and/or associated tubing connector interfaces. For example, certain embodiments of the invention include flexible medical tubing formed from a plurality of materials and having both kink resistant and preservative retention properties. Embodiments of the medical tubing can contain two or three layers (including a tie layer) of material with or without internal ribs. Embodiments of the invention include a drug delivery infusion set with these tubing embodiments coupled with unique connectors (optionally both at distal and proximal ends, e.g. as shown in FIGS. 27-32) that can be connected to a pump or injector to deliver drugs/therapeutic agents such as insulin. The tubing can also be extruded with a color to enhance the contrast between the fluid and plastic tubing for visual monitoring of the flowing material to confirm flow and check for bubbles. In illustrative embodiments of the invention, tubing connectors designed to connect to an infusion site hub (proximal end) can be loaded with heparin or other drug loaded foam having characteristics discussed below. In embodiments of the invention, an infusion site hub can also be loaded with heparin or other drug loaded foam to improve infusion site viability. Embodiments of the invention include a transdermal patch designed for use with the above-noted tubing and/or connector and/or hub embodiments. Optionally this patch is formed to include a material comprising a site loss mitigating agent.

Related embodiments of the invention include methods for delivering insulin to a diabetic patient at a single site of infusion over a period of time (e.g. at least three or at least seven or at least 10 days), the method comprising infusing the insulin at the single site of infusion using a system or components as disclosed herein. Typically in these methods, the system that delivers insulin to the diabetic patient comprises a medication reservoir comprising an insulin solution, a cannula adapted for subcutaneous insertion into a tissue of a diabetic patient at the single site of infusion, a fluid conduit in operable contact with the medication reservoir and the cannula and adapted to deliver insulin from the medication reservoir to the single site of infusion, and a site loss mitigating agent that inhibits at least one of coagulation at the single site of infusion, inflammation at the single site of infusion, and encapsulation of the cannula at the single site of infusion. In some embodiments of the invention, the response-inhibiting agent is heparin and is administered in an amount between 40 U/device to 8000 U/device and at a dose of 0.1 to 80 U/kg/day. In some embodiments of the invention, a response-inhibiting agent can comprise dextran (e.g. alone or in combination with another agent such as heparin) and is administered in an amount between 0.002-0.4 mg/kg/day.

Optionally the site loss mitigating agent is disposed within one or more depots and adapted to contact an insulin solution as the insulin solution flows from the medication reservoir to the single site of infusion and is further administered according to a specific delivery profile (e.g. a first immediate dose, followed by a second sustained dose of heparin). In certain embodiments of the invention, the response-inhibiting agent is released in accordance to a plurality of delivery profiles. Such profiles can include, for example, an immediate release profile wherein the response-inhibiting agent is administered to the patient from 0 to 6 hours following insertion of the cannula and/or an extended release profile wherein the response-inhibiting agent is administered to the patient at least 48 hours or at least 72 hours following insertion of the cannula. In some embodiments of the invention, the response-inhibiting agent coats the cannula for an immediate release profile and/or the response-inhibiting agent is impregnated with a material that that coats the cannula for an extended release profile.

The invention disclosed herein includes a number of systems and associated components for delivering insulin to a diabetic patient at a single site of infusion. Such embodiments of the invention include a fluid conduit adapted to transport an insulin solution from a medication reservoir to the diabetic patient, and a depot in operable contact with the fluid conduit through which to insulin solution flows. This depot has a foam/sponge material disposed therein that is selected to have one or more material properties that have been discovered to facilitate the infusion of insulin at a single site over an extended period of time (e.g. at least 4, 5, 6, 7, 8 or 9 days). The foam/sponge material may be polyvinyl alcohol (PVA, used mostly in the examples), cellulose, polyurethane, polyester, polyether, collagen etc. This foam materials is typically crosslinked and comprises a plurality of pores (i.e. comprises a plurality of interconnected hollow voids) that are connected three dimensionally through which fluid flows from a conduit on one area of the depot, through the foam material to a conduit on another area of the depot. In some embodiments of the invention, the crosslinked foam material comprises pores having sizes between 0.1 and 5 mm (e.g. pores having sizes from 0.3 mm to 1 mm). In some embodiments of the invention, the foam material exhibits a porosity of from 50% to 95% (e.g. a porosity from 90% to 95%). In some embodiments of the invention, the foam material exhibits a dry density of between 0.1 and 1.5 grams per cubic inch (e.g. a dry density of between 0.8 and 1.5 grams per cubic inch). In some embodiments of the invention, the foam material absorbs an aqueous solution so as to saturate the polyvinyl alcohol foam material by at least 95% in a time between 0.1 and 1 minutes (e.g. a time between 3 and 30 seconds). In some embodiments of the invention, the foam material exhibits an ability to retain a liquid insulin solution such that the weight of the retained insulin solution is from 5 to 100 times (e.g. from 10 to 25 times) the weight of the polyvinyl alcohol foam material in the absence of an insulin solution. The foam material typically exhibits an ability to trap: (1) insulin aggregates that occur in insulin solutions; (2) air bubbles that occur in insulin solutions; and/or (3) particulates such as dust air bubbles that occur in insulin solutions. Typically, the polyvinyl alcohol foam material forms a layer in the that is of a certain thickness, for example from 5 to 5000 mils thick (e.g. from 100 to 200 mils thick).

PVA sponge materials useful in embodiments of the invention and method for making such materials are known in the art (see, e.g. U.S. Pat. Nos. 4,083,906 and 6,6456,206, the contents of which are incorporated by reference). Such materials have a porous structure, and is typically made from water soluble PVA acetalized with an acid catalyst. During the acetalizing process, a pore forming agent or method (e.g. starch or air) is added. In starch pore forming methods, starch creates the pores and is then extracted in the washing process. In air pore forming methods, gas or air creates the pores. After a water soluble porous structure is made, the agent (e.g. starch) is extracted. In the case of air pore forming, there is no need to remove any additional material. The finished product has a three-dimensional, interconnected porous structure. The finished product can then be washed/rinsed.

In typical embodiments of the invention, a site-loss mitigating agent is disposed in the depot with the polyvinyl alcohol foam material. This site-loss mitigating agent is adapted to contact the insulin solution as the insulin solution flows through the depot. Typically, this site-loss mitigating agent is selected to inhibit at least one of: coagulation at the site of infusion, inflammation at the site of infusion, and encapsulation of the cannula at the site of infusion. As is known in the art, heparin comprises a number of discreet biological activities that are separate from it anti-coagulant activities (e.g. anti-inflammatory activities) and embodiments of the invention focus on the use of heparin for these non-anticoagulant activities (see, e.g. Poterucha et al., Thromb Haemost. 2017 Feb. 28; 117(3):437-444 and Cassinelli et al., Int J Cardiol. 2016 June; 212 Suppl 1:S14-21). In an exemplary embodiment, the site-loss mitigating agent comprises heparin in an amount sufficient to inhibit inflammation at the single site of infusion for at least 4, 5, 6, 7, 8 or 9 days.

The system typically includes a number of other components such as a cannula that is in operable contact with the fluid conduit and the depot, and adapted for subcutaneous insertion into a tissue of a diabetic patient at the single site of infusion. The system can also include a membrane in operable contact with the fluid conduit (either upstream or downstream of fluid flow), for example a membrane is formed from a polymeric material having pores that are between 0.1 μm to 10 μm in diameter, and the membrane exhibits an ability to trap particulates in insulin solutions, and also an ability to trap insulin aggregates that form in insulin solutions. Optionally for example, the membrane comprises at least one of: an acrylic copolymer membrane with pore sizes of about 0.1 to 10 μm, a polyethersulfone membrane with pore sizes of about 0.1 to 10 μm, a mixed cellulose esters membrane with pore sizes of about 0.1 to 10 μm, a cellulose acetate membrane with pore sizes of about 0.1 to 10 μm, a cellulose nitrate membrane with pore sizes of about 0.1 to 10 μm, a nylon membrane with pore sizes of about 0.21 to 10 μm, a hydrophilic polytetrafluoroethylene (PTFE) membrane with pore sizes of about 0.1 to 10 μm, or a polycarbonate membrane with pore sizes of about 0.1 to 10 μm.

Figure 37A:
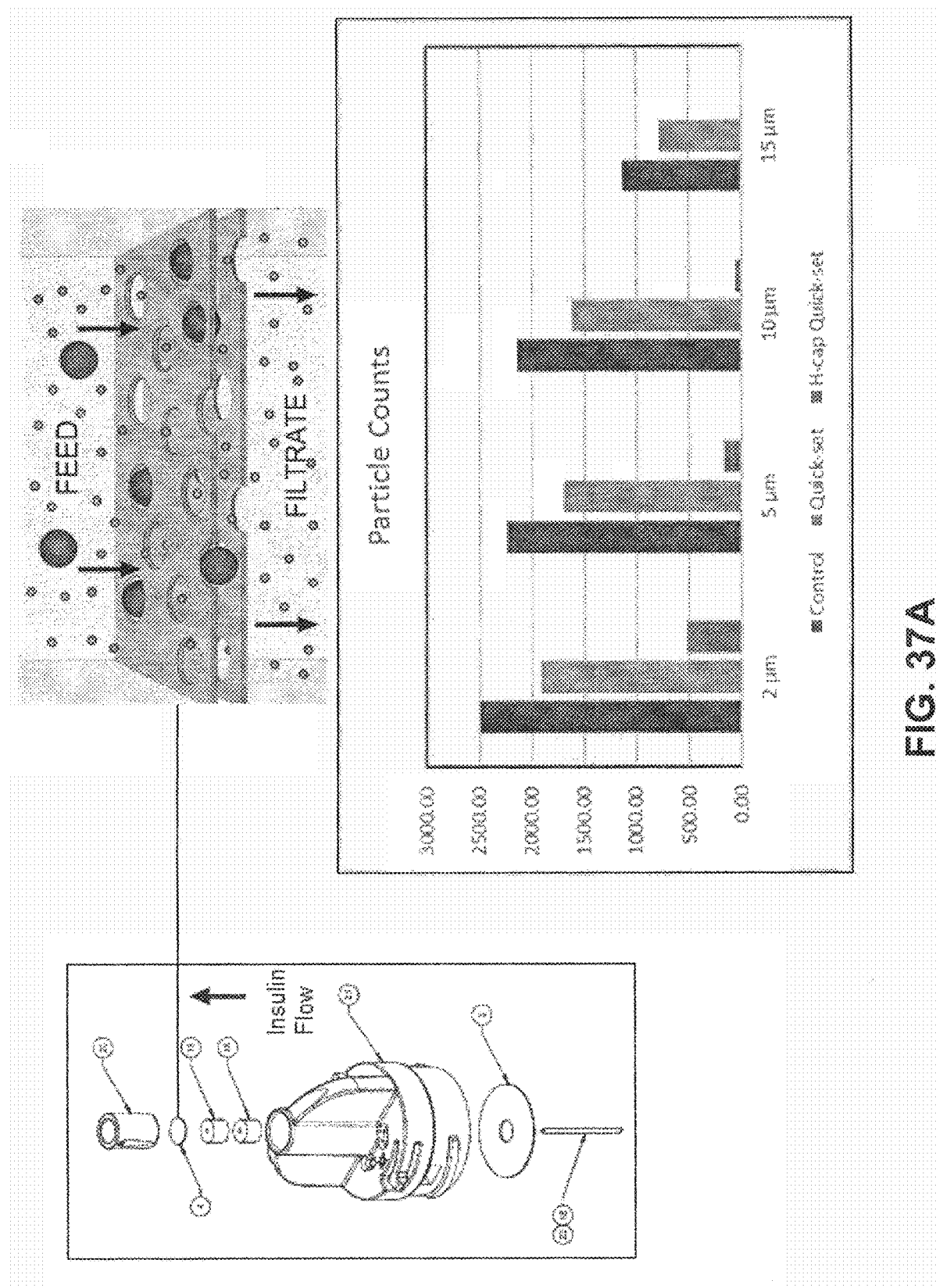
FIGS. 37A-37B provides schematics and data showing how the membranes and polyvinyl alcohol foam materials of the invention can decrease localized immune responses.
Figure 37B:
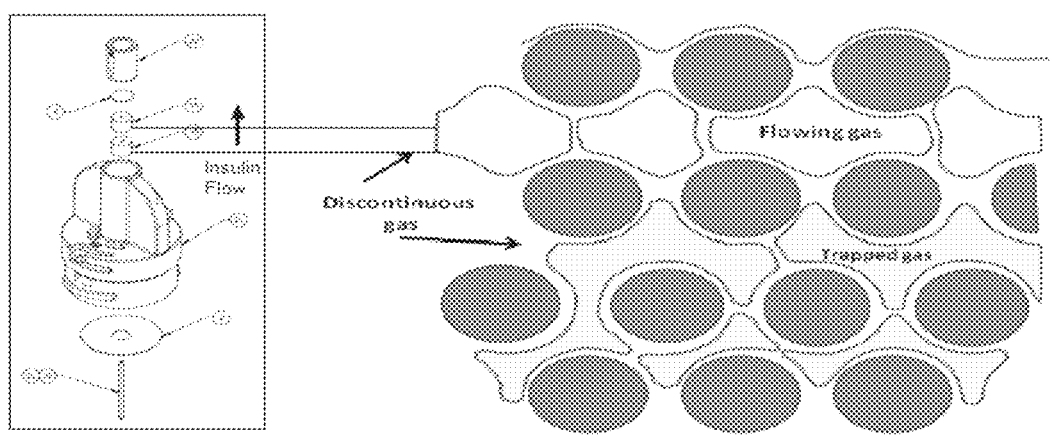

Embodiments of the invention having the polyvinyl alcohol foam material and/or the membrane that are discussed immediately above utilize these materials to reduce inflammation at the infusion site, even in the absence of a site loss mitigating agent such as heparin. In this context, without being bound by a specific theory or mechanism of action, it is believed that inflammation at an infusion site can result from a number of factors including the presence of hydrophobic contaminants such as silicone oil, particulates such as dust and insulin fibrils/aggregates that can occur in insulin formulations present in medication reservoirs. As shown in FIG. 37A, in embodiments of the invention, the membrane acts as a filter which removes particulates from the infusion system, thereby improving insulin stability and decreasing localized immune responses. As shown in FIG. 37B, in embodiments of the invention, the polyvinyl alcohol foam material disclosed herein can trap gas bubbles that occur in infusion systems (gas bubbles which can lead to insulin aggregation), thereby improving insulin stability and decreasing localized immune responses. In this context, certain constellations of elements (e.g. systems that include a membrane filter in combination with a depot comprising the polyvinyl alcohol foam material disclosed herein) can act together in a manner that optimizes insulin stability and decreases localized immune responses. In addition, the inclusion of a of a site loss mitigating agent such as an anti-inflammatory agent (e.g. heparin disposed within one or more depots containing the polyvinyl alcohol foam material disclosed herein) can further reduce inflammation at the infusion site over an extended period of time such as 4, 5, 6, 7, 8 or 9 days.

Embodiments of the system for delivering insulin to a diabetic patient can include additional components such as at least one of: (a) medical tubing formed from a plurality of layers of polymeric materials, optionally wherein a polymeric material is formed with internal ribs designed to inhibit kinking; (b) medical tubing formed to include an area of color or opacity that facilitates visualization of fluid flow through the tubing; (c) medical tubing comprising a connector at an end of the tubing, wherein: the connector comprises a matrix impregnated with heparin, or a magnetic washer, (d) medical tubing comprising a tubing connector coupled to the heparin depot so at to allow a first tubing conduit component to connect to a second tubing conduit component; wherein the depot comprises a matrix impregnated with heparin, (e) an infusion hub adapted to be affixed to the skin of a patient and infuse insulin, wherein the infusion hub comprises a matrix impregnated with heparin, (f) an adhesive transdermal patch designed to affix an infusion catheter to a site of infusion, wherein the transdermal patch is formed from a plurality of layered materials and a movable liner, and the adhesive transdermal patch comprises a matrix impregnated with heparin, (g) a reservoir connector adapted to operably connect infusion tubing to a medication reservoir, wherein the reservoir connector comprises a matrix impregnated with heparin, and a luer connector, or (h) a medication reservoir comprising an insulin solution.

In certain embodiments of the invention (see, e.g. FIG. 27), the system further comprises a recess for a medication reservoir comprising an insulin solution, a cap for coupling the medication reservoir to the fluid conduit, a housing engagement member comprising a detent or a thread projecting outward from a cylindrical external surface of the cap and adapted to engage an engagement member disposed in a housing recess within an insulin infusion device, wherein the cap connects with the fluid medication reservoir and both the cap and the fluid medication reservoir at least partially fit inside the housing recess of the infusion device and are insertable and removable from the housing recess within the infusion device upon rotation of the cap, a conduit cavity disposed in the cap and adapted to secure the fluid conduit to the cap, a first tab disposed on the cap so as to provide a first surface for a user to grip and twist the cap to engage the cap with the infusion device upon rotation of the cap, wherein the first tab projects outward from the cap such that the first surface of the first tab is disposed in an orientation perpendicular to a plane defined by the circumference of the cap, and a vent disposed in the cap that permits the passage of air and simultaneously inhibits the passage of fluids so as to permit fluid resistant venting of air through the vent and equalization of pressure inside the infusion device to atmospheric pressure outside the infusion device.

Another embodiment of the invention is a method of making an insulin infusion system component comprising: connecting a depot to a fluid conduit adapted to transport an insulin solution from a medication reservoir to a diabetic patient, wherein the depot comprises a polyvinyl alcohol foam material disposed therein, and this polyvinyl alcohol foam material is selected to have one or more of the characteristics disclosed herein such as pores having sizes between 0.1 and 5 mm (e.g. pores having sizes from 0.3 mm to 1 mm) and an ability to trap insulin aggregates that form in insulin solutions; and an ability to trap air bubbles that form in insulin solutions. This method further comprises connecting the fluid conduit to a cannula, wherein the cannula is in fluid contact with the depot and adapted for subcutaneous insertion into a tissue of a diabetic patient. Typical embodiments of this method further comprise disposing a site-loss mitigating agent in the depot, wherein the site-loss mitigating agent is adapted to contact an insulin solution as the insulin solution flows through the depot, and the site-loss mitigating agent inhibits at least one of: coagulation at the site of infusion, inflammation at the site of infusion, and encapsulation of the cannula at the site of infusion. Optionally, the site-loss mitigating agent comprises heparin in an amount sufficient to inhibit inflammation at the single site of infusion for at least 4, 5, 6, 7, 8 or 9 days. Heparin useful in such embodiments is well known in the art (e.g. heparin sodium lyophilized, item number 03005 sold by CELSUS LABORATORIES INC.).

The methods of making an insulin infusion system component can further comprise connecting a fluid medication reservoir comprising insulin to the fluid conduit, wherein the insulin is human insulin and not an insulin analog. The methods of making an insulin infusion system component can further comprise disposing a membrane in operable contact with the fluid conduit upstream of the depot, wherein the membrane is formed from a polymeric material having pores that are between 0.1 µm to 10 µm in diameter, the membrane exhibits an ability to trap impurities that form in insulin solutions, and the membrane exhibits an ability to trap insulin aggregates that form in insulin solutions.

Another embodiment of the invention is a method for modulating the delivery of insulin (e.g. human insulin and not an insulin analog) from a subcutaneous reservoir in a diabetic patient into blood of the patient, the method comprising infusing the insulin into the subcutaneous reservoir of the patient using a system disclosed herein. Optionally, the diabetic patient is identified as exhibiting subcutaneous insulin resistance prior to infusing the insulin into the subcutaneous reservoir of the patient. Typically this systems includes a container comprising an insulin solution, a cannula adapted for subcutaneous insertion into the subcutaneous reservoir of the diabetic patient, a fluid conduit in operable contact with the medication reservoir and the cannula and adapted to deliver the insulin solution from the medication reservoir to the subcutaneous reservoir, a first heparin depot in operable contact with the fluid conduit, a second heparin depot in operable contact with the fluid conduit (which is optional); wherein the first or second depot has a polyvinyl alcohol foam material of the invention disposed therein.

In certain embodiments of the invention, the first and second heparin depot each comprise different amounts of heparin. In some embodiments of the invention, the first and/or second amount of heparin is an amount sufficient to inhibit insulin resistance; and/or increase the insulin reservoir in the subcutaneous space; and/or inhibit inflammation at the single site of infusion for at least 4, 5, 6, 7, 8 or 9 days. In some embodiments of the invention, the first and/or second heparin depot is coupled to the system so as to be readily attachable and detachable. Certain embodiments of the invention include selected insulin formulations, such as those where a protease inhibitor is not included with the insulin. Typically in these methods, the insulin is infused over a period of time greater than 10, 15, 30, 60 or more minutes.

Components of the systems include tubing and associated connector interfaces (see, e.g. those shown in FIG. 1). For example, embodiments of the invention include flexible medical tubing having kink resistant and preservative retention properties. Embodiments of the invention include a drug delivery infusion set with these tubing embodiments coupled with a unique connector (both at distal and proximal ends) that can be connected to a pump or injector to deliver drugs/therapeutic agents such as insulin. This infusion set has enhanced kink-resistant properties that reduce the occurrence of occlusions (e.g. those that can trigger an infusion pump "No Delivery Alarm") caused by kinked tubing during pump infusion therapy and also has capability to reduce the loss of preservatives from the delivered insulin formulation. In addition, the tubing material is designed to exhibit opacity for easy visual observation of flowing solutions. The tubing can also be extruded with a colored strip to enhance the contrast between the fluid and plastic tubing for visual monitoring of the flowing material to confirm flow and check for bubbles.

Embodiments of such infusion set tubing are useful as 7-day (or more) Extended Wear infusion set and Sensor/infusion set designed to allow patients to use an infusion set for an extended period of time without concerns of preservative loss from delivered insulin formulation and/or kinked tubing and also easier for visual monitoring of insulin and air bubbles. Embodiments of the medical tubing contain two or three layers (including a tie layer) of material. The interior layer is typically made of a material such as polypropylene (e.g. with critical parameters at this preferable range: Flexural Modulus: 108,000 psi to 140,000 psi and Melt Flow rate: 10 g/10 min to 27 g/10 min) for insulin compatibility and preservative retention, and the outer layer is made of poly urethane (PU) (other material can also be used—see note below) with an interlock design to strengthen the kink resistance property. In some embodiments of the invention, the interior layer that contact a medication such as insulin comprises polypropylene (homopolymer or copolymer), SIBS, Fluoropolymer (homopolymer or copolymer), PVDF-HFP, EFEP, Tetrafluoroethylene, Hexafluropropylene, THV, manufactured in combination with: SEP, SEPS, SEBS, or SEPS. In some embodiments of the invention, the exterior layer of the tubing comprises PVC, EVA, Polyester or Polyamide. A tri-layer tubing with a tie-layer can enhance the tubing rigidity and kink resistance even without inner rib design and this design demonstrates tubing kink and fatigue resistance. The size of the tubing is an important aspect of the invention, with a preferred inner diameter being: 0.016" (min: 0.005", max: 0.025") and a preferred outer diameter being: 0.060" (min: 0.040", max: 0.080").

Figure 33A:
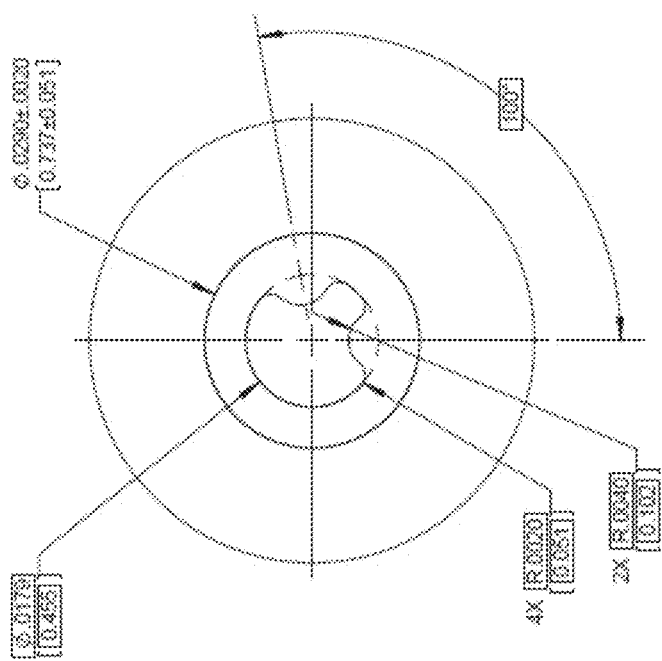
FIGS. 33A-33B show views of embodiments of kink resistant tubing formed from layers of different materials and further comprising ribs.
Figure 33A:
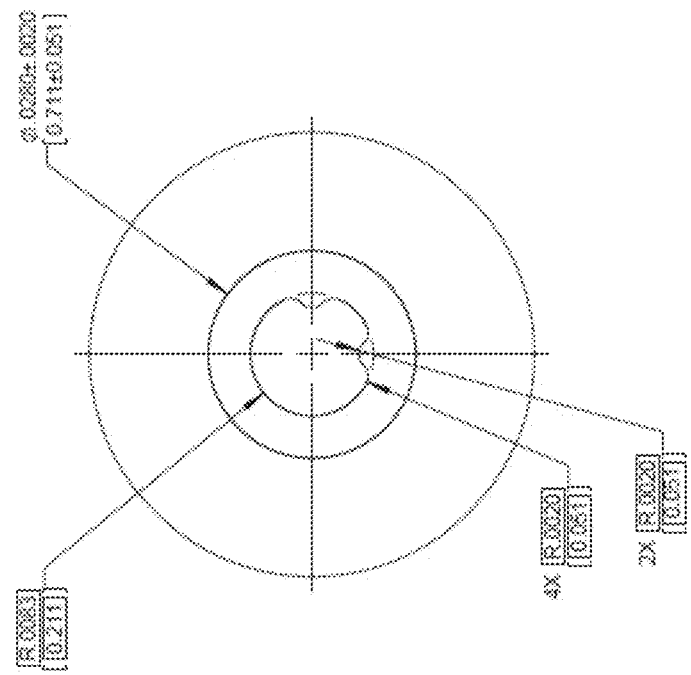
Figure 33B:
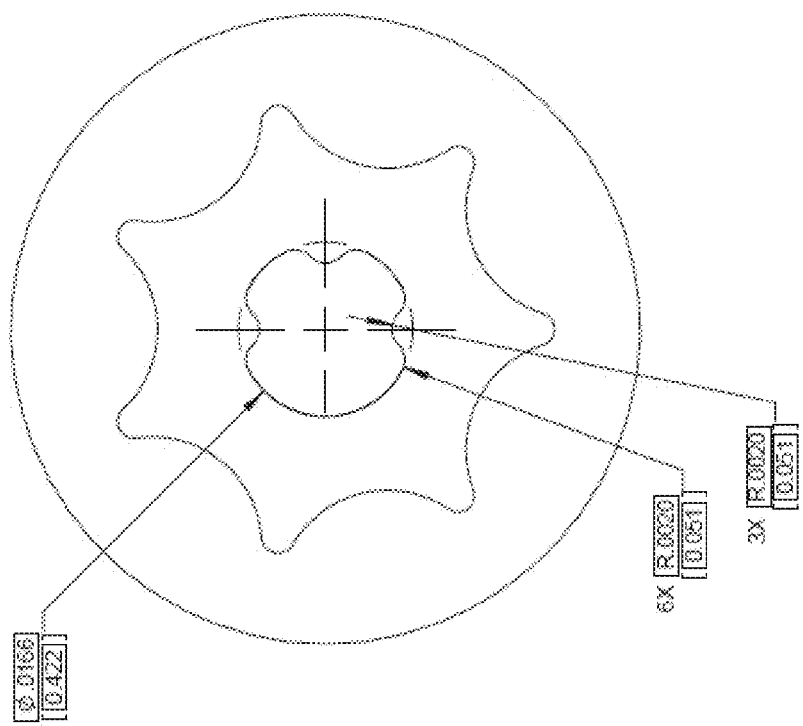
Figure 33B:
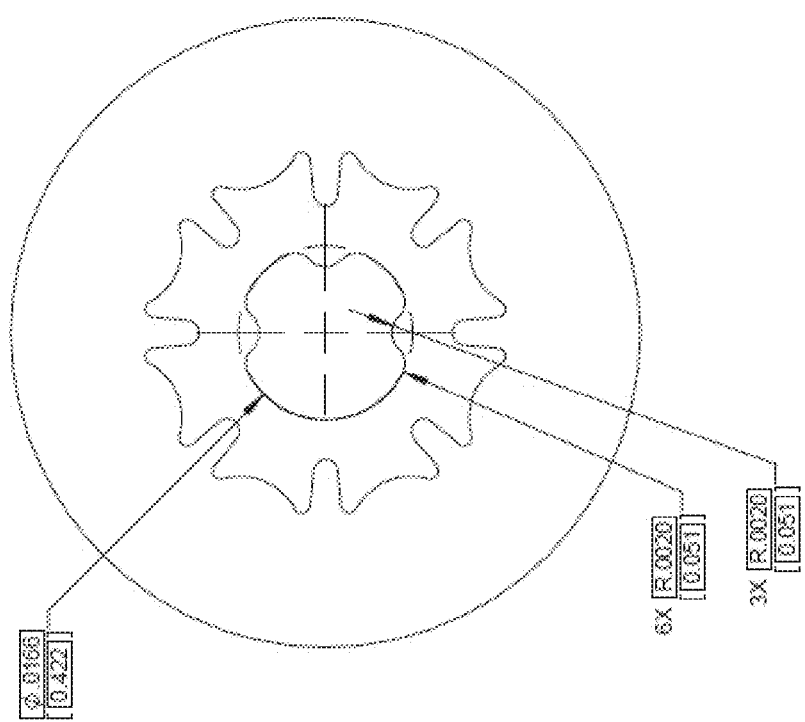

Kink resistance in such tubing embodiments can be further improved with 1 rib, 2 ribs (either 90° or 180° apart), 3 ribs and 4 ribs designs. The inter layer surface design is depicted in FIGS. 33A and 33B (u, tubing interior is designed with 1 rib, 2 ribs (either 90° or 180° apart), 3 ribs and 4 ribs to eliminate complete tubing closure during bending, and the outer layer has a particular cross-section such as a flower shaped cross-section or a star shaped cross-section to enable the tubing to produce kink resistant properties. The inner and outer layer design can be combined for various design configurations (see, e.g. U.S. patent application publication 2015/0053298, the contents of which are incorporated herein by reference). In embodiments of the invention, the transparency (or opacity) of plastic tubing can be varied by adding specially formulated modifiers to the outer layer tubing material or to extrude the tubing with a color strip to provide contrast for visual monitoring of fluid flow and to decrease insulin exposure to ambient light.

Figure 30A:
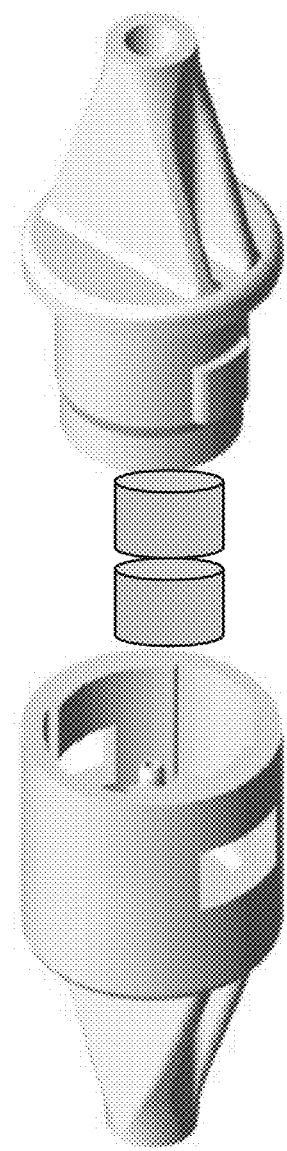
FIG. 30A shows a view of an embodiment of a Quick Release In-line Heparin Depot connector (In-line assembly between the Catheter Hub and Pcap connected with tubing where the Depot can be Quick Release or fixed to the tubing and the Depot can be attached to the Catheter Hub at fixed distance and have variation in the remaining variation in lengths)
Figure 30B:
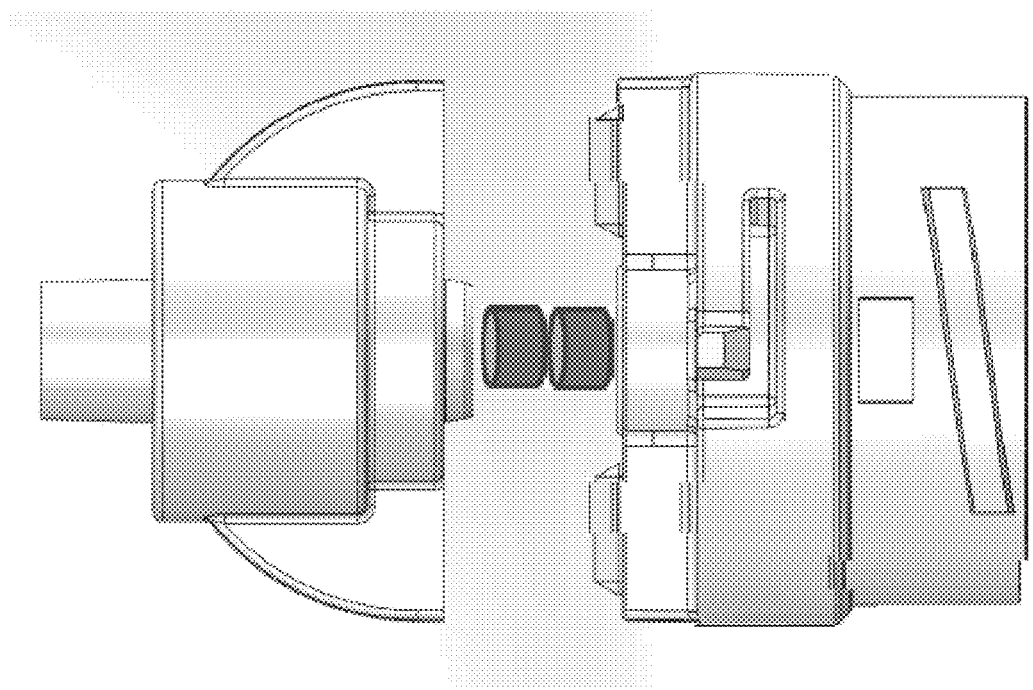
FIG. 30B shows a Luer Lock Connection embodiment with exploded view with foams shown. These connector embodiments can comprise of one or more foam, sponge, or polymeric materials loaded with various amount of heparin (e.g. 50 U-500 U). In such embodiments, the heparin can be released from depot (cylindrical elements at center) through contacting the insulin fluid path.
Figure 32A:
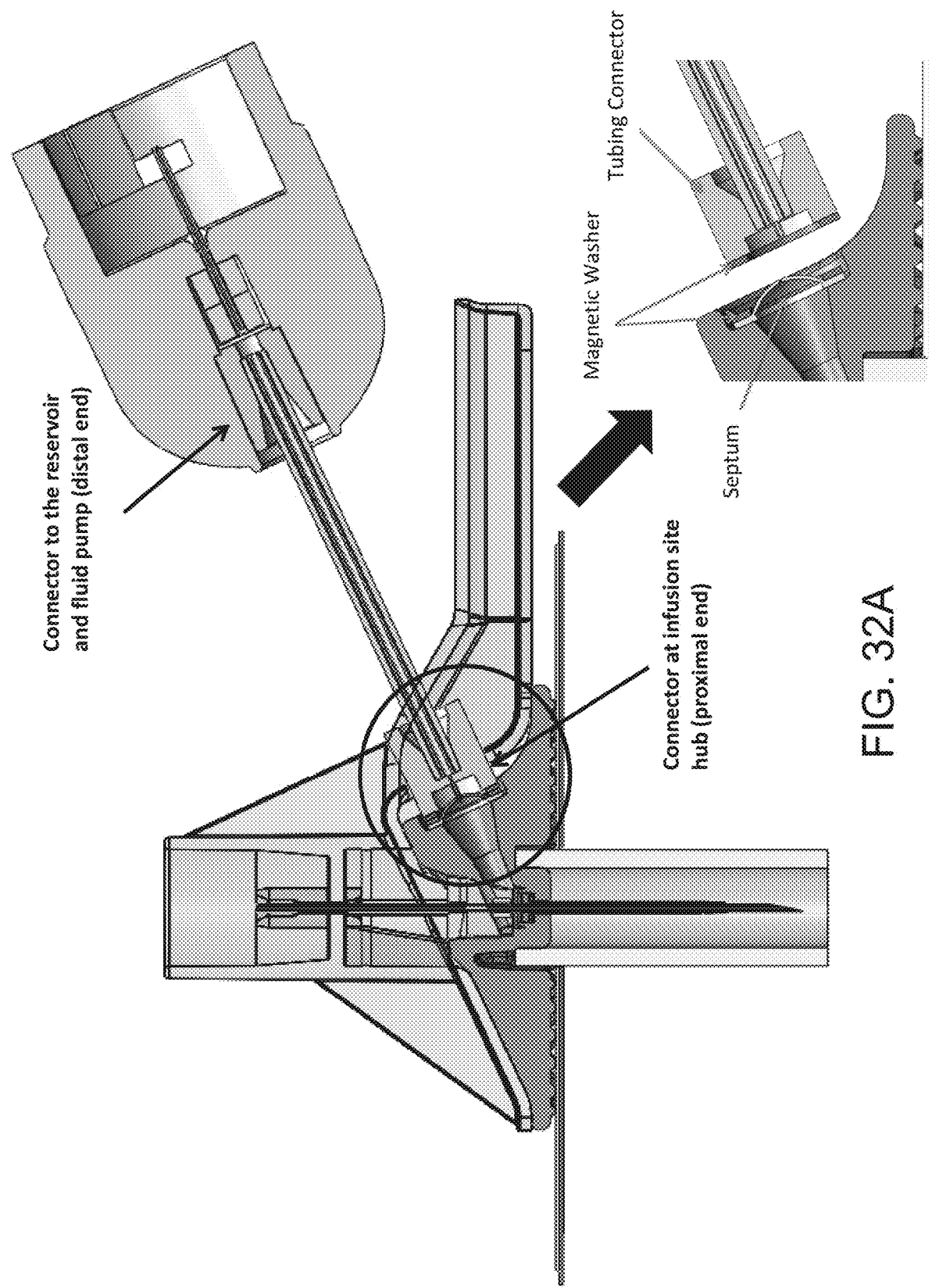
Figure 32B:
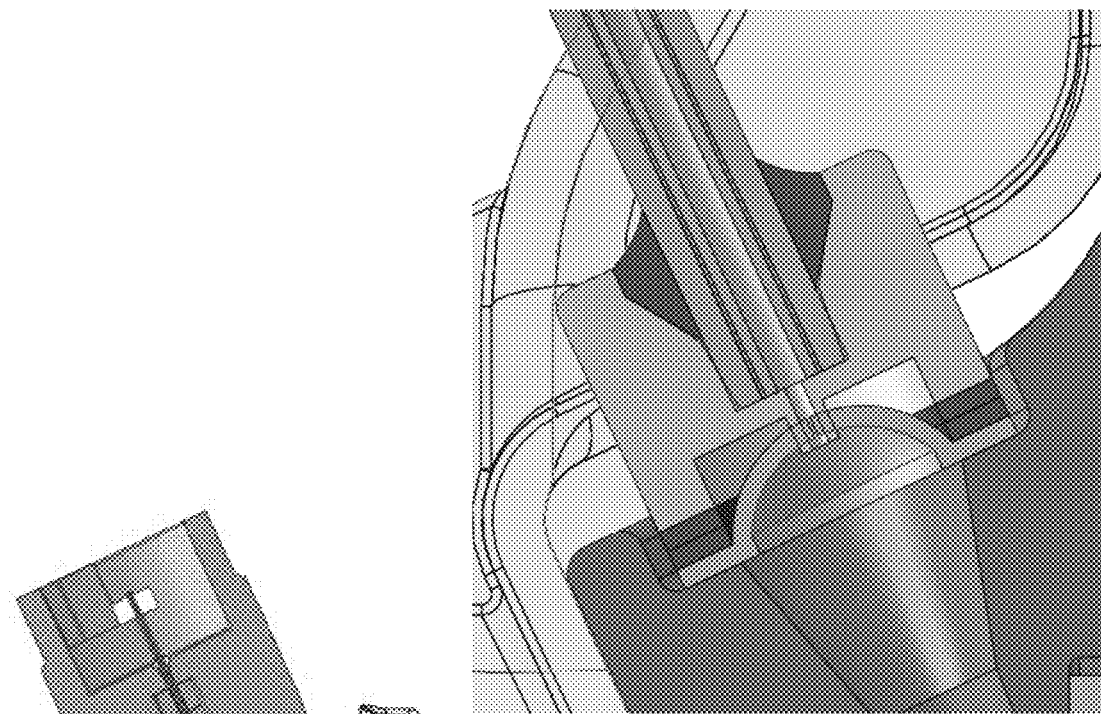
Figure 32B:
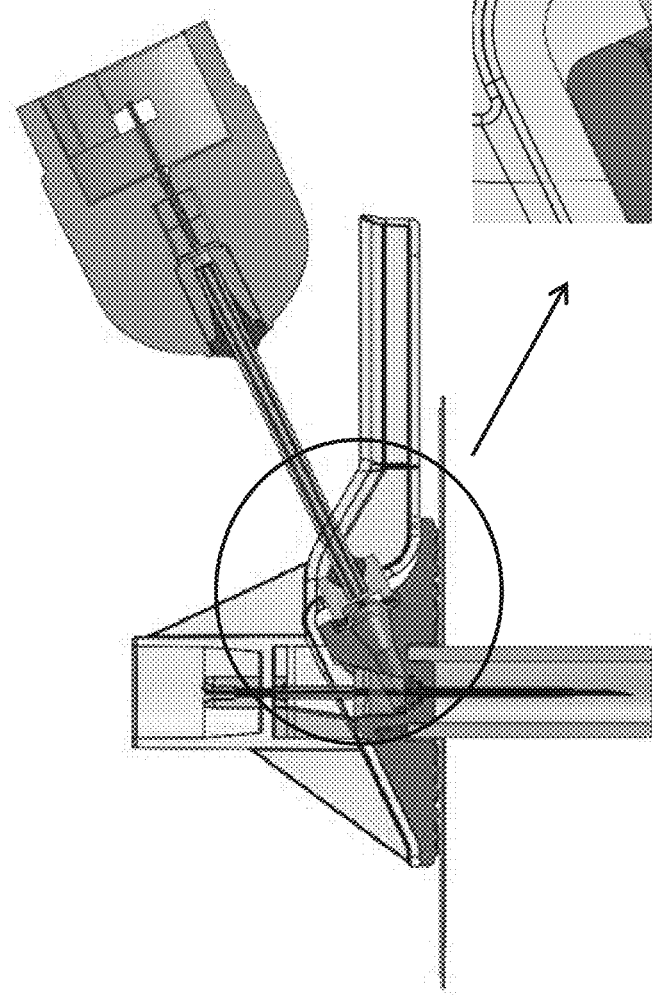
Figure 32C:
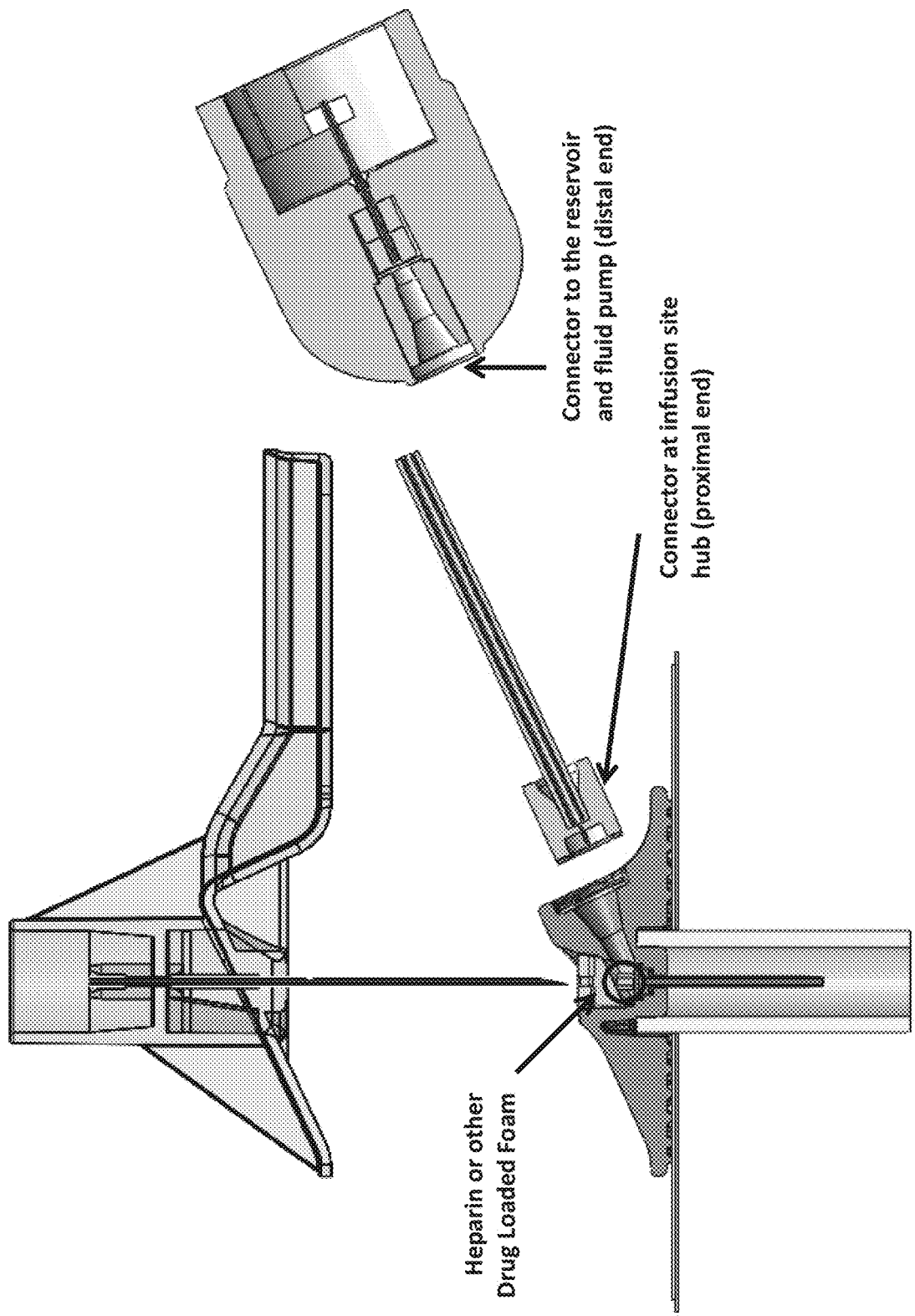
Figure 32D:
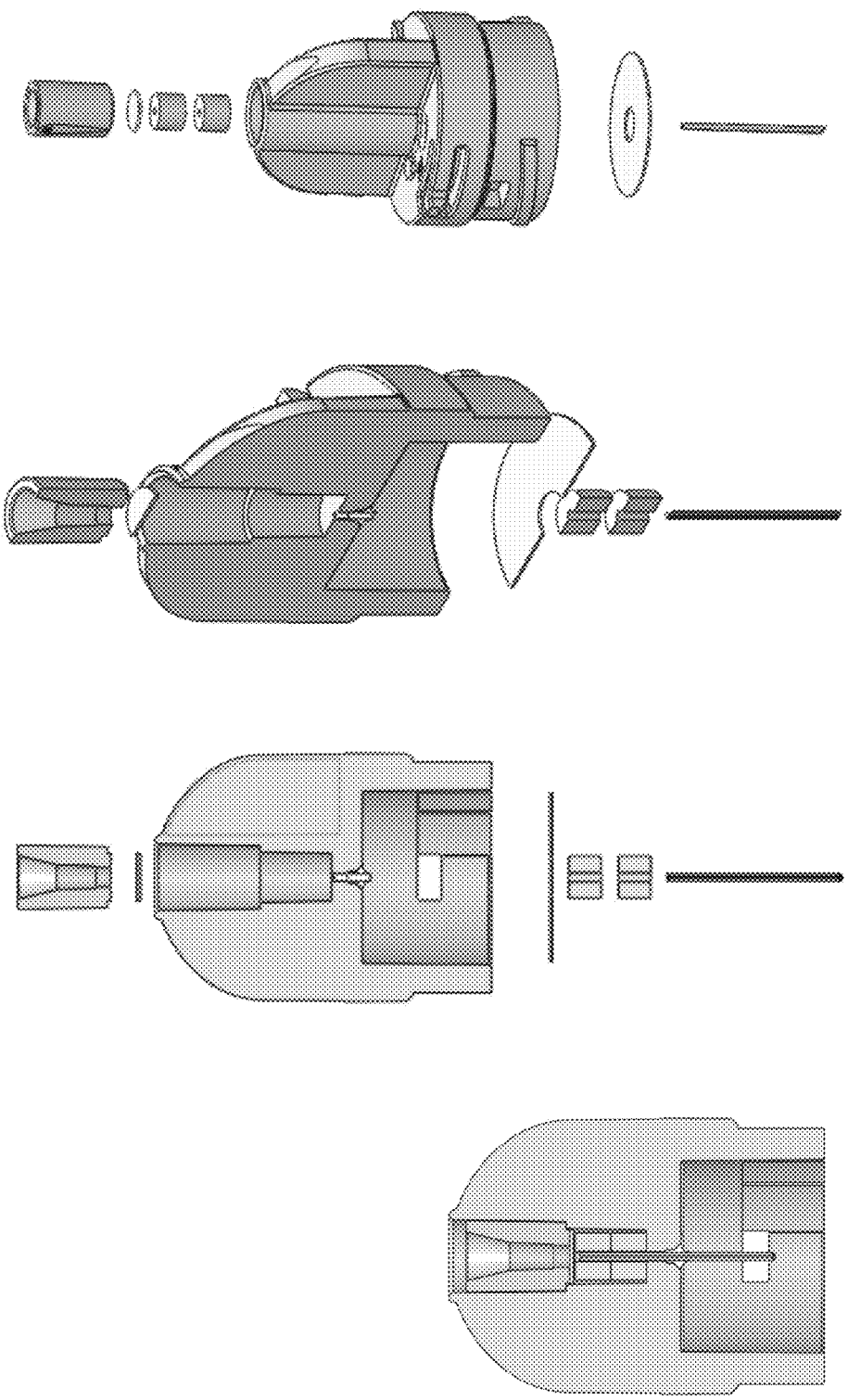
Figure 32F:
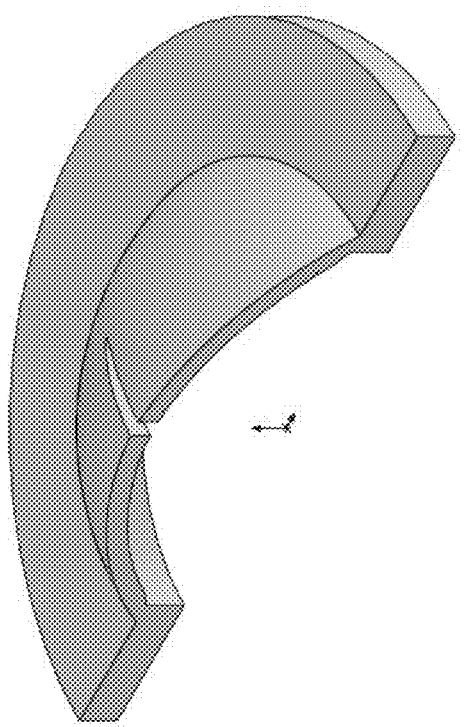
Figure 32F:
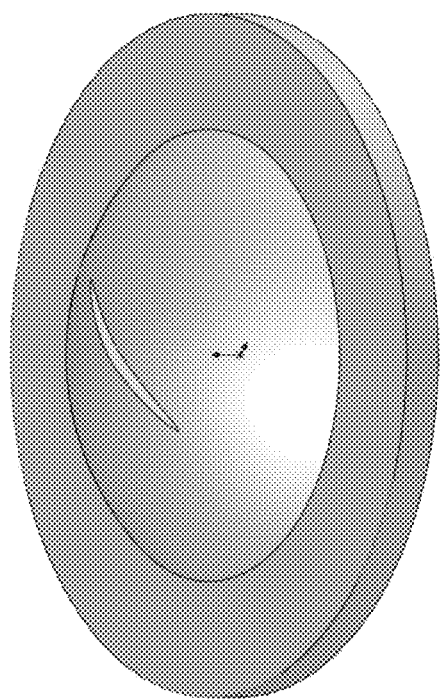
Figure 32G:
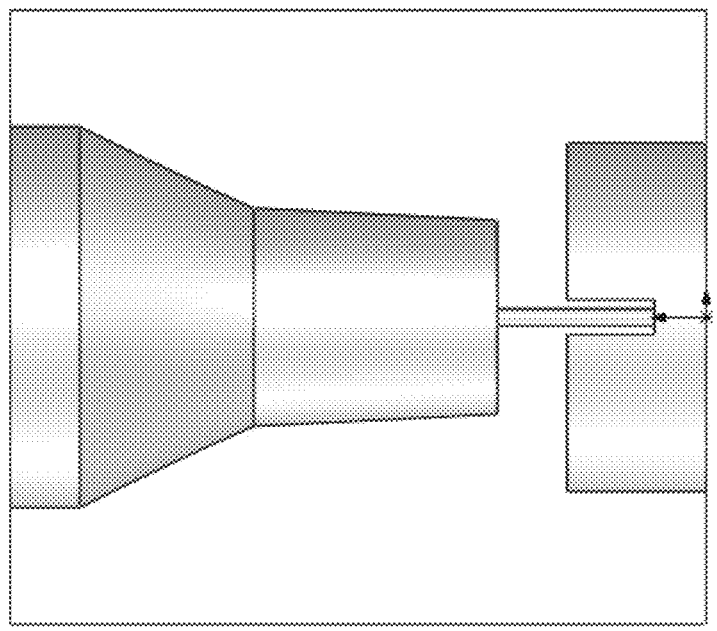
Figure 32G:
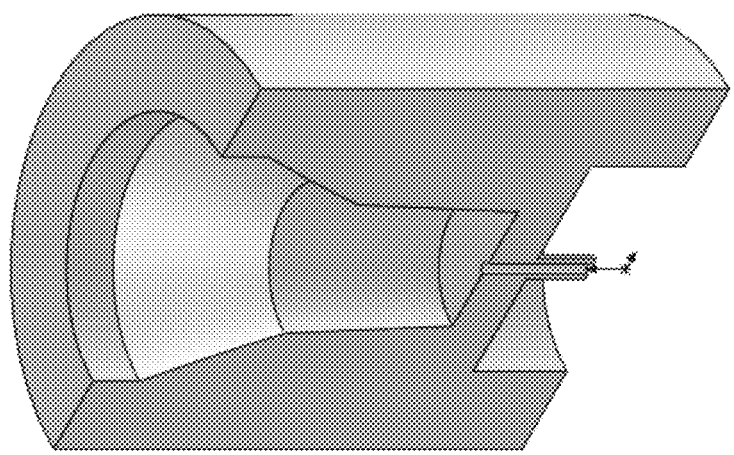
Figure 32H:
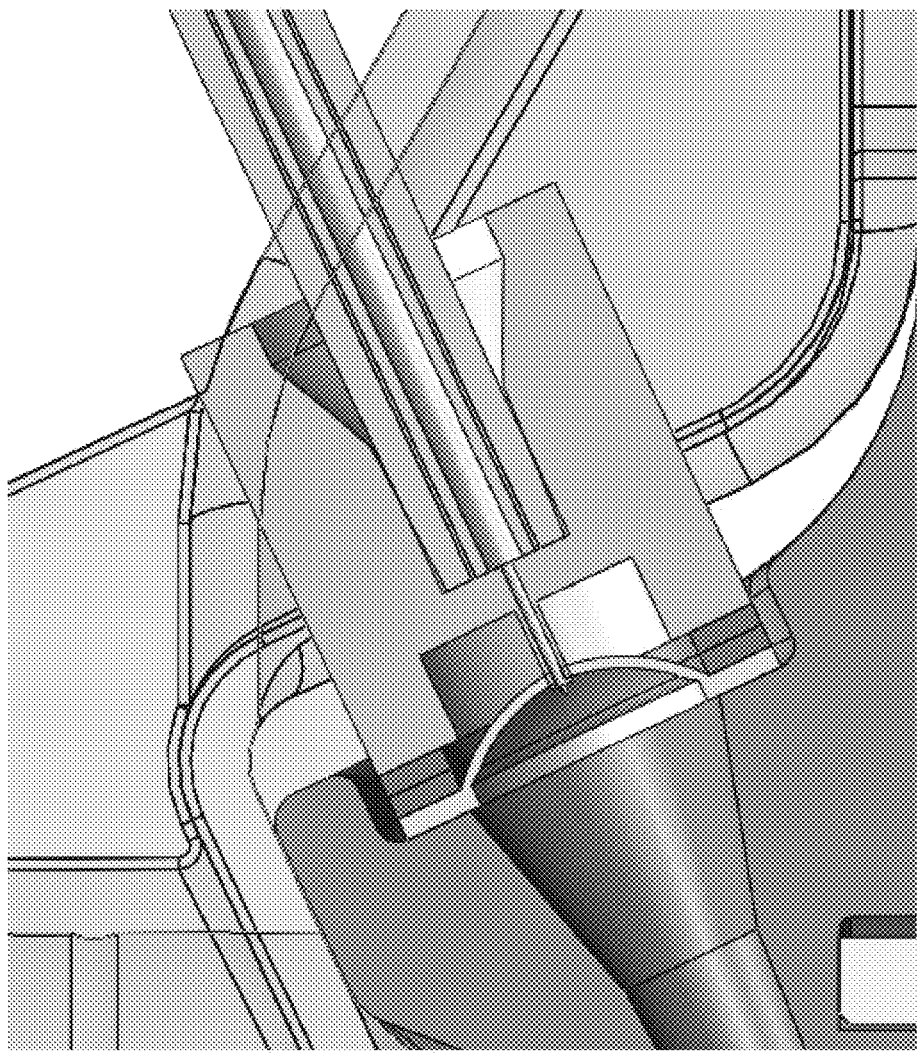

As shown by the exemplary embodiments found in FIGS. 30-32 (among others), tubing embodiments of the invention can further include connectors at the ends of the tubing to connect to other components within a system. For example, in some embodiments, one tubing connector connects to the reservoir and fluid pump (distal end), and the other tubing connector connects to the infusion site hub (proximal end). Unique features of these connectors have a number of benefits. For example, connectors to the reservoir and fluid pump (distal end) can comprise an H-cap connector design manufactured in one piece to improve the dexterity (i.e. no rigid surface and easy for tubing assembly) and reduce safety concern (i.e. remove the welding interface to eliminate the potential leakage). In addition, connectors at infusion site hub (proximal end) can comprise designed with magnetic washer at both tubing and infusion set Hub (see, e.g. FIGS. 30-32) for easy connect and disconnect. Tubing connectors designed to connect to an infusion site hub (proximal end) can comprise loaded with Heparin or other drug loaded foam. The infusion site Hub can also be loaded with Heparin or other drug loaded foam (see, e.g. FIGS. 30-32) to improve infusion site viability. By separating the tubing from the infusion site hub and using a magnetic washer and septum for site connection, patients will have the freedom to utilize their preferred infusion components (hubs or different length of the tubing).

Embodiments of the invention include an Infusion Site Hub with drug preloaded foam and tubing connector interface (see, e.g. FIGS. 30-32). This Hub can be loaded with or without drug, depending on the therapy needs. The Hub can be used by connecting to infusion set for pump therapy or by itself for insulin pen injection for MDI. This design provides usage versatility and Infusion Site (Hub) designs can be tailored to meet patients' needs (different body BMI). In addition, to enhance compatibility with approved 6-day continuous glucose sensor, it is in the patient's best interest to produce the infusion set with at least a 6-day shelf life (vs. currently 3-day use) to align with the sensor capability for convenient use and for a future closed-loop system. Therefore, the utility of the invention is a desirable solution to avoid tubing kinking and to prevent the preservative loss and to ensure insulin stability that would allow patients to use the infusion set for an extended period of time. Furthermore, by separating the tubing from the infusion site hub, patients will have the freedom to utilize preferred infusion components (hubs or different length of the tubing) and they will have more opportunity to explore and use optimal Infusion Site (Hub) designs.

Figure 34:
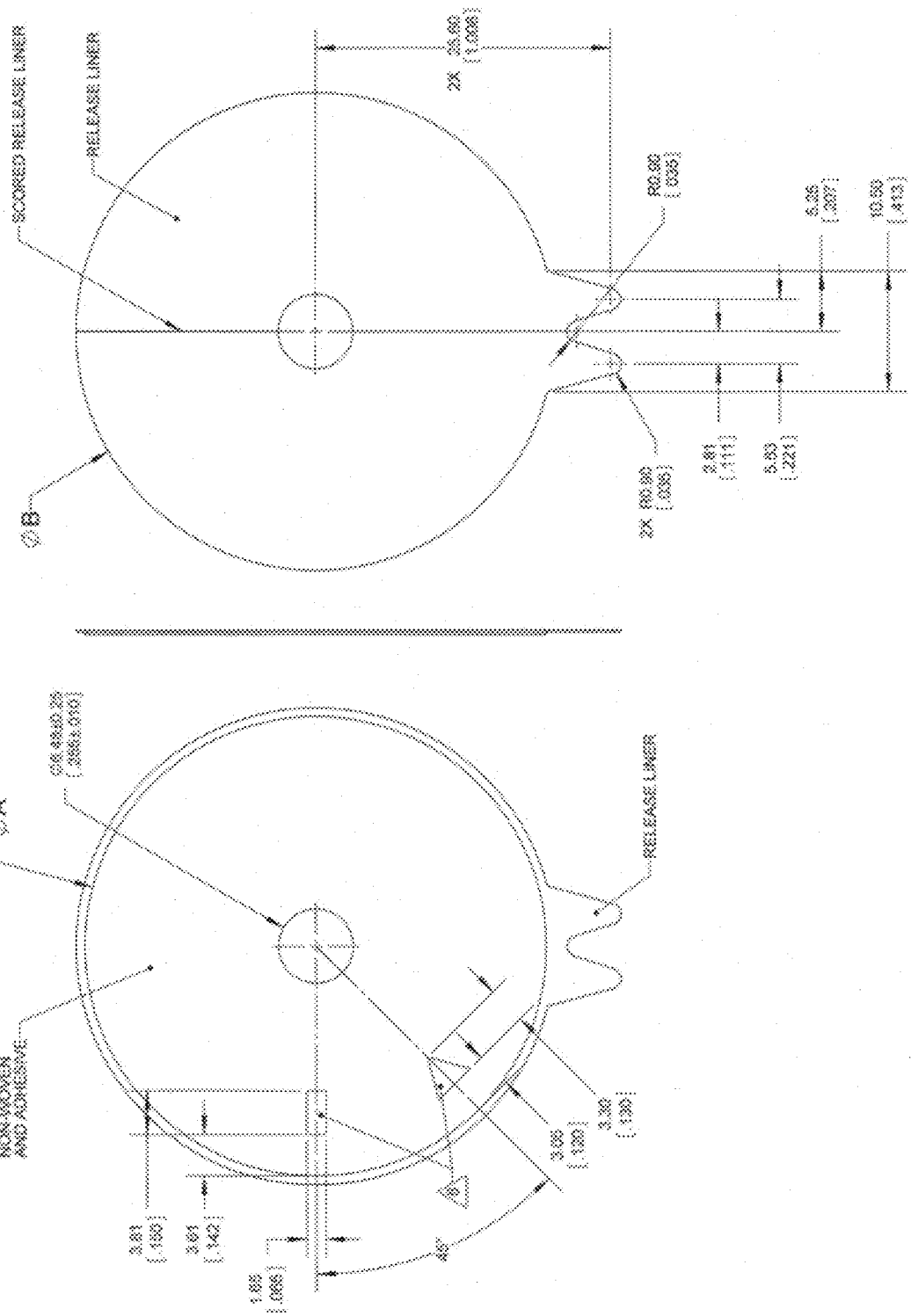
FIG. 34 shows views of an adhesive patch that can be used in embodiments of the invention.
Figure 35A:
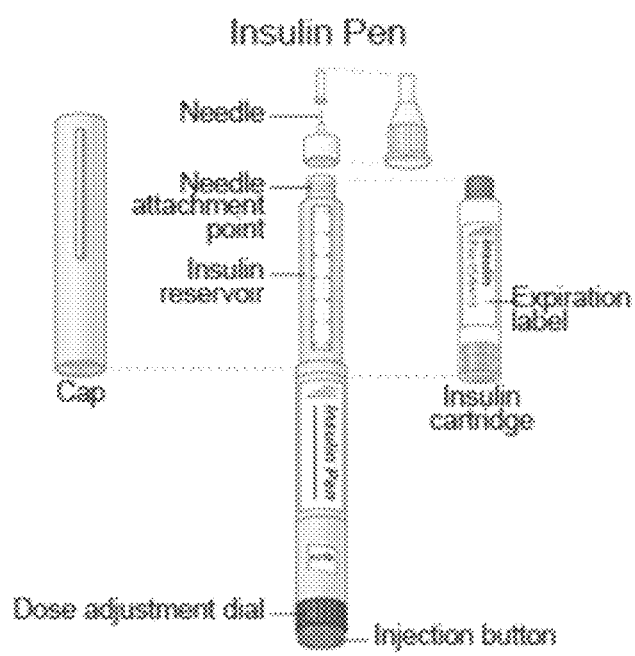
FIG. 35A shows a schematic of insulin pen components useful in embodiments of the invention.
Figure 35B:
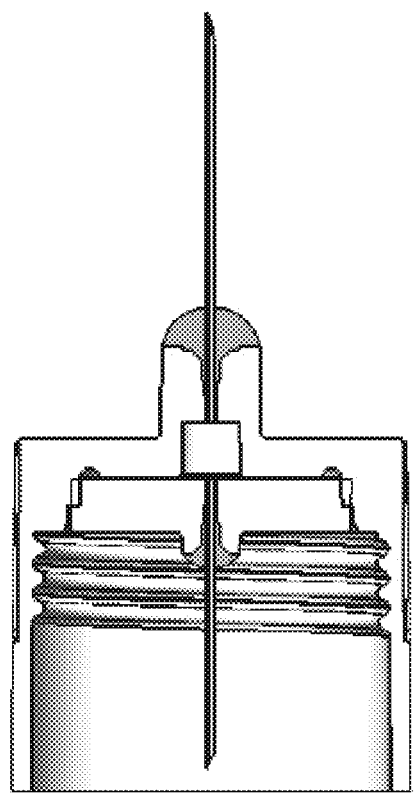
FIG. 35B shows a first schematic of insulin pen needle hub embodiments of the invention.
Figure 35C:
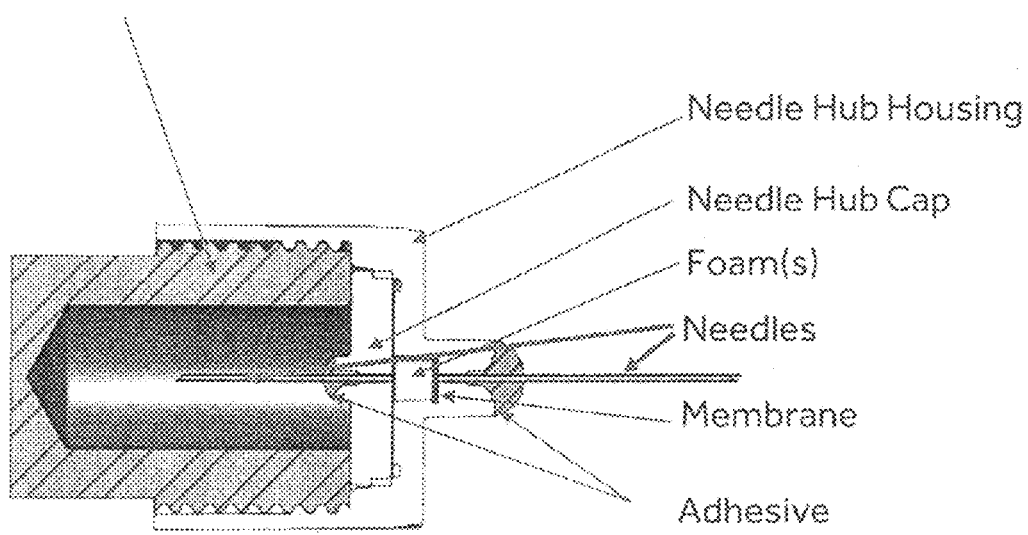
FIG. 35C shows a second schematic of insulin pen needle hub embodiments of the invention.
Figure 36:
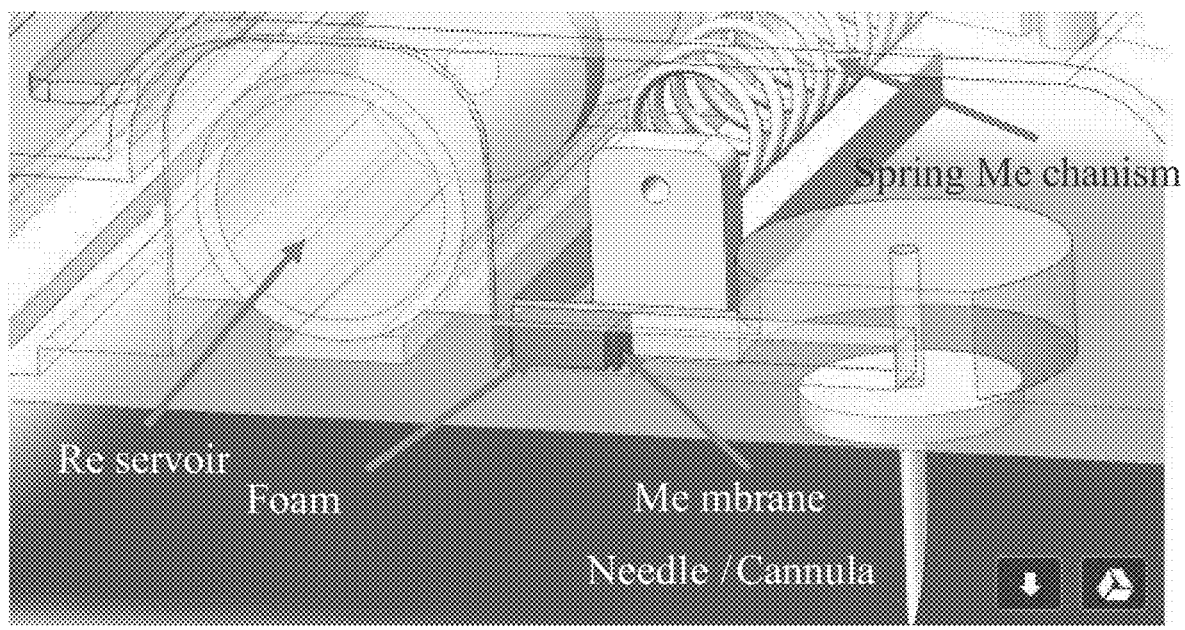
FIG. 36 shows a schematic of insulin infusion pump embodiment components of the invention.

Embodiments of the invention include a transdermal patch designed for use with the above-noted tubing and/or connector and/or hub embodiments. Typically, the transdermal patch contains a plurality of layered materials (e.g. an adhesive layer) and a movable liner. A backing layer is typically made of nonwoven polyurethane (PU) having a high moisture vapor transmission rate (MVTR). In this context, the inherent hydrophobic property of materials such as polyurethane minimize adsorption of liquid from the outer backing layer through the nonwoven backing to the skin surface. The nonwoven backing layer can comprise a polyurethane film hysteresis for comfortable skin attachment. Typically, the nonwoven material is bi-elastic to facilitate the patch flexing with the skin substrate. The nonwoven backing layer construction from materials such as a polyurethane film minimizes skin irritation caused by edge fibers. Typically, the adhesive is an acrylic adhesive uniformly distributed over a layer of the patch. Typically, the patch includes a release layer, for example a silicon coated paper. In addition, all materials of the adhesive patch are selected to be compatible with ethylene oxide and irradiation sterilization. In some embodiments, an immune response inhibiting agent is coupled to the transdermal patch that secures the infusion set to the patient (e.g. one comprising a substrate, a response-inhibiting agent, and an adhesive layered on the substrate); and/or is disposed in a drug-coated septum within a reservoir of an insulin pump. An illustrative design for such patches is shown in FIG. 34. Embodiments of the invention further include Pre-filled the heparin/insulin solution in an injection pen. Embodiments of the invention further include a simplified (single use) patch pump—change weekly (e.g. with a heparin concentration 20 U/mL to 20,000 U/mL in the insulin formulation). The heparin can also be included in the foam/mesh insert for fluid-path drug load.

The systems and system components disclosed herein allow artisans to employ methods relating to the delivery of insulin to a patient in a manner that overcomes certain problems with conventional infusion systems. Embodiments of the invention include a method of increasing the amount of insulin ("insulin reservoir") in a subcutaneous space in which the insulin is being infused, by infusing insulin into the patient using a system or components disclosed above, wherein the system/components are designed to allow the delivery of heparin to the site at which the insulin is being infused (e.g. via a heparin impregnated matrix that contacts the insulin infusate). Optionally the heparin and insulin infusate are mixed together in situ (i.e. is not premixed). In certain embodiments of the invention designed to increase the amount of insulin in a subcutaneous space, the insulin infused is selected to be (slower acting) human insulin and not a (faster acting) insulin analog (e.g. LISPRO insulin). In certain embodiments of the invention, the infusate further comprises dextran. Some embodiments of the invention include the use of a protease inhibitor in an infusate. Other embodiments of the invention exclude the use of a protease inhibitor in an infusate. In typical embodiments of the invention designed to increase the amount of insulin within a subcutaneous space, the insulin is not infused rapidly, and is instead infused over a period of greater than 10, 15, 30, 60 or more minutes (e.g. via continuous subcutaneous infusion (CSII)).

Figure 7A:
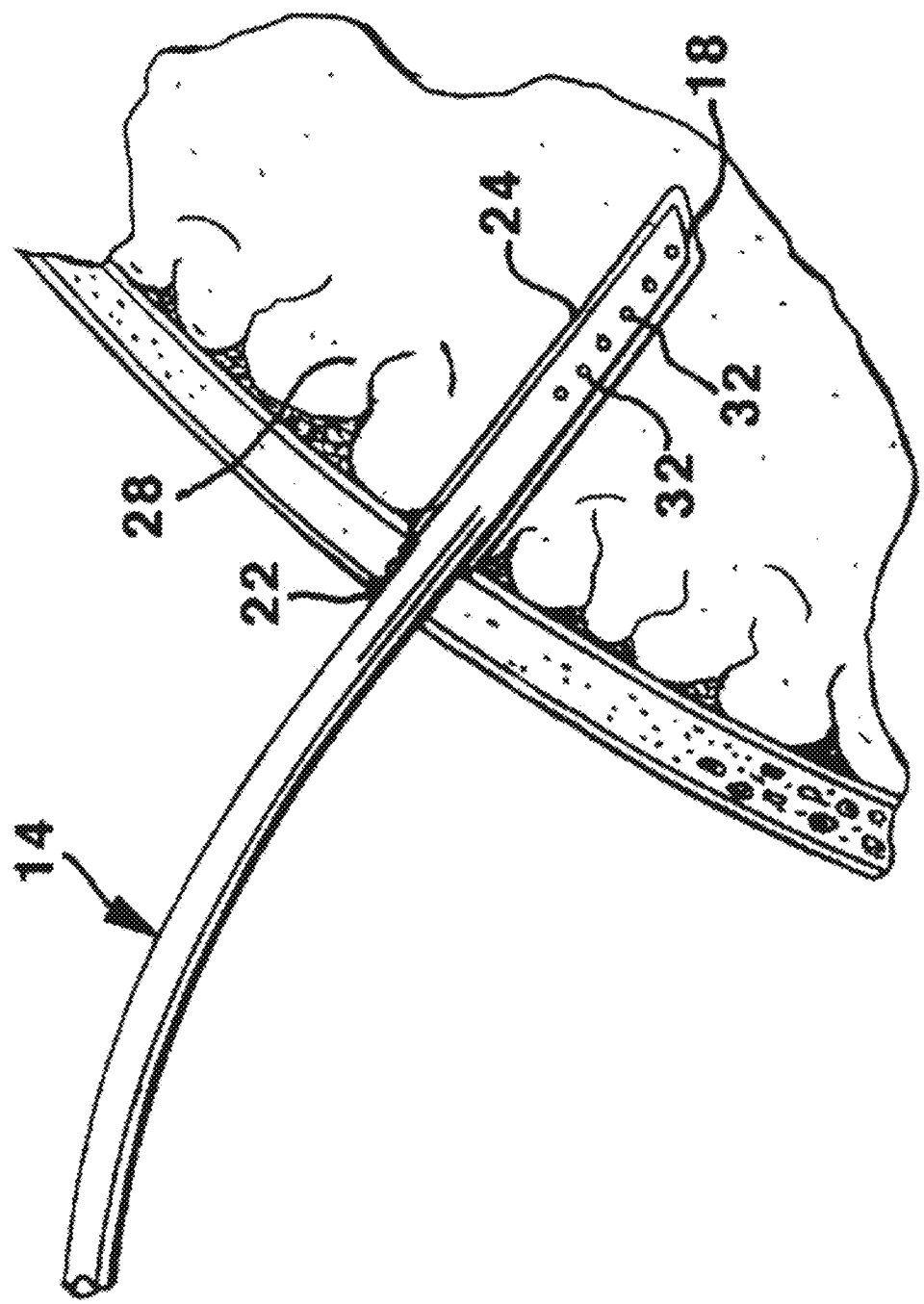
FIGS. 7A-D show an illustration of a cannula, in accordance with one or more embodiments of the invention.

FIG. 7A illustrates a means for conducting fluid to the human body employing a cannula in accordance with one embodiment of the present invention. Here, the distal end 18 of the cannula 14 is received in an opening 22 formed in a patient's tissue and in a bore 24 formed in the tissue 28. In this embodiment, multiple fluid apertures 32 are provided in the cannula adjacent to the distal end 18, whereby fluid medication such as insulin can be conducted directly to the bore 24 in the tissue.

As noted above, an inherent problem with the implantation of a foreign body in human tissue is the foreign-body response from the patient's immune system. An injury is created at the site where the needle is inserted into a patient's tissue for cannula placement and medication infusion (the "single site of infusion"). Catheter/cannula insertion induces an acute inflammatory reaction within epidermis, dermis, and subcutaneous adipose tissue. Another problem is that tissues and cells may be damaged during the insertion process. This includes possible damage to cells and connective tissue along the path of needle/catheter infusion, as well as damage to basement membranes, the extracellular matrix, and structural proteins. Damaged lymphatic vessels, arterioles, capillaries, and venuoles may also cause blood/fluid to accumulate around the catheter shaft (e.g. clotting). A further problem is that there may be physiological debris that forms around the catheter, obstructing capillaries.

Infusion site-loss and site-reduction occur in part due to the encapsulation of the cannula by the tissue. In such instances, insulin absorption into the patient's circulation becomes variable and unreliable over time. Causes of site-loss/reduction are poorly understood and may be due to localized tissue inflammation, coagulation, occlusion, and/or tissue proliferation. Moreover, although the materials used for the cannula are flexible enough to provide comfort for the patient, the inevitable movement of the cannula that occurs when a patient moves leads to further tissue inflammation. Thus, an implanted cannula (i.e. a foreign body) elicits an exacerbated host response as a result of any cannula movement.

Embodiments of the present invention include methods and devices for reducing a diabetic patient's foreign-body immune response, which is associated with the treatment of the diabetic patient where the treatment requires implantation of a foreign body. In particular instances, the invention mitigates infusion site-loss/occlusion caused by a short-term (e.g. 0 to 8 days) subcutaneous insertion of a cannula or catheter. The cannula or catheter is usually part of a subcutaneous infusion set and is attached to a reservoir or infusion pump intended to administer a fluid medication or drug formulation. As used herein, a response-inhibiting (and/or mitigating) agent refers to an active agent that inhibits, mitigates or reduces a foreign-body response of the patient's tissue (such as site-loss/occlusion of an inserted cannula).

As described in further detail below, various approaches are provided for inhibiting or mitigating site-loss/occlusion. A mechanical approach is provided that improves the mechanical design of the infusion set to mitigate injury to the insertion site. For example, the fluid path of infusion may be altered (side ports). In one or more embodiments, the cannula is modified with different structural configurations that incorporate holes and/or wells for loading one or more response-inhibiting agents (see Drug-coated cannula section below). A material approach is also provided that modifies the surface of the insertion cannula with anti-fouling biomaterials, such as PEG or immobilized heparin, to alleviate foreign body response. A drug approach is also provided that locally administers/releases response inhibiting agents, such as immuno-suppressants, anti-inflammatory agents or other bioactive molecules, to alleviate a body's response to the insertion of a cannula and insulin, improve local insulin absorption into blood stream, and/or prevent localized insulin. To address the issue of possible damage to connective tissue, anti-proliferative agents such as rapamycin may be used. To address the issue of possible blood/fluid accumulation or clotting, anti-coagulants such as heparin and dextransulfate may be used. To address the issue of physiological debris and obstruction of capillaries, a combination of anti-fouling and anti-coagulation agents may be used. Agents for breaking down hyaluronic acid may also be used. Other response-inhibiting agents that may also be used are described in the Response-Inhibiting Agents section below.

Insulin losses at a single site of infusion are frequent in diabetic patients and are a potential source of blood glucose variability. The physiological processes behind such site loss are complex, and unpredictable. For this reason, it is not possible to predict how a specific agent will affect site loss. For example, as disclosed in the examples below, formulations of insulin combined with anti-inflammatory agents heparin and/or dextran and/or rapamycin notably inhibited site loss, thereby extending the duration of cannula insertion, performing significantly better than the control. In contrast, formulations of insulin combined with anti-inflammatory agents betamethasone sodium phosphate (BSP) or Dexamethasone palmitate (DXP) actually resulted in the onset of site-loss much earlier, performing significantly worse than the control (as discussed in Example 6 below).

Embodiments of the invention include systems for delivering insulin to a diabetic patient at a single site of infusion over a period of time (e.g. at least 7, 8 or 9 days). Typically these systems include a medication reservoir comprising an insulin solution, a cannula adapted for subcutaneous insertion into a tissue of a diabetic patient at the single site of infusion, and a fluid conduit in operable contact with the medication reservoir and the cannula, and adapted to deliver insulin from the medication reservoir to the single site of infusion. Such systems further include a site loss mitigating agent that inhibits at least one of: coagulation at the single site of infusion, inflammation at the single site of infusion, and encapsulation of the cannula at the single site of infusion. These systems are useful, for example, in methods for delivering insulin to a diabetic patient at a single site of infusion over a period of at least three or more (e.g. seven) days. These systems are also useful in methods for inhibiting a foreign body response in a diabetic patient receiving insulin at a single infusion site over a time period of at least three or more days.

In some of the working embodiments of the invention that are disclosed herein, the site loss mitigating agent comprises a heparin composition. This heparin composition can be disposed at a number of different locations within these systems. In certain embodiments, the heparin (or other agent) is disposed within a depot and adapted to contact the insulin solution as the insulin solution flows from the medication reservoir to the single site of infusion. For example, in some embodiments of the invention, the depot includes a sponge, membrane or a filter impregnated with heparin that moves into the insulin solution upon contact. In some of the working embodiments disclosed herein, the heparin (or other agent) is disposed within a composition that coats the cannula. Site loss mitigating agents can be disposed at a number of other locations and, for example, can coat a septum within the medication reservoir, or be disposed within a transdermal patch etc.

In some embodiments of the invention, the heparin is administered to the patient in an amount between 40 U/device to 8000 U/device and at a dose of 0.1 to 80 U/kg/day. Optionally, the heparin is administered to the patient in an amount between 0.5 and 5 U/kg/day. In certain embodiments of the invention, the system delivers heparin according to a specific delivery profile. For example, embodiments of the invention include systems designed to deliver an immediate release profile, one where the majority of the heparin is administered to the patient from 0 to 6 hours following insertion of the cannula. Other embodiments of the invention include an extended release profile, one where the heparin is administered to the patient for at least 24 or 48 hours following insertion of the cannula. In some embodiments of the invention, the system is designed to deliver at least 50% of the total heparin administered in the first three days following insertion of the cannula.

Embodiments of the invention can further include dextran sulfate compositions, for example a dextran composition adapted to contact the insulin solution as the insulin solution flows from the medication reservoir to the single site of infusion. In typical embodiments of the invention, the dextran is administered to the patient in an amount between 0.002 and 0.4 mg/kg/day. In some embodiments of the invention, the dextran is administered to the patient in an amount between 0.005 and 0.015 mg/kg/day. In some embodiments of the invention designed to administer heparin and dextran, the heparin coats the cannula and the dextran is disposed in the depot. Embodiments of the invention can further include additional agents such as sirolimus, tacrolimus, or combination thereof. In some embodiments of the invention, the response-inhibiting agent is combined with insulin in the medication reservoir.

Other embodiments of the invention include methods for delivering insulin to a diabetic patient at a single site of infusion over a period of time (e.g. at least three or at least seven days), the method comprising infusing the insulin at the single site of infusion using a system as disclosed herein. Typically in these methods, the system that delivers insulin to the diabetic patient comprises a medication reservoir comprising an insulin solution, a cannula adapted for subcutaneous insertion into a tissue of a diabetic patient at the single site of infusion, a fluid conduit in operable contact with the medication reservoir and the cannula and adapted to deliver insulin from the medication reservoir to the single site of infusion, and a site loss mitigating agent that inhibits at least one of: coagulation at the single site of infusion, inflammation at the single site of infusion, and encapsulation of the cannula at the single site of infusion.

Figure 11:
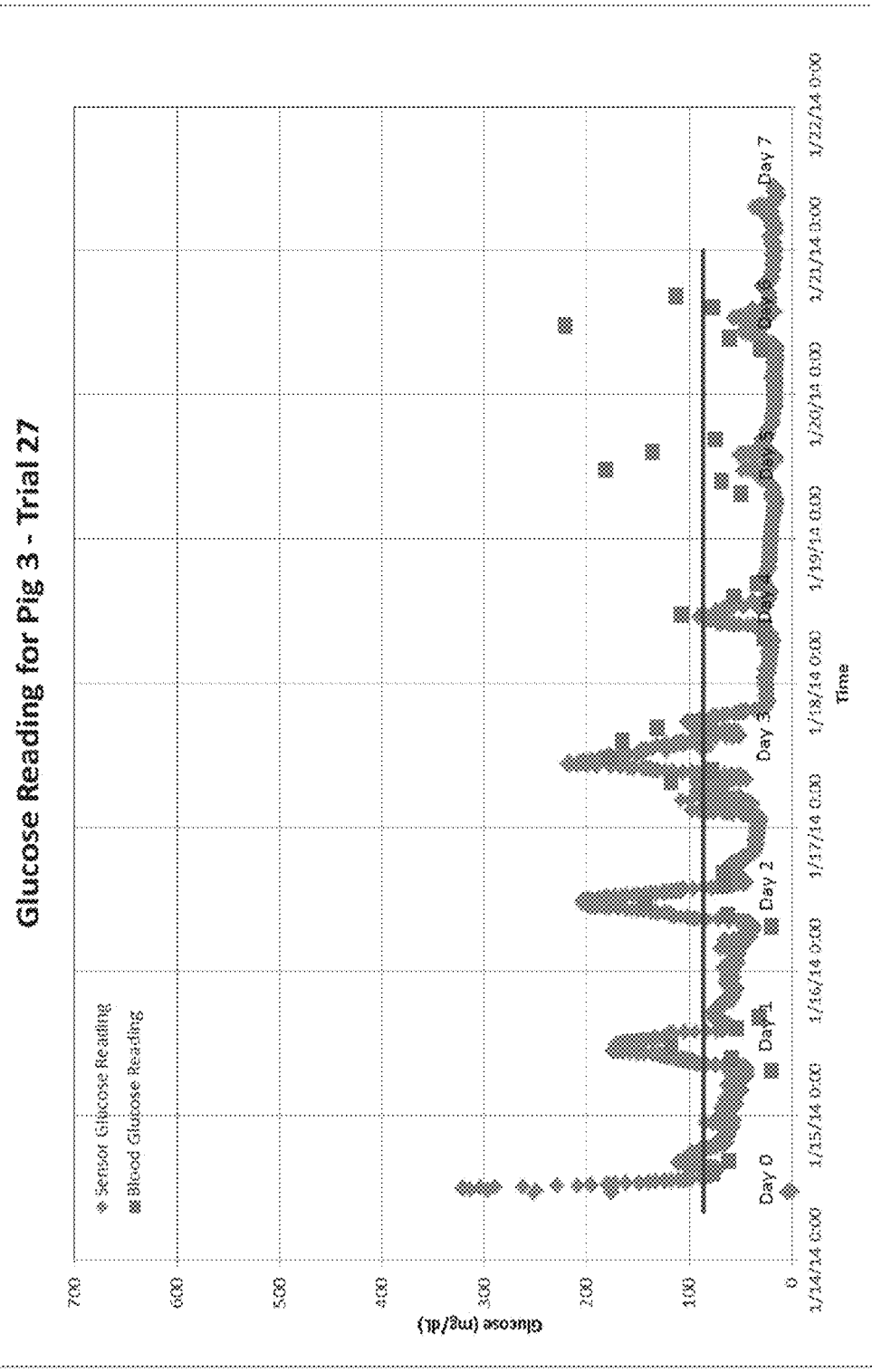
FIG. 11 is a graph of the glucose monitoring results for pig IM3, which shows that no site-loss occurred in 6 days.
Figure 12:
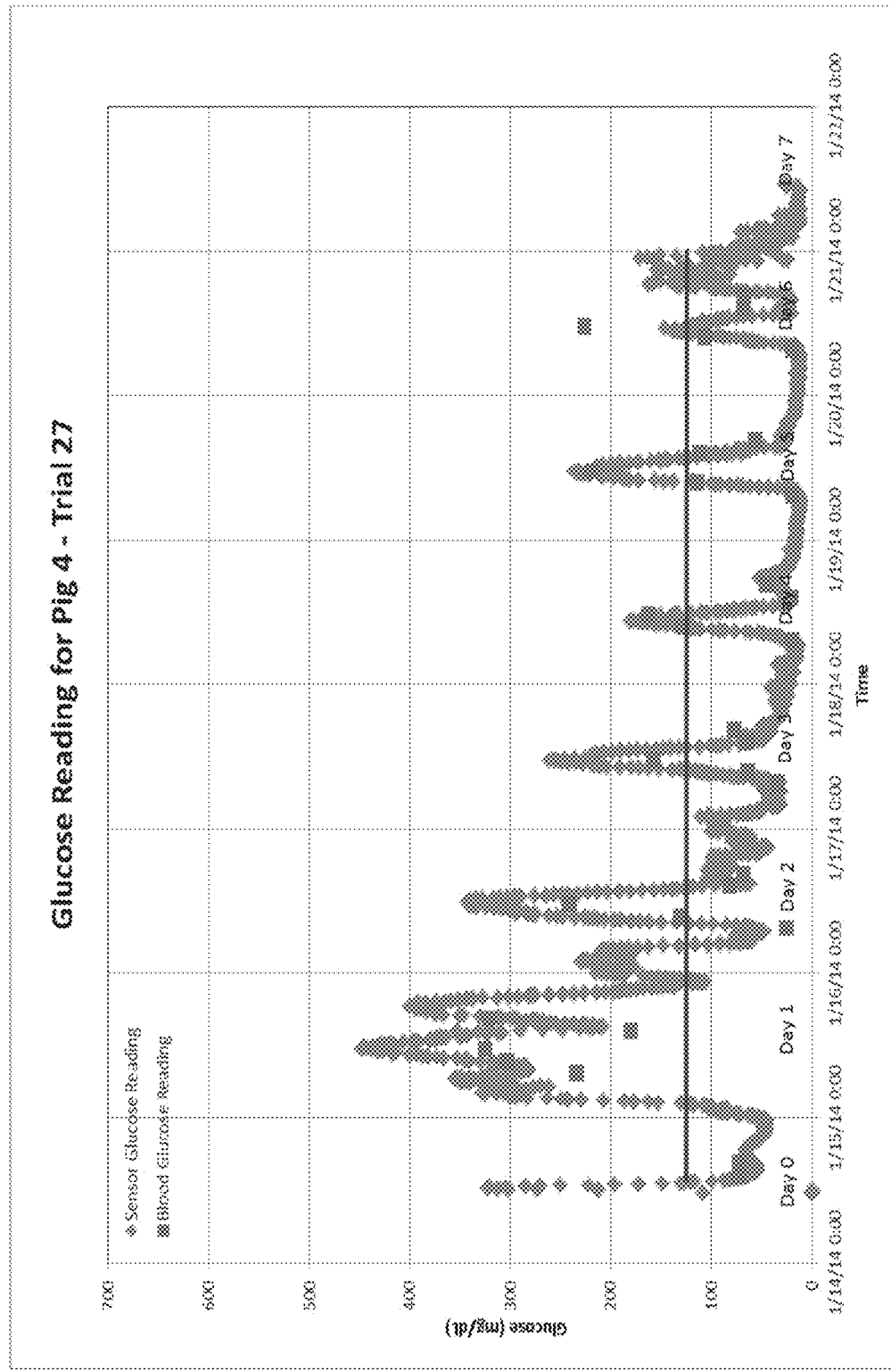
FIG. 12 is a graph of the glucose monitoring results for pig IM4, which shows that no site-loss occurred in 6 days.

In some embodiments of the invention, the response-inhibiting agent is heparin. Heparin is well known in the art and pharmaceutical grade heparin useful in embodiments of the invention is readily available from a wide variety of sources (e.g. Heparin Sodium INJ available from Celsus and Pfizer). The source of the heparin sodium in the working embodiments of the invention that are disclosed herein was Fisher BioReagents. In typical embodiments of the invention, the heparin and is administered at a concentration range of 40 U/ml to 8000 U/ml or 0.1 mg/ml to 20 mg/ml. In some embodiments, the heparin is administered at a dose of 0.1 to 80 U/kg/day. In specific instances, the heparin is administered at a concentration of 800 U/ml and/or at a dose of 8 U/kg/day. Data from working embodiments of the invention where heparin is used as a response-inhibiting agent is discussed in the Examples below (e.g. Example 7) and shown in the Figure (e.g. FIGS. 11 and 12). These finding are unexpected in view of art that teaches that heparin is no better that a sodium chloride solution for maintenance of patency in peripheral intermittent intravenous devices (see, e.g. Tuten et al., Appl Nurs Res 1991 4(2): 63-72).

In certain embodiments of the invention, a response-inhibiting agent comprises dextran (e.g. alone or in combination with another agent such as heparin). Typically dextran that is administered to the patient in an amount between 0.002 and 0.4 mg/kg/day. Dextrans are well known in the art and pharmaceutical grade dextran useful in embodiments of the invention is readily available from a wide variety of sources (e.g. Dextran 70 pharmaceutical grade available from Sinus Biochemistry and Electrophoresis GmbH). The source of the dextran in the working embodiments was Dextran Sulfate Sodium Salt from Sigma-Aldrich. Data from working embodiments of the invention where dextran is used as a response-inhibiting agent is discussed in the Examples below (e.g. Example 9) and shown in the Figure (e.g. FIG. 22).

In certain embodiments of the invention, a response-inhibiting agent comprises rapamycin (e.g. alone or in combination with another agent such as heparin). Rapamycin is well known in the art and pharmaceutical grade rapamycin useful in embodiments of the invention is readily available from a wide variety of sources (e.g. Rapamune available from Wyeth Pharmaceuticals Company, a subsidiary of Pfizer Inc). In some embodiments, a response-inhibiting agent is rapamycin and is administered (either formulated, co-infused or coated) at a dose of 0.5-10 μg/device at 0.02 to 1.5 μg/day. The source of the rapamycin in the working embodiments was TSZCHEM. Data from working embodiments of the invention where rapamycin is used as a response-inhibiting agent is discussed in the Example below (e.g. Example 10).

In one or more embodiments of the invention, the response-inhibiting agent is provided in a depot in operable contact with section of the fluid conduit of the infusion cannula. In one or more other embodiments of the invention, the response-inhibiting agent is provided as a coating that coats a part of the infusion set or reservoir. In certain embodiments, the response-inhibiting agent is disposed on a cannula and/or a transdermal patch that secures the infusion set to the patient and/or a drug-coated septum within a reservoir of an insulin pump. In one or more other embodiments of the invention, the response-inhibiting agent is provided in a reservoir where the response-inhibiting agent is present in the infusate. In certain embodiments, the response-inhibiting agent is pre-mixed with the medication prior to infusion into a patient. In other embodiments, the response-inhibiting agent and medication are delivered from two different reservoirs and then mixed in-situ upon infusion.

Optionally an agent such as heparin is disposed within a depot and adapted to contact the insulin solution as the insulin solution flows from the medication reservoir to the single site of infusion and/or within a composition that coats the cannula and is administered according to a specific delivery profile. For example, the agent can be administered according to an immediate release profile wherein the heparin is administered to the patient from 0 to 6 hours following insertion of the cannula. Alternatively, the agent can be administered according to an extended release profile wherein the response-inhibiting agent is administered to the patient for at least 48 hours following insertion of the cannula.

Another embodiment of the invention is a method of facilitating delivery of insulin to a diabetic patient over a period of time at a single infusion site. In such embodiments, the method comprises inserting a cannula subcutaneously into a tissue of a diabetic patient at an insertion site and administering a response-inhibiting agent to the patient at the site of cannula insertion, wherein the response-inhibiting agent inhibits a foreign-body response of the patient's tissue (such as site-loss/occlusion of the cannula). In this way, the method facilitates the delivery of insulin to the diabetic patient over a period of time (e.g. at least 6, 7, 8, 9, 10, 11 or 12 days). In an illustrative embodiment of the invention, a method for reducing a foreign body response in a diabetic patient is provided, the method comprising inserting a drug-coated cannula subcutaneously into a tissue of a diabetic patient at an insertion site, the drug-coated cannula having an exterior surface coated with a response-inhibiting agent. Optionally the tip of the cannula is coated. The exterior surface of the drug-coated cannula can comprise a hole, well, groove, pore, indentation or combination thereof, and the response-inhibiting agent is at least partially contained within at least a portion of the hole, well, groove, pore, indentation or combination thereof.

Related embodiments of the invention include methods for inhibiting a foreign body response in a diabetic patient receiving insulin at a single infusion site over a time period of at least 3, 4, 5, 6, 7, 8, 9, 10, 11 or 12 days, the method comprising administering a site loss mitigating agent in combination with insulin at the single infusion site, wherein the site loss mitigating agent inhibits at least one of: coagulation at the single infusion site, inflammation at the single infusion site, and encapsulation of the cannula at the single infusion site, thereby inhibiting a foreign body response in a diabetic patient. Optionally, the site loss mitigating agent is heparin administered at a concentration range of 40 U/ml to 8000 U/ml or 0.1 mg/ml to 20 mg/ml. In certain embodiments of the invention, the response-inhibiting agent is disposed in a depot adapted to contact an insulin solution as the insulin solution flows from a medication reservoir to the single infusion site. In some embodiments, the response inhibiting agent is disposed on the cannula and/or is disposed in a transdermal patch that secures the infusion set to the patient (e.g. one comprising a substrate, a response-inhibiting agent, and an adhesive layered on the substrate); and/or is disposed in a drug-coated septum within a reservoir of an insulin pump. These methods can include administering additional agents such as sirolimus, tacrolimus, or combination thereof.

Another embodiment of the invention is a method comprising the steps of providing an infusion catheter, compounding a response-inhibiting agent disposed within a polymeric material, and incorporating the compound with the catheter in a manner whereby the response-inhibiting agent will be leached from the polymeric material when the catheter is in fluid contact with bodily tissue. The catheter is inserted into a body of a diabetic patient with at least a portion of the catheter disposed adjacent to bodily tissue and fluid medication is conducted through the catheter to the tissue, wherein a foreign body response of the body tissue adjacent to the catheter is reduced by the introduction of a response-inhibiting agent. In yet another embodiment of the invention, a drug infusion set as described herein is combined with a continuous glucose monitoring device on the same adhesive patch (i.e. "combo-set"). A response-inhibiting agent is administered along with the insulin to the patient. In this way, the combo-set delivers insulin and monitors glucose levels in the patient for at least 6, 7, 8, 9, 10, 11 or 12 days.

In a further aspect, a method for reducing a foreign body response in a diabetic patient is provided comprising applying a drug-coated septum patch to a fluid path of an insulin pump. The drug-coated septum patch is located within a reservoir of the insulin pump and comprises a response-inhibiting agent. The response-inhibiting agent is released into a medication flowing through the fluid path of the insulin pump. An anti-inflammatory agent may also be included with the response-inhibiting agent. The anti-inflammatory agent may be heparin, rapamycin (sirolimus), betamethasone sodium phosphate, dexamethasone sodium phosphate, beclomethasone dipropionate, tacrolimus, or combination thereof.

Embodiments of the invention include methods of facilitating delivery of insulin to a diabetic patient at a single infusion/insertion site at during a period of infusion that occurs at least 5 days following the initial insertion of a catheter and sensor combo-set, for example, facilitating delivery of insulin at day 2, 3, 4, 5, 6, 7, 8, 9, 10, 11 or 12 (or at days 6-12 etc.) at a single infusion site using a combo-set. In this embodiment, the method comprises inserting a cannula and a sensor subcutaneously into a tissue of a diabetic patient at an insertion site, and administering a response-inhibiting agent to the patient at the site of cannula insertion, wherein the response-inhibiting agent inhibits a foreign-body response of the patient's tissue such as site-loss/occlusion of the cannula. In this way the method facilitates delivery of insulin to the diabetic patient at day 4, and/or 5 and/or 6 and/or 7 and/or 8 and/or 9 and/or 10 and/or 11 and/or 12.

Embodiments of the invention can be incorporated into the extended wear feature into any patch insulin pump thereby improving infusion site viability and extending the labelling of wear for more than 3 days (e.g. 4, 5, 6, 7, 8 or 9 days). Patch pumps avoid the tethered approach of conventional insulin pumps. Instead of having the pump connected to the body via an infusion set and tubing, the patch pump is worn directly on the body, discreetly attached at the infusion site through a cannula insertion. Upon insertion into a patient, the cannula provides passageways for continuously delivering the medication to the patient for some period of time (e.g. 3 days). A persistent problem associated with an implanted cannula (including plastic catheter or metal needle) is that the human body spontaneously reacts against foreign bodies. Among the various responses of a body to foreign bodies, inflammation and the build-up of fibrous tissue at the cannula infusion site significantly shortens the duration of patch pump wears. Moreover, tissue encapsulation and blockage of the inserted cannula (i.e. "occlusion") often occurs, thereby impeding or halting infusion of insulin. Thus, frequent re-positioning of the patch pump is required. Embodiments of the invention disclosed herein are designed to address problems associated with such phenomena in patch pumps by using systems and methods that utilize agents identified (membrane/foam or drug loaded foam) as having an ability to inhibit foreign body responses at a cannula insertion site, thereby inhibiting such problematic phenomena.

Embodiments of such devices include a membrane and a foam (can be loaded with or without drug, depending on the therapy needs) that can be incorporated into any of the Patch Insulin Pump cannula insertion ports or fluid path system. For example, the cannula insertion port can be modified with different structural configurations to load the membrane and foam, Heparin or other drug loaded foam to improve infusion site viability.

The depot components include the Polyvinyl Alcohol (PVA) foams disclosed herein. The foams are useful to remove the insulin aggregates and impurities that can be caused by environmental impact hence to maintain the insulin's stability and reduce the incidence of inflammatory reactions cause by Description: Polyvinyl Alcohol (PVA) foam, pore size ranging from 0.3 mm to 1 mm PVA foam has interconnected hollow cells and above 90% of volume is air.

Open pores are connected three dimensionally to connect each cells to continuous ones. This physical structure is the most remarkable feature of air-foam PVA therefore it can deliver various functions.

Embodiments of the Polyvinyl Alcohol (PVA) foams are as follow:

| | |
|---|---|
| Density (Dry) | 0.8-1.54 gm/cu.in. |
| Tensile Strength | 1.05 Kgm/cm2 |
| Tensile Elongation (Wet) | Greater than 100% or 100% min |
| Liquid Retention | 10-25 times sponge weight (H2O) |
| Porosity | 90-95% |
| Absorption (Aqueous) | 3-30 seconds |
| Elongation (Wet) | 100% min. |
| Pore Size (Average) | 0.3-1 mm (SEM) |
| Open Cell Volume | 90-95% |
| Color Pure White | |
| Thermal Stability | up to 57° C. (140° F.) |

The utility of the invention is a desirable solution to avoid site loss due to cannula insertion caused foreign bodies response to allow patients to use the Patch Pump safely during the CSII therapy.

Embodiments of the invention provide many advantages, such as increased patient safety by reducing the site-loss phenomenon, and in particular, reducing hyperglycemic events for diabetic patients. Since the invention provides an infusion set that may be used longer than currently recommended durations of 2-3 days, there is also increased comfort and convenience for the patient due to the reduced frequency of inserting and re-inserting the cannula. In certain embodiments, the invention allows insulin to be effective beyond 6-days during continuous subcutaneous insulin infusion (CSII) therapy. In particular instances, the invention reduces coagulation in the insulin diffusion pathways, stabilizes insulin from aggregation, and/or improves vascular impact.

Further aspects and embodiments are discussed in the following sections.

Response-Inhibiting Agent Coating

In one or more other embodiments of the invention, the response-inhibiting agent is provided as a coating on a part of the infusion set such as coating the polyvinyl alcohol depot materials. The response-inhibiting agent may be formulated specifically for slow release (i.e. pre-dosed). In one embodiment, the method and device comprises application of a response-inhibiting agent-coated transdermal patch. In a further embodiment, the method and device comprises application of a response-inhibiting agent-coated cannula or catheter. In certain embodiments, the response-inhibiting agent is disposed on a cannula and/or a transdermal patch that secures the infusion set to the patient and/or a drug-coated septum within a reservoir of an infusion pump. In a still further embodiment, the method and device comprises application of a response-inhibiting agent-coated septum or a response-inhibiting agent-impregnated infusion set. The method and device for reducing a diabetic patient's foreign-body immune response may comprise of one or more of the embodiments in various combinations (e.g. a response-inhibiting agent-coated transdermal patch in addition to a response-inhibiting agent-coated cannula).

Transdermal Patch

In one aspect of the invention, the method and device for reducing site-loss/occlusion and/or coagulation in a diabetic patient comprises application of a response-inhibiting agent-coated transdermal patch. Preferably, topical administration of the response-inhibiting agent is by means of a transdermal patch, though the response-inhibiting agent may be administered as, without limitation, an ointment, gel, cream, powder or drops. An advantage of a transdermal patch is that the medicated adhesive patch can be placed on the skin for several days depending on the skin type. The medication can then continuously penetrate the skin to reduce the foreign body response at the subcutaneous infusion site. The medicated transdermal adhesive patch can further be packaged and sold separately to provide various options for infusion pump users.

The transdermal patch comprises a response-inhibiting agent for mitigating a foreign-body response and is applied near the site where a foreign object is subcutaneously inserted. In one or more embodiments, the transdermal patch comprises a substrate layered with an adhesive and response-inhibiting agent intended for local dermal absorption near an insertion site of a subcutaneous infusion set. The transdermal patch may be separate from or a part of the infusion set. While an infusion set is inserted in a patient, normally for multiple-days, the transdermal patch administers a local dose of a response-inhibiting agent near the infusion site of the cannula. This reduces foreign body responses such as site-loss and/or occlusion occurring during the subcutaneous delivery of fluid medication, such as insulin or an insulin analog.

In other embodiments, the invention may be combined with a continuous glucose monitoring device on the same adhesive patch (i.e. "combo-set"). Currently in the art, glucose sensors have a use-life of 6 days whereas infusion sets typically have a recommended use-life of only 2-3 days. The use of the invention disclosed herein enables both devices to be worn for the same duration on the same patch, thereby reducing product use cost. In certain embodiments, the continuous glucose monitoring performance of the combo-set is extended beyond 3 days, and in specific instances, 4, 5 or 6 days. In other instances the glucose monitoring performance of the combo-set is greater than or equal to 6 days.

More than one response-inhibiting agent, such as an anti-inflammatory agent and an anti-coagulation agent, may be administered simultaneously by the transdermal patch. The anti-inflammatory agent may be a steroidal, non-steroidal anti-inflammatory drug or anti-proliferative drug. For example, Table 5 below shows examples of steroids, immunosuppressant drugs, cox inhibitors, non-steroidal anti-inflammatory drugs (NSAIDS), and anti-proliferative agents that can be blended in the adhesive and penetrant to achieve an anti-inflammatory effect. In particular, the anti-inflammatory agent may be rapamycin (sirolimus), tacrolimus, or combination thereof. In specific embodiments, the anti-inflammatory agent is not a methasone (e.g. betamethasone sodium phosphate, dexamethasone sodium phosphate, beclomethasone dipropionate or the like).

Drug-Coated Cannula

In another aspect of the present invention, the method and device for reducing site-loss and/or occlusion in a diabetic patient comprises application of a response-inhibiting agent-coated/loaded cannula. At least a portion of the drug-coated cannula is coated with the response-inhibiting agent. In one or more embodiments, a response-inhibiting agent is coated or loaded on the exterior surface of the cannula. In one or more other embodiments, the response-inhibiting agent is coated or loaded on the interior surface or lumen of the cannula. The response-inhibiting agent-coated cannula provides a direct supply of a response-inhibiting agent to the tissue to combat the natural foreign-body response at the infusion site. In one embodiment, the response-inhibiting agent is directly delivered into a patient's internal tissue environment to achieve an anti-coagulation effect and/or prevent encapsulation of a subcutaneously inserted cannula.

More than one response-inhibiting agent, such as an anti-inflammatory agent and an anti-coagulation agent, may be administered simultaneously. Table 5 below shows examples of steroids, immunosuppressant drugs, cox inhibitors, non-steroidal anti-inflammatory drugs (NSAIDS), and anti-proliferative agents that can be blended in the coating to achieve an anti-inflammatory effect. In particular, the anti-inflammatory agent may be rapamycin (sirolimus), tacrolimus or combination thereof. In specific embodiments, the anti-inflammatory agent is not a methasone (e.g. betamethasone sodium phosphate, dexamethasone sodium phosphate, beclomethasone dipropionate or the like).

In other embodiments, the response-inhibiting agent coating may include only the response-inhibiting agent or may include a response-inhibiting agent in combination with another material such as a polymer, a metal, a metal alloy, a ceramic, a glass, or any combination thereof. The coating may be constructed or applied as multiple layers. The multiple layers may have different materials or compositions, different ratios of materials or compositions, or both in each layer.

Figure 7B:
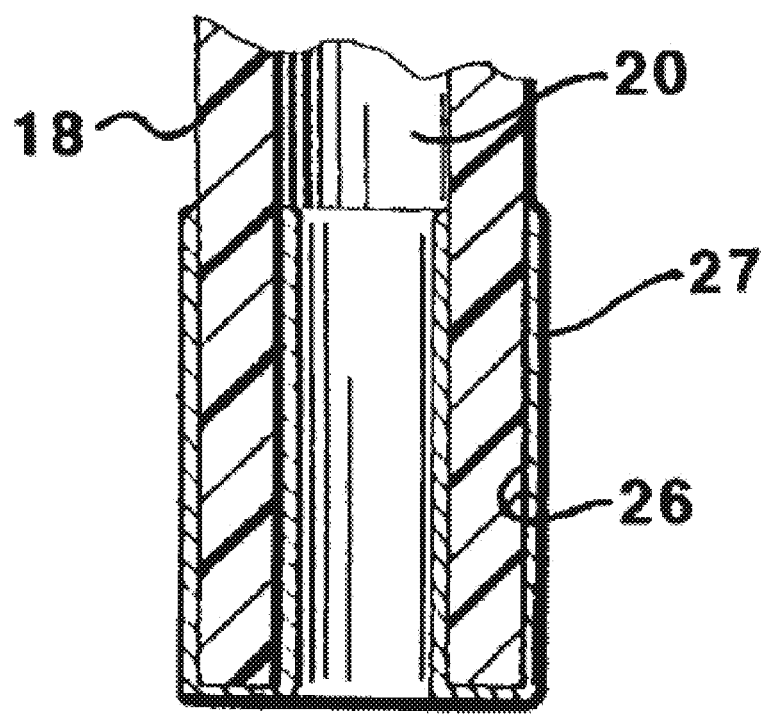

FIG. 7B illustrates one embodiment of the invention where the surface 26 of the distal end 18 of a cannula is provided with a coating 27 of a response-inhibiting agent. As an illustrative implementation, a silicon-based cannula is dipped into a silicon adhesive in which a response-inhibiting agent has been placed into solution. The compound liquid coats the surface 26 of the cannula and, as it solidifies, encapsulates at least a portion of the distal end in the polymer/response-inhibiting agent compound. By use of this structure, the response-inhibiting agent is leached from the cannula when the cannula is in contact with body fluid and acts to combat site-loss and/or occlusion. An alternative to dipping the distal end of the cannula is to spray-coat the distal end of the cannula with a vaporized, compounded solution.

Figure 7C:
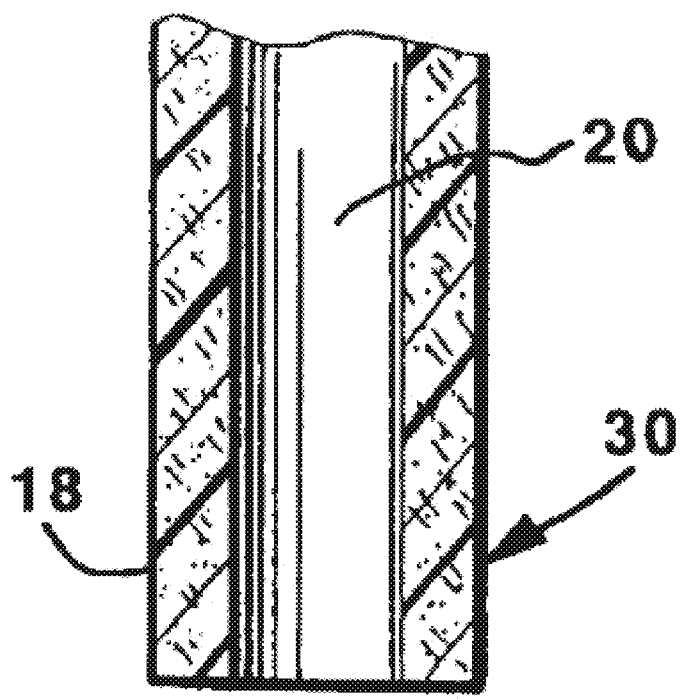

FIG. 7C depicts an alternative embodiment of the invention. In this embodiment, the response-inhibiting agent is provided throughout the body of the cannula by mixing and compounding the response-inhibiting agent directly into the cannula polymer melt before forming the cannula. For example, the response-inhibiting agent can be compounded into materials such as silicone rubber or urethane. The compounded material is then processed conventionally as by extrusion, transfer molding or casting, for example, to form a tubular configuration. The cannula 30 resulting from this process benefits by having the response-inhibiting agent dispersed throughout the entire cannula body. The response-inhibiting agent slowly leaches or diffuses into the patient's tissue from the cannula, thereby preventing or resisting site-loss and/or occlusion in and around the cannula 30.

Figure 7D:
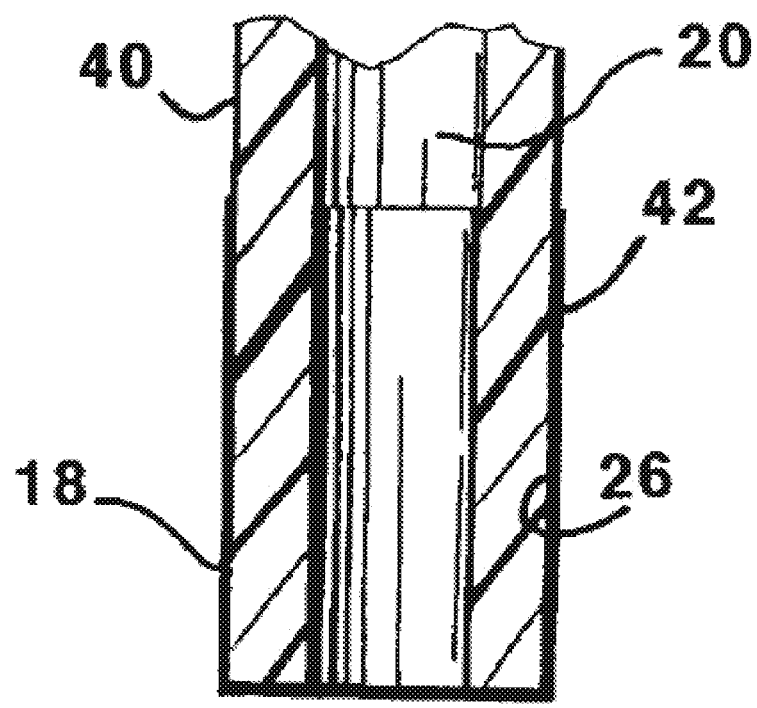

FIG. 7D depicts another embodiment of the invention. In this embodiment, a thin layer 42 of a response-inhibiting agent has been covalently bonded to the exterior surface 26 of the cannula 14. The surface is prepared to molecularly receive the response-inhibiting agent. A binding agent may be needed between the response-inhibiting agent molecules and the polymer molecules on the surface 26. With this structure, the response-inhibiting agent is present on the exterior surface of the cannula and can be leached away to combat site-loss and/or occlusion.

In further embodiments, the structure of the cannula may include, without limitation, holes, grooves, pores, indentations, or a combination thereof on its surface where the response-inhibiting agent is partially or completely contained within at least a portion of the holes, grooves, pores, indentations or combinations thereof. In one or more embodiments, the invention provides a cannula modified with different structural configurations that incorporate holes and/or wells for loading one or more response-inhibiting agents (see FIG. 5 and Table 1 below). Table 1 illustrates six different configurations for a cannula comprising a combination of holes and/or wells. Other numbers and combinations of holes and wells may also be used.

TABLE 1

| Configuration | Description | Hole (A) | Well (B) |
| --- | --- | --- | --- |
| 1 | 1 hole (A) with diameter of 0.005" ± 0.0005" at distance 0.025" from tip, on one side wall | 1 | None |
| 2 | 2 hole (A) with diameter of 0.005" ± 0.0005" at distance 0.025" from tip, on both side | None | |

TABLE 1-continued

| Configuration | Description | Hole (A) | Well (B) |
| --- | --- | --- | --- |
| 3 | 1 hole (A) with diameter of 0.005" ± 0.0005" at distance 0.025" from tip, on one side wall, one well below hole | 1 | 1 |
| 4 | 2 hole (A) with diameter of 0.005" ± 0.0005" at distance 0.025" from tip, on both side, each well directly below each hole A | 2 | 2 |
| 5 | 1 hole (A) with diameter of 0.005" ± 0.0005" at distance 0.025" from tip, on one side wall, one well 90° hole A | 1 | 1 |
| 6 | 2 hole (A) with diameter of 0.005" ± 0.0005" at distance 0.025" from tip, on both side, each well is 90° below each hole A | 2 | 2 |

The holes and/or wells incorporated within the cannula structure allow flexibility in coating and loading one or more response-inhibiting agents for controlled-release or instant-release. By introducing one or more response-inhibiting agents at the same time within one insertion, the development of a foreign body reaction in response to insertion in the subcutaneous tissue is prevented. In addition, a response-inhibiting agent can also be further impregnated into the cannula for controlled release of the response-inhibiting agent.

In another aspect of the invention, the cannula structure reduces the penetrating trauma on the tissue from insertion. The microarchitecture of the cannula, particularly at the surface, is an important parameter that influences the host response. Cannula structures found in existing art can result in densely packed, well-organized fibrous capsules, whereas the modified cannula disclosed herein (which incorporates holes and/or wells) leads to a less dense, more open, and disorganized fibrous capsule which can reduce the extent of the tissue injury at the insertion site.

Additionally, the incorporation of holes or ports in the cannula increases the number of infusion sites. This lowers the pressure from fluid medication (e.g. insulin) administration at each infusion site, thereby resulting in less tissue injury. The holes and wells also increase anchorage of the cannula so that movement of the cannula while the patient is moving is prevented. Less movement of the cannula results in reduced injury, blood clots, and infection for the patient.

In one or more embodiments, a response-inhibiting agent is delivered via a cannula coated with the response-inhibiting agent or the response-inhibiting agent and an anti-inflammatory agent and further infused with insulin. In another exemplary implementation, the response-inhibiting agent is continually infused with insulin to the patient. In a further exemplary implementation, the patient is pre-dosed with a response-inhibiting agent, followed by continued infusion of insulin.

Response-Inhibiting Agent Depot

Artificial pancreas systems combine a Continuous Glucose Monitor (CGM), algorithm, and insulin delivery system to provide automated insulin delivery. One challenge for artificial pancreas systems is the requirement for two external sites for insulin infusion and the Continuous Glucose Monitor (CGM). At present, CGMs are transitioning to a 14 day wear duration from 7 days, adding to user burden due to discrepant timing of site change and limiting the potential for combined infusion and CGM sites. Hence, to reduce the burden for people with type 1-diabetes of managing infusion sites and to facilitate more user-friendly artificial pancreas configurations, the present invention extends the duration of infusion sets to match CGM wear durations. The current invention, in combination with site-loss mitigating agents, addresses and mitigates the fundamental mechanism of failure and provides mitigation to known failure modes when delivering insulin via a sub-cutaneous cannula. In preferred embodiments, it increases the reliability of insulin infusion and extends the wear duration of infusion sets and patch pumps to match the wear duration of CGMs for people with type 1-diabetes.

Figure 15:
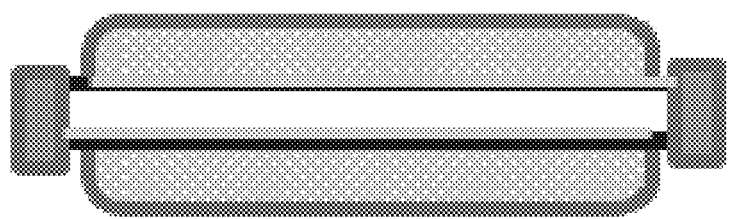
FIG. 15 is an illustration of an in-line chamber (A) and in-line plug (B) for continuous heparin delivery.
Figure 15:

In one or more embodiments of the invention, a response-inhibiting or site-loss mitigating agent is provided in a depot attached to a section of the fluid path of the infusion pump. An in-line response-inhibiting/site-loss mitigating agent depot or pre-filled cartridge is used for continuous response-inhibiting/site-loss mitigating agent delivery. The in-line response-inhibiting/site-loss mitigating agent depot may be in the form of an in-line response-inhibiting/site-loss mitigating agent depot, chamber or plug (see, e.g. an in-line heparin depot, chamber or plug as shown in FIGS. 15A and 15B).

Typically, the response-inhibiting/site-loss mitigating agent is loaded or disposed within a depot and adapted to contact an insulin solution as the insulin solution flows from the medication reservoir to the single site of infusion. In one or more embodiments, the depot is a foam, a sponge or a polymeric material. In one specific implementation, the depot is assembled on a needle, which is in operable contact with the medication reservoir and the fluid conduit, thereby allowing the response-inhibiting/site-loss mitigating agent (e.g. heparin) to be released through contact/absorption/releasing in the insulin fluid path.

In one embodiment, the depot comprises two or more foams, sponges or polymeric materials. In preferred embodiments, the two or more foams, sponges or polymeric materials are loaded with various amounts of the response-inhibiting/site-loss mitigating agent. Illustrative experiments have demonstrated that such combinations of two or more foams, sponges or polymeric materials are effective at tuning the elution profile of the response-inhibiting/site-loss mitigating agent in the insulin infusion to a desired pattern. In certain instances, the response-inhibiting/site-loss mitigating agent is heparin and each foam, sponge or polymeric material comprises 50 U to 500 U of heparin/piece.

Figure 27B:
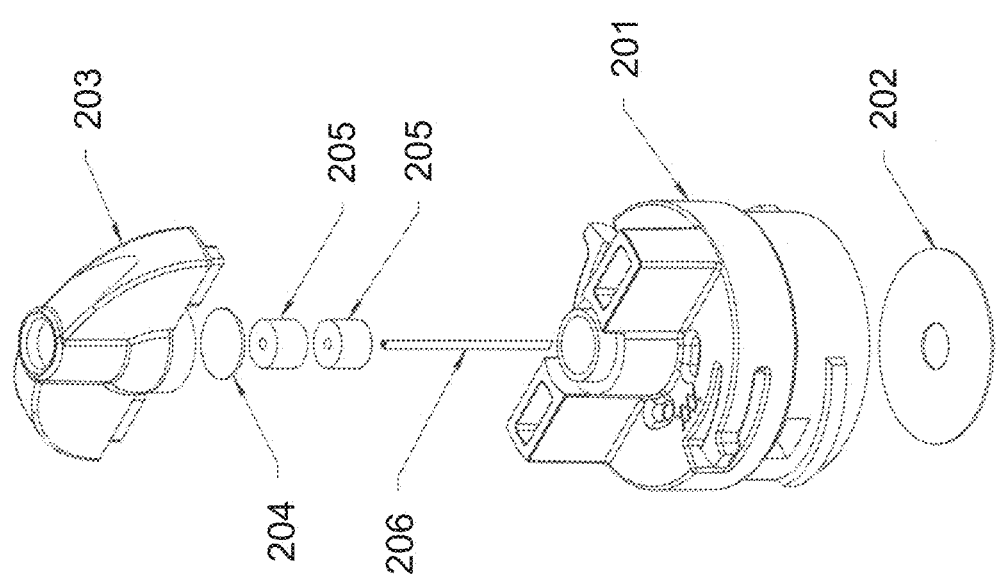
FIGS. 27A-B are exploded views of embodiments of a connector.
Figure 27A:
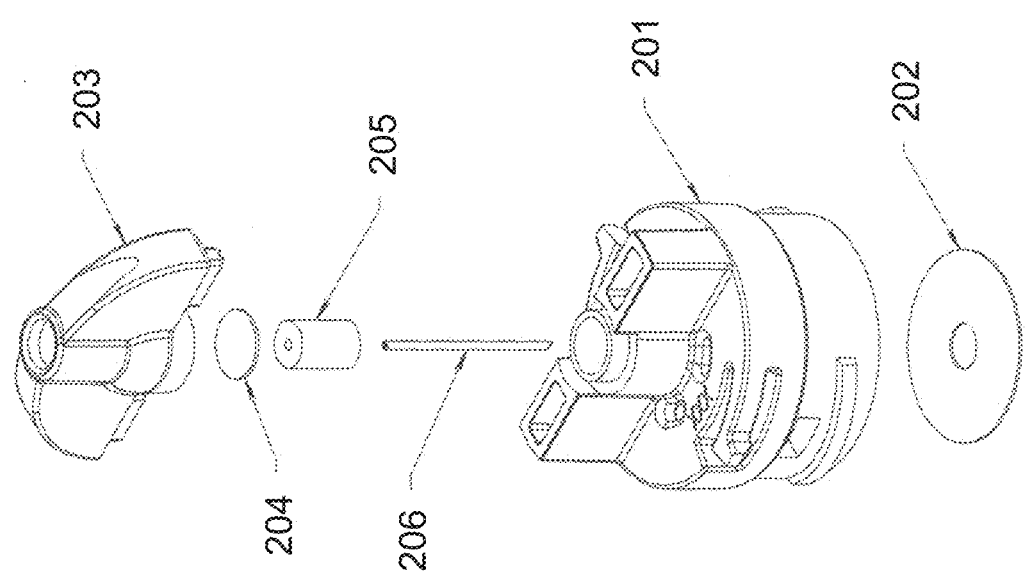
Figure 28D:
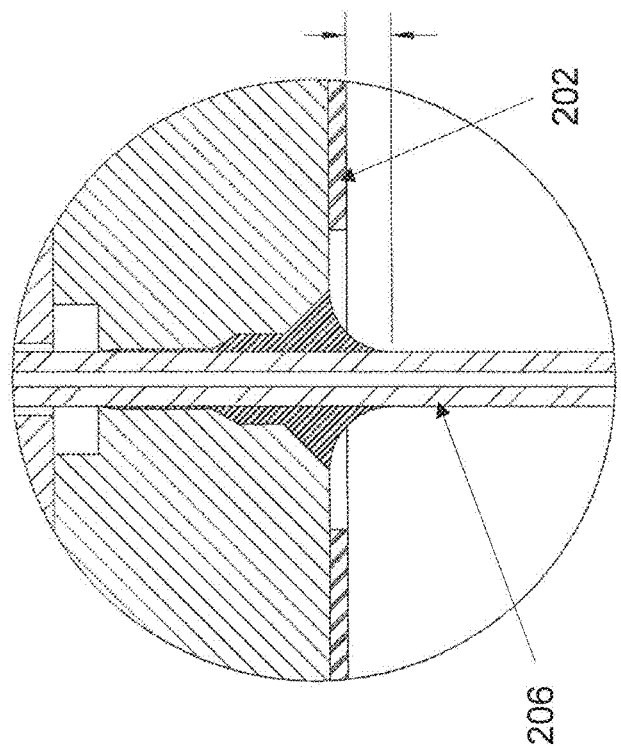
Figure 28C:
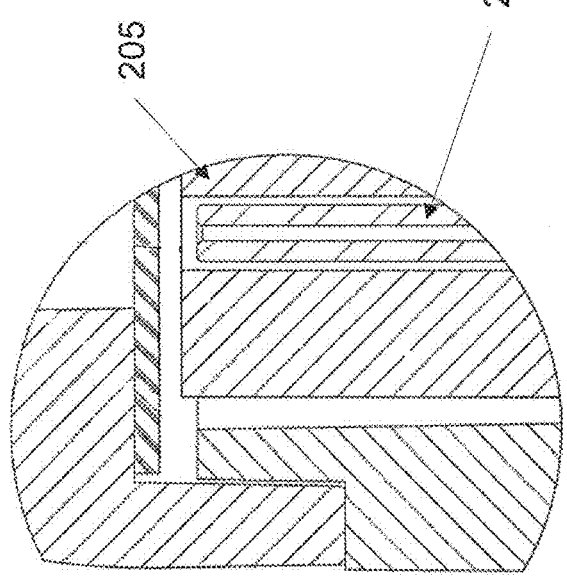
Figure 29C:
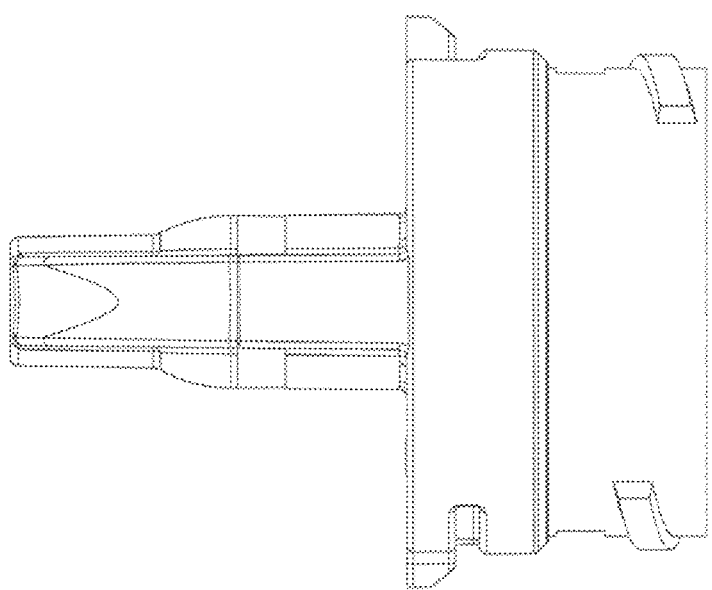

For example, FIGS. 27A-B are exploded views showing embodiments of a connector with a base cap 201 and top cap 203. The base cap 201 is positioned over a venting membrane 202 and the top cap 203 is positioned over a reservoir membrane 204. One or more depots 205 (e.g. foams) are assembled on a needle 206. In these embodiments, the depots 205 are cylindrical. FIGS. 28A-D are fully assembled views showing an embodiment of a connector. FIG. 28A is a top-down view of the connector. FIG. 28B is a cross-sectional view of the connector taken along the line A-A in FIG. 28A. FIG. 28C is an enlarged view of circled portion B in FIG. 28B. FIG. 28D is an enlarged view of circled portion C in FIG. 28B. As seen in FIG. 28C, there is a gap between the needle 206 and the reservoir membrane 204 that allows a site-loss mitigating agent to be released from the depot 205 through contact/absorption/releasing in the insulin fluid path. FIGS. 29A-C are fully assembled views showing another embodiment of a connector. FIG. 29A is a top-down view of the connector. FIG. 29B is a cross-sectional view of the connector taken along the line D-D in FIG. 29A. FIG. 29C is a side view of the connector.

In one or more embodiments, an extended release formulation of heparin, in the form of loaded foams, sponges or polymeric materials (i.e. those with a depot) and assembled in the fluid path of insulin infusion pumps, is capable of extending the insulin infusion set beyond the current use of 3 days. In various instances, the insulin infusion set is used at least 4, 5, 6, 7, 8 or 9 days. In one embodiment, the formulation comprises at least two different extended release heparin-containing components, wherein each component comprises a release controlling loading specific for its component and comprising an absorbing material selected from the group consisting of medical-grade polyvinyl alcohol, cellulose, polyurethane, or others. In one instance, the formulation exhibits the following elution profile when measured under simulated-use conditions: a) in the first 3 days, heparin concentration in insulin solution is maintained between 100 U/mL to 1200 U/mL; b) after 3 days, there is still a detectable amount of heparin released in the insulin infusate solution. See, e.g. Table 13 below.

TABLE 13

Example Elution Profiles

| Sample ID | Media | Pumping Rate | Heparin Eluted (U) at | | | | | | | Heparin Recovered | | |
|---|---|---|---|---|---|---|---|---|---|---|---|---|
| | | | Day 1 | Day 2 | Day 3 | Day 4 | Day 5 | Day 6 | Day 7 | Total (U) | LC (U) | % LC |
| Group 3-1 | Novolog | 0.5 U/hr + | 44.7 | 261.3 | 45.6 | 12.0 | 4.4 | 3.8 | 5.6 | 378 | 400 | 94 |
| Group 3-2 | | Bolus = | 44.7 | 239.9 | 102.0 | 19.6 | 6.1 | 3.7 | 4.2 | 420 | 400 | 105 |
| Group 3-3 | | 24 U/day | 73.3 | 242.4 | 70.8 | 18.6 | 6.3 | 3.7 | 5.2 | 420 | 400 | 105 |
| Group 5-1 | Humalog | 1.0 U/hr = | 52.3 | 255.2 | 64.0 | 15.3 | 6.3 | 2.8 | 1.8 | 398 | 400 | 99 |
| Group 5-2 | Placebo | 24 U/day | 46.4 | 239.1 | 95.1 | 17.9 | 5.5 | 2.7 | 2.3 | 409 | 400 | 102 |
| Group 5-3 | | | 40.1 | 207.1 | 79.9 | 28.0 | 15.3 | 6.9 | 4.2 | 382 | 400 | 95 |
| Group 6-1 | Novolog | 1.5 U/hr = | 155.6 | 201.9 | 25.9 | 6.5 | 5.1 | 4.7 | 6.2 | 406 | 400 | 101 |
| Group 6-2 | | 36 U/day | 132.8 | 196.6 | 61.1 | 13.2 | 5.9 | 4.6 | 6.2 | 421 | 400 | 105 |
| Group 6-3 | | | 153.8 | 204.7 | 64.9 | 7.7 | 5.3 | 4.2 | 6.9 | 447 | 400 | 112 |
| Targeted Heparin Dosing | | | 25-300 U/day for the first 3 days | | | | | | | | | |

Response-Inhibiting Agent Reservoir

Figure 14:
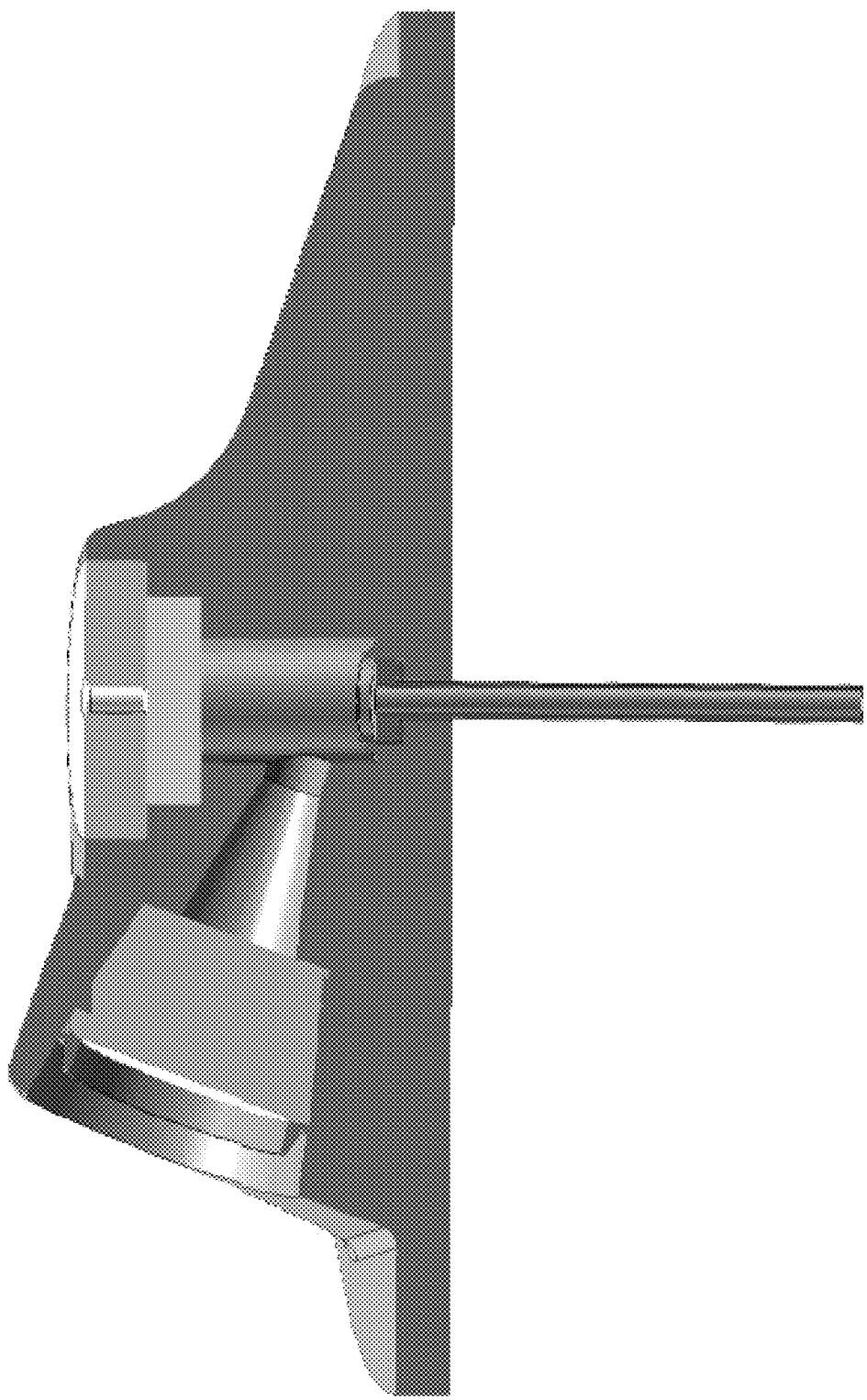
FIG. 14 is an illustration of an embodiment of the device with a dual chamber reservoir for delivering heparin along with insulin.

In one or more other embodiments of the invention, the response-inhibiting agent is provided in a depot/reservoir where the response-inhibiting agent is present in the infusate. In certain embodiments, the response-inhibiting agent is pre-mixed with the medication prior to infusion into a patient. In other embodiments, the response-inhibiting agent is mixed in-situ along the fluid path of medication administration. An infusion pump may have a dual chamber depot/reservoir with one reservoir for medication and another for a response-inhibiting agent (see, e.g. use of heparin as shown in FIG. 14). There may also be a dual line on the injection catheter or cannula. In certain embodiments, the response-inhibiting agent is co-infused with the insulin. The response-inhibiting agent and insulin are delivered from two different reservoirs and then mixed in-situ upon infusion.

Drug-Coated Septum and Drug-Impregnated Infusion Set

In another aspect of the present invention, the method and device for reducing site-loss and/or occlusion in a diabetic patient comprises application of a response-inhibiting agent-coated septum patch or a response-inhibiting agent-impregnated infusion set (see FIG. 1). The response-inhibiting agent-coated septum patch and response-inhibiting agent-impregnated infusion set reduce site-loss and/or occlusion resulting from the subcutaneous insertion of a foreign object, such as a cannula or catheter of an infusion set.

Embodiments of the invention include patch pump infusion systems (e.g. a patch pump infusion system having a profile smaller than 5 inches by 7 inches, or smaller than 4 inches by 6 inches, or smaller than 3 inches by 5 inches, or smaller than 2 inches by 3 inches) and patch pump baseplates, optionally impregnated with active pharmaceutical ingredients such as anti-inflammatory agent (e.g. heparins, corticosteroids or the like), and active time-release formulations intended for immediate or extended release via the distal end of the patch infusion pump. In one patch pump embodiment, the infusion pump comprises a dual reservoir for dual infusion of two drugs (e.g. insulin and heparin). In another embodiment, the tubing system and/or cannula is lined (impregnated) or coated with a response-inhibiting agent to reduce site-loss and/or occlusion. Table 6 below shows examples of steroids, immunosuppressant drugs, cox inhibitors, non-steroidal anti-inflammatory drugs (NSAIDS), and anti-proliferative agents that can be mixed with the fluid medication, e.g. insulin formulation, (either pre-mixed or delivered separately at the infusion site) to achieve further anti-inflammatory effect.

In other embodiments, a response-inhibiting agent-coated septum, such as a silicone rubber septum, is impregnated with a time-release response-inhibiting agent and housed within the reservoir or infusion set fluid path pass-through. Since the response-inhibiting agent-coated septum is positioned within the fluid path of the infusion pump, the response-inhibiting agent is thereby added to the fluid medication (e.g. insulin) upon administration of the medication. Delivery of the response-inhibiting agent along with the medication reduces coagulation at the infusion site and reduces the risks associated with site-loss and/or occlusion resulting from multiple-day subcutaneous therapeutic drug infusions and extended wear of infusion sets and baseplates delivering therapeutic fluids.

Response-Inhibiting Agents

In one aspect of the present invention, the response-inhibiting agent is an anti-coagulant. This includes heparin and derivatives such as low molecular weight heparin (e.g. Enoxaparin sodium (Lovenox™), Dalteparin sodium (Fragmin™)), Fondaparinux (Arixtra™), and Idraparinux (in development by Sanofi-Aventis™, sub-cue). Fondaparinux is a synthetic sugar composed of the five sugars (pentasaccharide) in heparin that bind to antithrombin. It is a smaller molecule than low molecular weight heparin. Other anti-coagulants include coumarins (vitamin K antagonists) such as warfarin, acenocoumarol, phenprocoumon, atromentin, and phenindione. Warfarin (Coumadin™) is an agent typically used in the US and UK. Acenocoumarol and phenprocoumon are used more commonly outside the US and the UK. Anti-coagulants also include direct factor Xa inhibitors (pills) such as rivaroxaban (Xarelto™), apixaban edoxaban ((INN, codenamed DU-176b, trade name Lixiana™); direct thrombin inhibitors such as bivalent drugs (e.g. hirudin, lepirudin, and bivalirudin) and monovalent drugs (e.g. argatroban and dabigatran (Pradaxa™)). They are often used for treatment of thrombosis in patients with heparin-induced thrombocytopenia (HIT). Anti-coagulants also include antithrombin protein (purified from human plasma or produced recombinantly).

In one or more embodiments of the invention, the response-inhibiting agent is heparin. Heparin is a member of the glycosaminoglycan family of carbohydrates and comprises a variably sulfated repeating disaccharide unit, such as β-D-glucuronic acid-2-deoxy-2-acetamido-α-D-glucopyranosyl, β-D-glucuronic acid-2-deoxy-2-sulfamido-α-D-glucopyranosyl, α-L-iduronic acid-2-deoxy-2-sulfamido-α-D-glucopyranosyl, 2-O-sulfo-α-L-iduronic acid-2-deoxy-2-sulfamido-α-D-glucopyranosyl, α-L-iduronic acid-2-deoxy-2-sulfamido-α-D-glucopyranosyl-6-O-sulfate or 2-O-sulfo-α-L-iduronic acid-2-deoxy-2-sulfamido-α-D-glucopyranosyl-6-O-sulfate. Although it is used principally in medicine for anticoagulation, its true physiological role in the body remains unclear, because blood anticoagulation is achieved mostly by heparan sulfate proteoglycans derived from endothelial cells.

Surprisingly, it was discovered that the heparin helps stabilize insulin in the solution, as well as facilitates insulin absorption and effectively lowers glucose in-vivo. This effectively lowers the local inflammatory response caused by insulin build-up/aggregation or debris accumulation. In various embodiments, an infusion set described herein can be used for at least 6 days. In other embodiments, the period of time is at least 6, 7, 8, 9, 10, 11 or 12 days. In one embodiment, heparin is directly added to an insulin formulation prior to and/or during administration or infusion of the insulin formulation to a diabetic patient. Preferably, the concentration range of heparin added to the insulin formulation is 40 U/ml to 8000 U/ml or 0.1 mg/ml to 20 mg/ml. In a specific instance, 800 U/ml of heparin is continuously infused along with the insulin to prevent site-loss for at least 6 days. Preferably, heparin is dosed 0.1 to 80 U/kg/day. In a specific instance, heparin is dosed 8 U/kg/day. Notably, this is significantly less than the heparin dosing used in other therapeutic treatments, which is typically 150 to 400 U/kg/day.

In another aspect of the present invention, the response-inhibiting agent is an anti-platelet agent. This includes irreversible cyclooxygenase inhibitors, aspirin, triflusal (Disgren™), adenosine diphosphate (ADP) receptor inhibitors, clopidogrel (Plavix™), prasugrel (Effient™), ticagrelor (Brilinta™), ticlopidine (Ticlid™), phosphodiesterase inhibitors, cilostazol (Pletal)™, glycoprotein IIB/IIIA inhibitors (intravenous use only), abciximab (ReoPro™), eptifibatide (Integrilin™), tirofiban (Aggrastat™), adenosine reuptake inhibitors, dipyridamole (Persantine™), thromboxane inhibitors, thromboxane synthase inhibitors, and thromboxane receptor antagonists (Terutroban™).

For aspirin, a daily dose of aspirin that is commonly recommended by health care professionals in order to prevent platelets from clumping together and forming clots. Although new blood thinner medications are constantly emerging on the market, aspirin remains a commonly used preventative tool. Warfarin (Coumadin™) is one of the most well known medications used to thin the blood. It is an anti-coagulant that is also used in some cases to prevent heart disease. Pradaxa™ is a newer medication that is used primarily in people who have an arterial fibrillation. It is geared towards preventing blood clots and strokes. Elequis™ essentially lowers the risk of both blood clots and strokes. Elequis™ is a relatively new drug that is thought to be a competitor to the side effect laden Coumadin™ Xarelto™ is especially useful in recipients of hip replacements and knee replacements. Xarelto™ is a newcomer amongst blood thinner medications and has also been approved for use in cases of DVT as well as pulmonary embolisms. Clopidogrel (Plavix™) works by preventing coagulation of the platelets in the blood. It is especially suited for people who have certain medical conditions and heart conditions. It is also used as a preventative tool against the formation of clots in persons who have had a heart attack or stroke. Like aspirin, Prasugrel™ is an anti-platelet medication. In people who have been treated with angioplasty, Prasugrel™ may be used in conjunction with aspirin to prevent the formation of clots. Brilinta™ is typically prescribed following a heart attack and can be used in conjunction with aspirin. It has been proven effective at reducing the chance of recurring heart attacks in people who have had them before and the medication is thought to further reduce the risk of recurrent heart attacks with continued use. Cilostazol™ is used to improve the flow of blood to the legs and can help assist with reducing the symptoms of intermittent claudication. Like some of the other blood thinner medications on described herein, Cilostazol™ is an anti-platelet medication, whereby it is used to prevent the platelets in the blood from clumping together. Aggrenox™ is essentially a prescription super aspirin. It is a combination of two medicines, aspirin and dipyridamole. In people who have had blood clots, the Aggrenox™ medication.

Additionally, Table 5 below lists various anti-inflammatory agents and drugs that may be used in conjunction with the response-inhibiting agent in accordance with one or more embodiments of the invention. However, such a list is not exhaustive and additional examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cortodoxone, deflazacort, desonide, desoximetasone, mometasone, cortisone, cortisone acetate, hydrocortisone, prednisone, prednisone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, tacrolimus and pimecrolimus.

Additionally, examples of steroidal anti-inflammatory drugs include, without limitation, 21-acetoxypregnenolone, alclometasone, algestone, amcinonide, budesonide, chloroprednisone, clobetasol, clobetasone, clocortolone, cloprednol, corticosterone, cortisone, cortivazol, deflazacort, desonide, desoximetasone, diflorasone, diflucortolone, difluprednate, enoxolone, fluazacort, fluclorinide, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof.

Furthermore, examples of nonsteroidal anti-inflammatory drugs include, without limitation, COX-1 and COX nonspecific inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin), and selective COX-2 inhibitors (e.g., diaryl-substituted furanones such as rofecoxib; diaryl-substituted pyrazoles such as celecoxib; indole acetic acids such as etodolac and sulfonanilides such as nimesulide), and combinations thereof.

Additionally, other naturally occurring or synthetic drugs, agents, molecules (e.g. hyaluronidase), and proteins may be included with the response-inhibiting agent to mitigate foreign-body responses and/or help facilitate the body in absorbing the medication.

EXAMPLES

Example 1: Understanding the Site-Loss Mechanism Using Animal Models

Causes of site reduction are poorly understood and can be due to localized inflammation or tissue proliferation. Understanding the cause through a time-based biopsy study allows for development of infusion sets that could be extended beyond three days, hence improving patient comfort and compliance. A diabetic animal model that shows site reduction 2-10 days after placement of transdermal insulin pumps is used so that the local tissue response to continuous subcutaneous insulin infusion (CSII) can be studied by in-situ skin biopsies.

FIG. 1 is an illustration of an exemplary medical device used for diabetes management which includes a fluid path schematic of an insulin pump. An illustrative infusion set comprises a three-layer tubing of polyethylene (PE), ethylene vinyl acetate (EVA), and polyvinyl chloride (PVC). The catheter material may be Teflon™ or stainless steel.

Continuous subcutaneous insulin infusion (CSII) is an effective method for diabetic care. Local site reaction/site-loss (at approximately 3 days) is often encountered clinically, yet poorly understood. A clinical manifestation of site-loss is the increase in blood glucose while a patient is on CSII. Existing theories include changes in insulin absorption, inflammation, and lipoatrophy (localized lost of fat). Better understanding of the site-loss phenomenon can provide guidance in making business decisions, such as if putting effort on improving an infusion set to extend site use is possible or necessary.

The goal of studying insulin infusion site-loss using a diabetic porcine model is to establish the methods and animal model necessary to reproduce the phenomenon of site-loss in Continuous Subcutaneous Insulin Infusion (CSII). Methodologies are established for evaluating infusion sites in healthy and diabetic pigs, including device placement and animal management, glucose monitoring, insulin detection, pharmacokinetics, site harvesting, and pathological evaluation. The host response to implanted functional devices is assessed in healthy and diabetic pigs. Parameters that are believed to impact site-loss are varied until site-loss is observed.

TABLE 2

| Experimental Plan | |
| --- | --- |
| Study | Purpose |
| PK/PD Study | To evaluate the blood glucose response in normal/diabetic pigs to Humalog ™ (a rapid-acting insulin) |
| Placement of Infusion Set | To establish proper methodology for infusion set placement and secure. |
| Glucose Monitoring | To establish glucose testing methodology: using blood glucose meter vs. continuous interstitial glucose sensor. |
| Dosing/Animal Management | 1. To evaluate the response of blood glucose level to basal rate. 2. Based on the dosing study results, manage glucose level. |
| Site - Loss Evaluation | To evaluate if/when blood glucose level cannot be managed by insulin delivered through the infusion set implanted at one injection site. |
| Histopathology | To assess the host response at infusion sites. |
| Data Correlation | To correlate the collected data and evaluate reasons for site-loss. |
| Additional i-Port Study | To evaluate if site-loss is caused by continuous infusion |

Factors influencing insulin pK/pD properties include inflammation, infection, immune response, wound healing cascade, age of patients, type of insulin used, site of insertion, layer of scar tissue where the catheter tip resides, and several others.

6 Yucatan pigs were used in this study: 2 normal and 4 diabetic pigs, as shown in Table 3.

TABLE 3

| | Normal (Control) | | Diabetic | | | |
| --- | --- | --- | --- | --- | --- | --- |
| Information | 3413755-Kili | 341376-Fili | 341423-Mike | 341424-Greg | 341425-Peter | 341426-Bobby |
| Gender | Male | Male | Male | Male | Male | Male |
| Birth Date | May 16, 2011 | May 16, 2011 | Jul. 1, 2011 | Jul. 6, 2011 | Jul. 3, 2011 | Jul. 6, 2011 |
| Arrival Date | Dec. 22, 2011 | Dec. 22, 2011 | Feb. 14, 2012 | Feb. 14, 2012 | Feb. 14, 2012 | Feb. 14, 2012 |
| Weight (kg) | 37.9-43.5 | 29.2-36.3 | 27.0-28.1 | 29.8-28.2 | 25.3-26.2 | 25.6-32.1 |

The experimental results show that insulin lispro can effectively lower blood glucose level in both normal and diabetic Yucatan pigs. Insulin lispro (e.g. marketed by Eli Lilly and Company™ as Humalog™) is a fast acting insulin analogue. The infusion sets were able to be inserted into proper position underneath diabetic pig skin and served as the only means to deliver insulin to manage glucose level. Interstitial sensors were used to monitor porcine glucose level. No significant difference was detected between glucose values by sensors placed nearer to or farther away from the infusion site, or by blood meter. The degree of glucose-lowering was found to vary from pig to pig, even from site to site on one pig.

Site-loss was evaluated using a criteria of a prolonged high blood glucose level (greater than 350 mg/dl) as well as being ineffectively controlled by increasing insulin basal/bolus rate. Site-loss observed was pig dependent, sometimes site-dependent. The site-loss was observed in two of the pigs (#341423 and #341424) at approximately 3 days. The other two pigs (#341425 and #341426) had no site-loss in 7 days if a proper site was located. In general, the pigs with observed site-loss were less responsive to a Humalog™ dose. Histologically, the predominant tissue response was inflammation and, with longer infusion, fibrosis. Inflammation scores trended to be of higher grade in diabetic pigs compared to normal pigs, with a larger inflammation area around the catheter tip. Data indicated possible correlation between inflammation and responsiveness to Humalog™.

TABLE 4

| Site-Loss Studies Conducted | | | | |
| --- | --- | --- | --- | --- |
| | Days of Site-loss Observed | | | |
| Period | 341423-Mike | 341424-Greg | 341425-Peter | 341426-Bobby |
| 3/19-3/26 | ~3 | ~3 | No Site-loss | No Site-loss |
| 4/23-5/1 | ~3 | ~3 | No Site-loss | No Site-loss |
| 5/3-5/7* | N/A | N/A | 2-3 | N/A |
| 5/7-5/11 | 2-3 | N/A | N/A | N/A |
| 5/10-5/14 | N/A | N/A | No Site-loss | No Site-loss |
| 5/14-5/18 | N/A | N/A | <1 | ~1.5 |
| 5/22-5/25 | ~1 | Data Varies | <1 | No Site-loss |

Figure 2A:
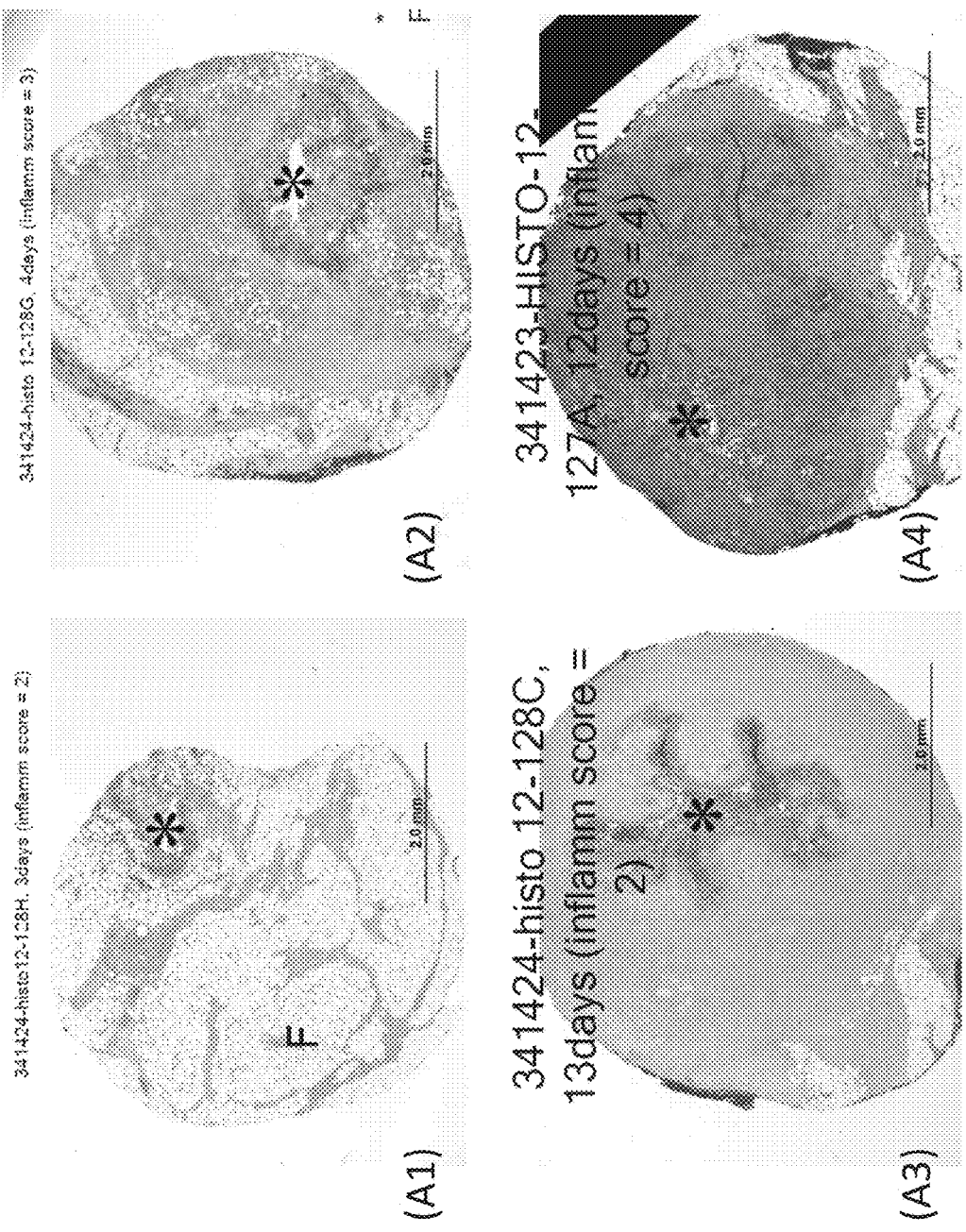
FIG. 2A is a series of histologic evaluations at the cannula tip showing the inflammatory response (score) and size of the area with tissue reaction. "*" indicates the cannula location and "F" indicates normal fat. Inflammation resulted in localized fat loss.
Figure 2B:
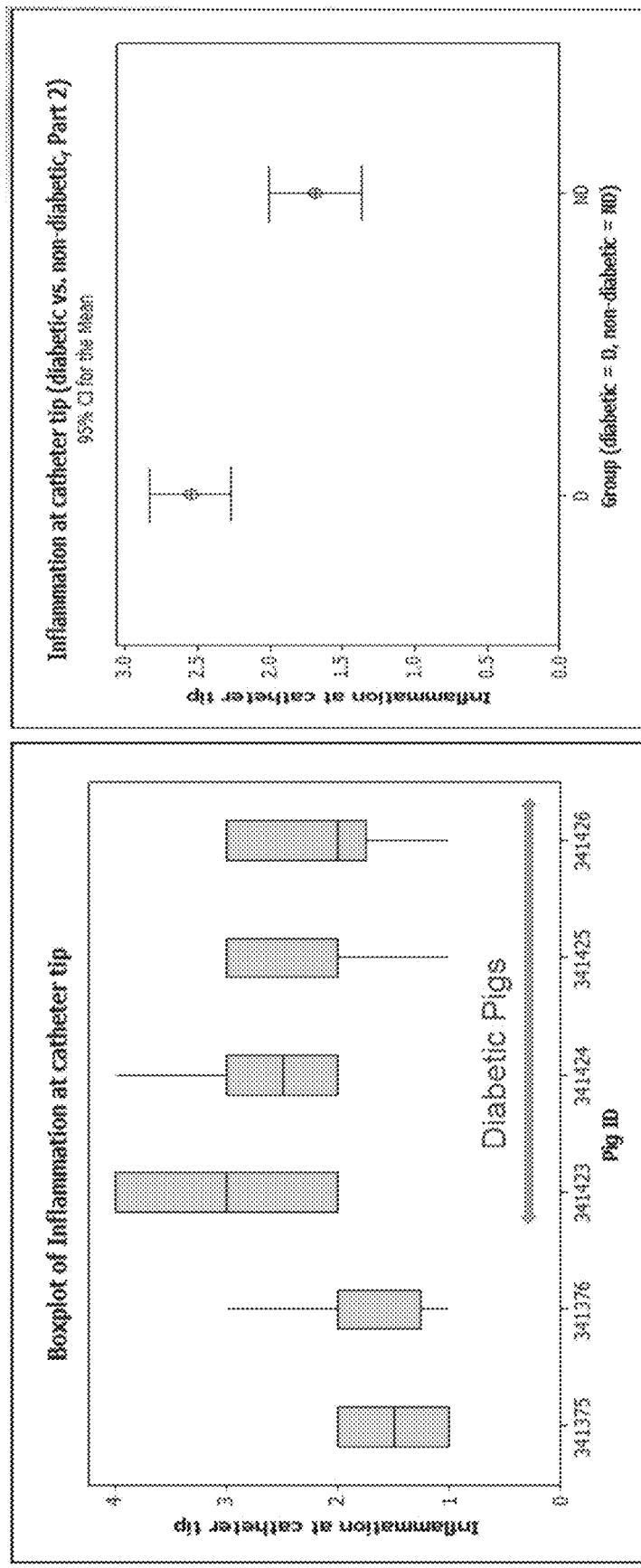
FIG. 2B is a series of graphs illustrating the inflammation at the cannula tip for diabetic and non-diabetic pigs. Localized inflammation loosely correlated with site-loss.

FIG. 2A is a series of histologic evaluations at the catheter tip showing the inflammatory response (score), and size of the area with tissue reaction. "*" indicates the catheter location and "F" indicates normal fat. Inflammation resulted in localized fat loss. FIG. 2B is a series of graphs illustrating the inflammation at the catheter tip for diabetic and non-diabetic pigs. Localized inflammation loosely correlated with site-loss.

Figure 2C:
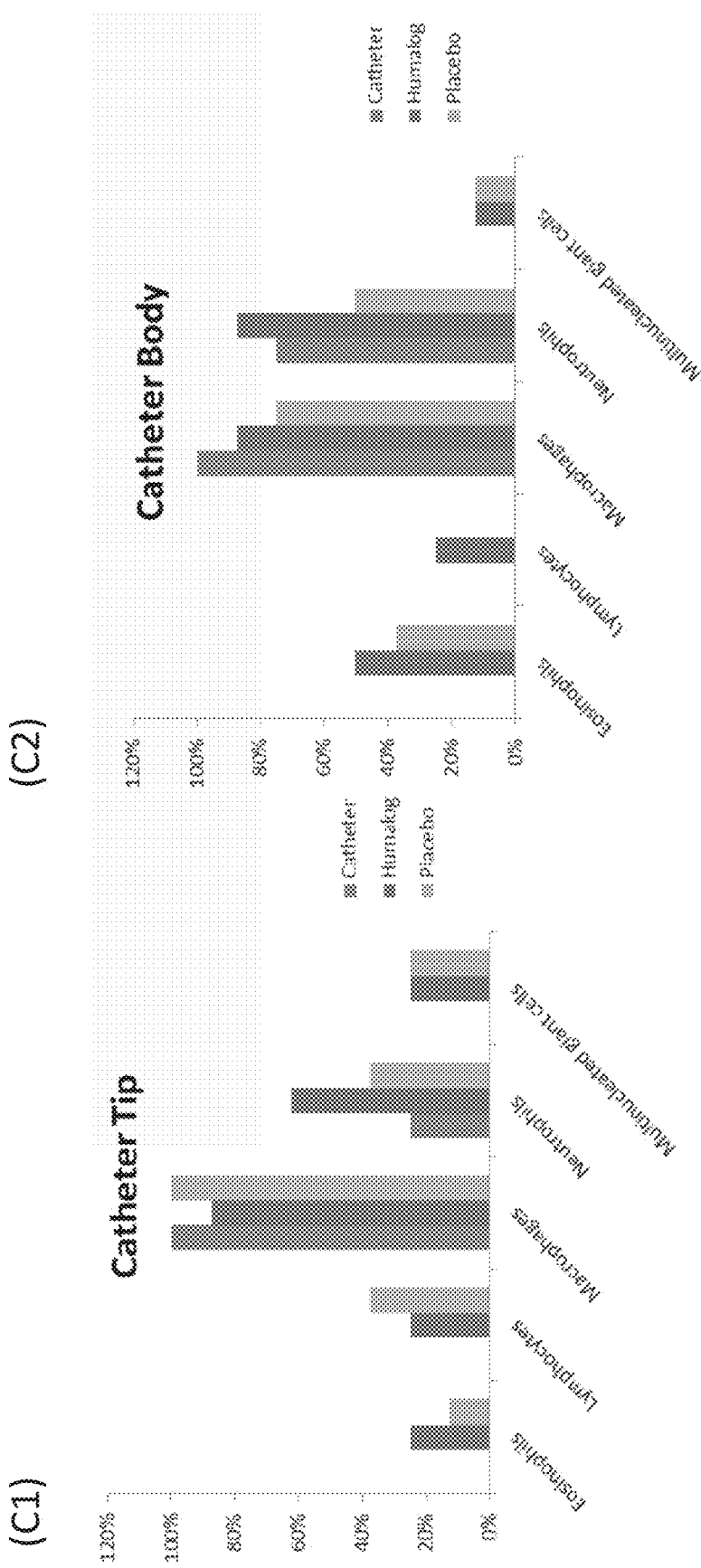
FIG. 2C is a series of graphs illustrating the predominate inflammation cells at the cannula tip and cannula body (qualitative). To isolate the main inflammation contributors, a cannula, a cannula infused with insulin (Humalog), and a cannula infused with placebo were placed on a diabetic pig at the same time. Evaluated inflammation scores were found to be in the same order: insulin≥placebo≥cannula.

FIG. 2C is a series of graphs illustrating the predominate inflammation cells at the catheter tip and catheter body (qualitative). To isolate the main inflammation contributors, a catheter, a catheter infused with insulin (Humalog), and a catheter infused with placebo were placed on a diabetic pig at the same time. Evaluated inflammation scores were found to be in the same order: insulin≥placebo≥catheter. In this experiment, histological analyses indicated that the predominant tissue response to infusion was inflammation.

Figure 2D:
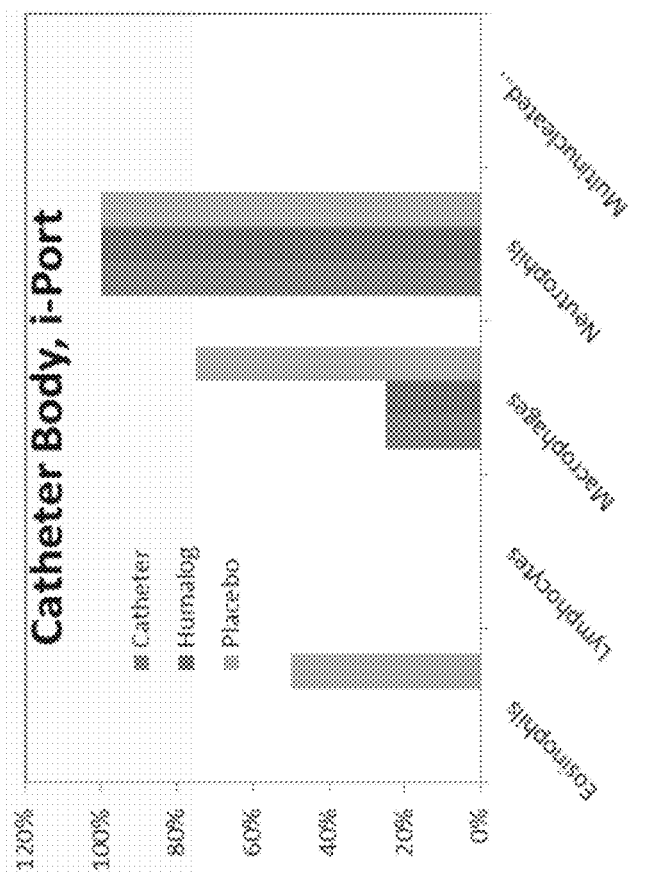
FIG. 2D is a series of graphs illustrating the predominate inflammation cells at the cannula tip and cannula body of an insulin injection port (i-Port™) To isolate the main inflammation contributors, a cannula, a cannula infused with insulin, and a cannula infused with placebo were placed on a diabetic pig. Compared to continuous infusion, the giant cells are missing in the i-Port™ study. Other cell types showed similar reaction to the cannula, cannula infused with insulin (Humalog™), and cannula infused with placebo.
Figure 2D:
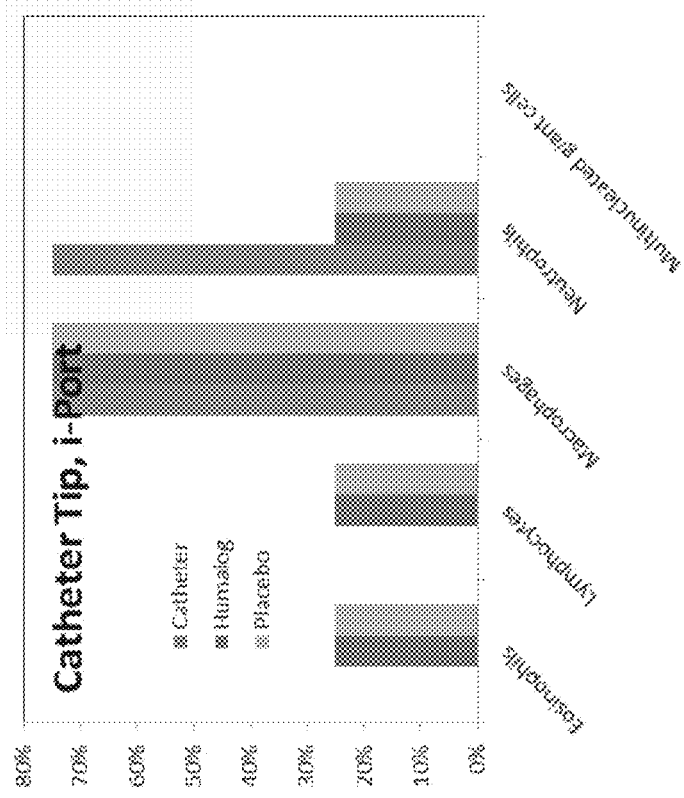

FIG. 2D is a series of graphs illustrating the predominate inflammation cells at the catheter tip and catheter body of an insulin injection port (i-Port™). To isolate the main inflammation contributors, a catheter, a catheter infused with insulin, and a catheter infused with placebo were placed on a diabetic pig. Compared to continuous infusion, the giant cells are missing in the i-Port™ study. Other cell types showed similar reaction to the catheter, catheter infused with insulin (Humalog™), and catheter infused with placebo. As observed by the pathologist, the pigs may have developed a hypersensitivity to the Humalog™ and such a reaction would contribute to the inflammation seen (the degree that hypersensitivity is influencing the inflammation is unclear but it could be one of the main drivers).

In conclusion, site-loss at approximately 3 days had been observed in some of the diabetic pigs (using both i-Port™ and CSII), similar to a human situation. The localized tissue inflammation trended more severe in the diabetic pigs than in the normal pigs. At a higher inflammation score (greater than or equal to 3) or a low inflammation score for a long time, the fat surrounding the catheter tip was replaced by fibrosis. Insulin (Humalog™) was found to be associated with increased localized inflammation. Compared to a catheter and placebo, it is the main contributor to localized tissue fibrosis (the likely factor for site-loss).

By maintaining blood sugar levels with CSII beyond 3-days, possible site-loss mechanisms leading to inflammation were determined. CSII catheter insertion induces an acute inflammatory reaction within epidermis, dermis, and subcutaneous adipose tissue. Insulin absorption into the circulation becomes variable and unreliable over time. The cells and connective tissue along the path of needle/catheter infusion are possibly damaged. Insertion also possibly damages basement membranes, extracellular matrix, and the structural proteins, lymphatic vessels, arterioles, capillaries and venuoles causes blood to accumulate around the catheter shaft. As a result, a layer of physiological debris forms around the CSII catheter, obstructing capillaries.

Example 2: Drug-Adhesive Patch

Table 5 shows examples of steroids, immunosuppressant drugs, cox inhibitors, non-steroidal anti-inflammatory drugs (NSAIDS), and anti-proliferative agents that can be blended in an adhesive and/or penetrant to achieve an anti-inflammatory effect.

TABLE 5

| Drug | Drug Type | Adhesive | Penetrant |
|---|---|---|---|
| Diclofenac | Anti-inflammatory; Nonsteroid | Duro-Tak 387-2287, | Isopropyl palmitate, |
| Celecoxib | Anti-inflammatory; Nonsteroid | Duro-Tak 87-2287, | IPM (Isopropyl Myristate), |
| Rofecoxib | Anti-inflammatory; Nonsteroid | Duro-Tak 87-4287, | Lauryl lactate, |
| Naproxen | Anti-inflammatory; Nonsteroid | Duro-Tak 87-2074 | Triacetin, |
| Piroxicam | Anti-inflammatory; Nonsteroid | | Sorbitan oleate |
| Rapamycin (Sirolimus) | Immunosuppression, Anti-proliferative | | Span ® 80 nonionic surfactant, Propylene Glycol, Triacetin |

Figure 3:
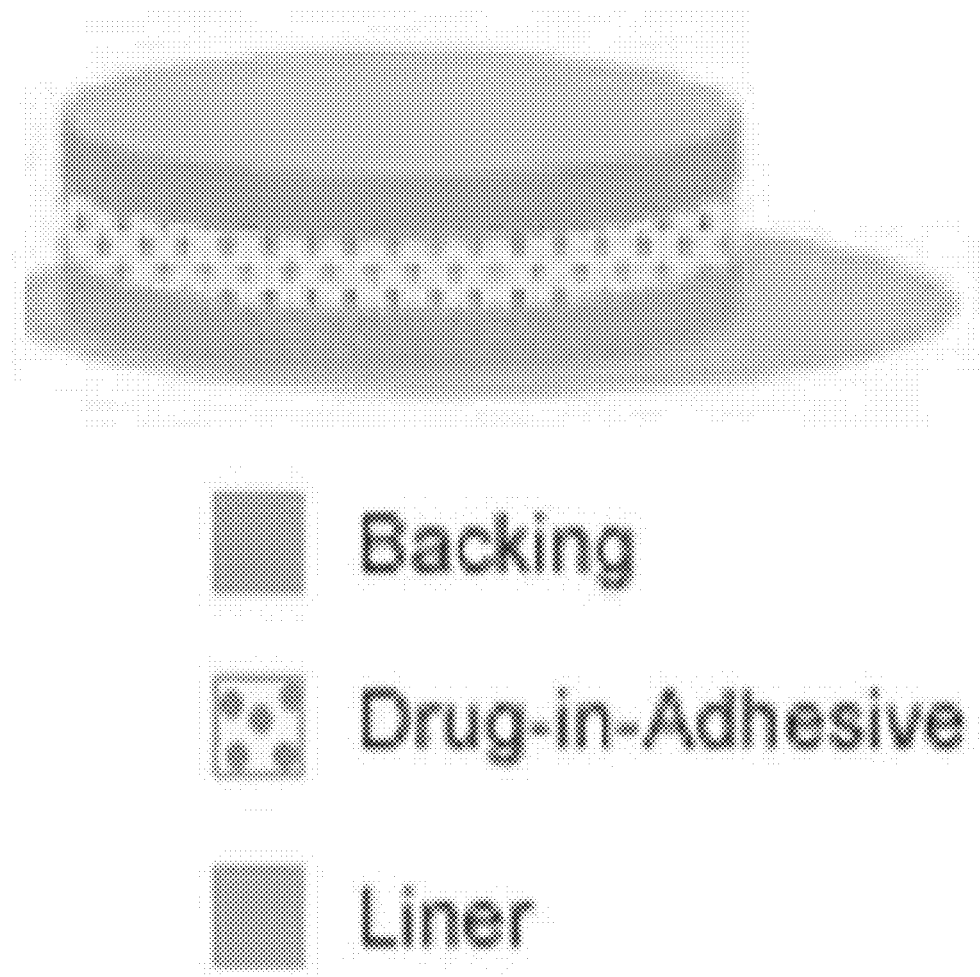
FIG. 3 shows a drug-adhesive patch comprising a matrix system without a rate-controlling membrane.

As shown for example in FIG. 3, a transdermal patch is a medicated adhesive patch that can be placed on the skin for several days depending on the skin type. The medication can penetrate the skin to reduce the inflammation at the subcutaneous injection site. The medicated transdermal adhesive patch can be packaged and sold separately to provide various options for infusion set users.

Example 3: Drug-Coated Cannula

A subcutaneous infusion set normally includes an insertion needle, which is assembled with the soft cannula and is adapted to pierce the patient's skin for transcutaneous cannula placement. The insertion needle is thereafter withdrawn to leave the cannula in place for subcutaneous fluid infusion. Although the materials used for the cannula are typically flexible enough to provide comfort for the patient, the inevitable movement of the cannula that occurs as a patient moves results in inflammation. Where a needle is inserted for cannula placement, an injury is created. The implanted cannula, a foreign body, elicits an exacerbated host response, while greater inflammation occurs as a result of any cannula movement. The situation may be even worse for the hard cannula, which may be the reason why the hard cannula infusion sets have a recommended use-life of 2 days.

Figure 4:
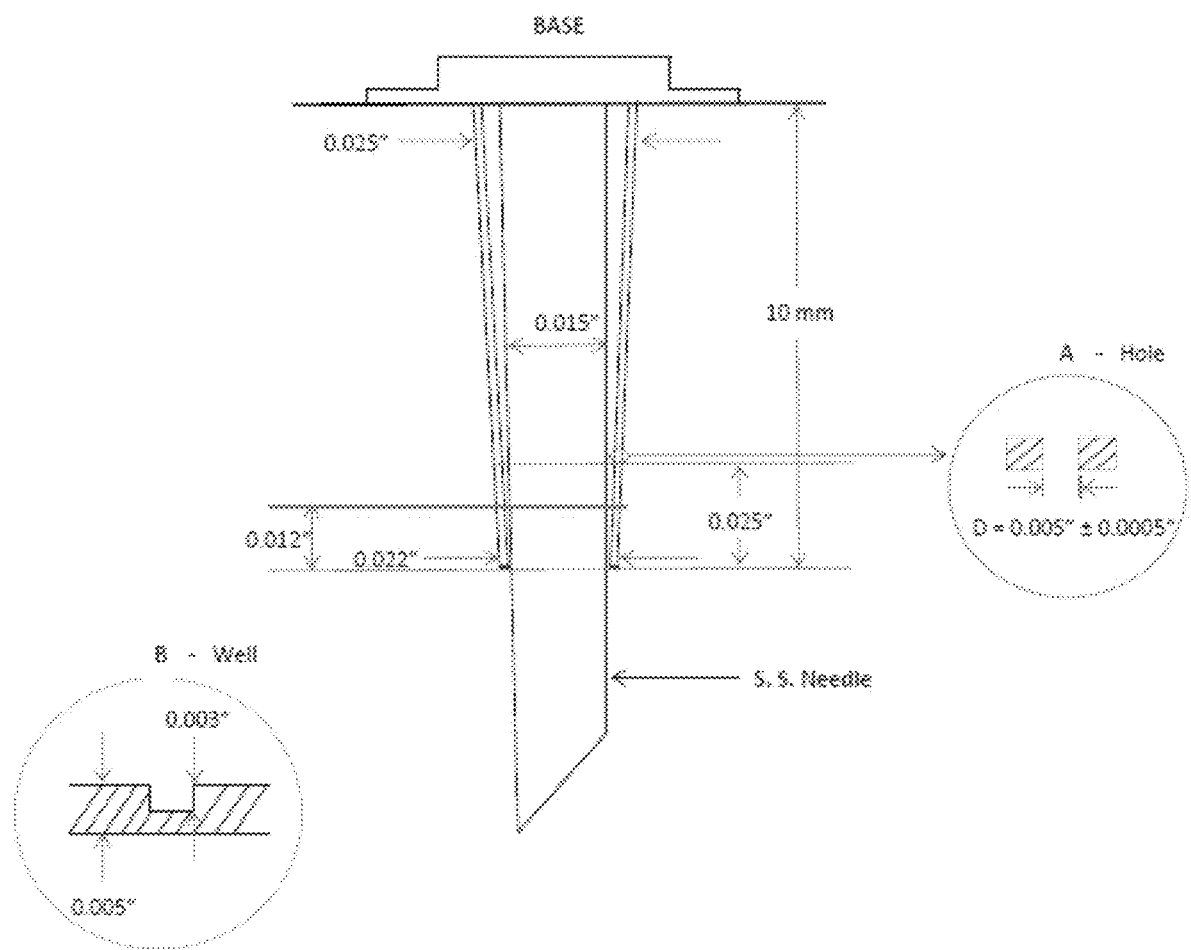
FIG. 4 is a schematic of an exemplary cannula in accordance with one or more embodiments of the invention. The cannula may comprise of (A) holes or (B) wells or a combination of both and can be loaded with or without drugs.

A process/mechanism is also provided for reducing coagulation, inflammation, reducing/inhibiting scar tissue formation, and/or increasing insulin permeability through an obstructed capillary (capillaries that allows insulin diffusion). In particular, an innovative cannula design is provided that mitigates foreign body immune responses, such as site-loss and occlusion. The infusion cannula can be used in conjunction with an infusion set, for delivery of a substance into a subject's internal tissue environment. In one example, an infusion cannula is modified with six different configurations to incorporate holes and wells for loading one or more medicinal agents (see Table 1). The cannula may comprise of (A) holes or (B) wells or a combination of both. FIG. 4 is a schematic of a sample configuration of cannula that can be loaded with or without drugs.

There are various advantages to the cannula design. These cannula designs (incorporated holes and wells) allow providers to gain flexibility of coating and loading controlled release and/or instant release response-inhibiting agents at the same time within one insertion to prevent the development of a foreign body reaction in response to insertion in the subcutaneous tissue. These cannula designs can also reduce the impact of insertion. The microarchitecture of the cannula, particularly at the surface, is an important parameter that influences the host response. Existing cannula can result in densely packed, well-organized fibrous capsules, whereas modified cannula (incorporated holes and wells) lead to a less dense, more open and disorganized fibrous capsule which can reduce the extent of the injury at the insertion site. Furthermore, the cannula design increases infusion sites by increasing the number of holes or ports, thereby lowering pressure at each site which lessens injury. Also, the design increases anchorage so that it prevents movement of the cannula—less movement results in reduced injury and blood clots, infection. In addition, one or more response-inhibiting agents can also be impregnated into these cannula designs for a controlled release of the response-inhibiting agent.

Figure 5:
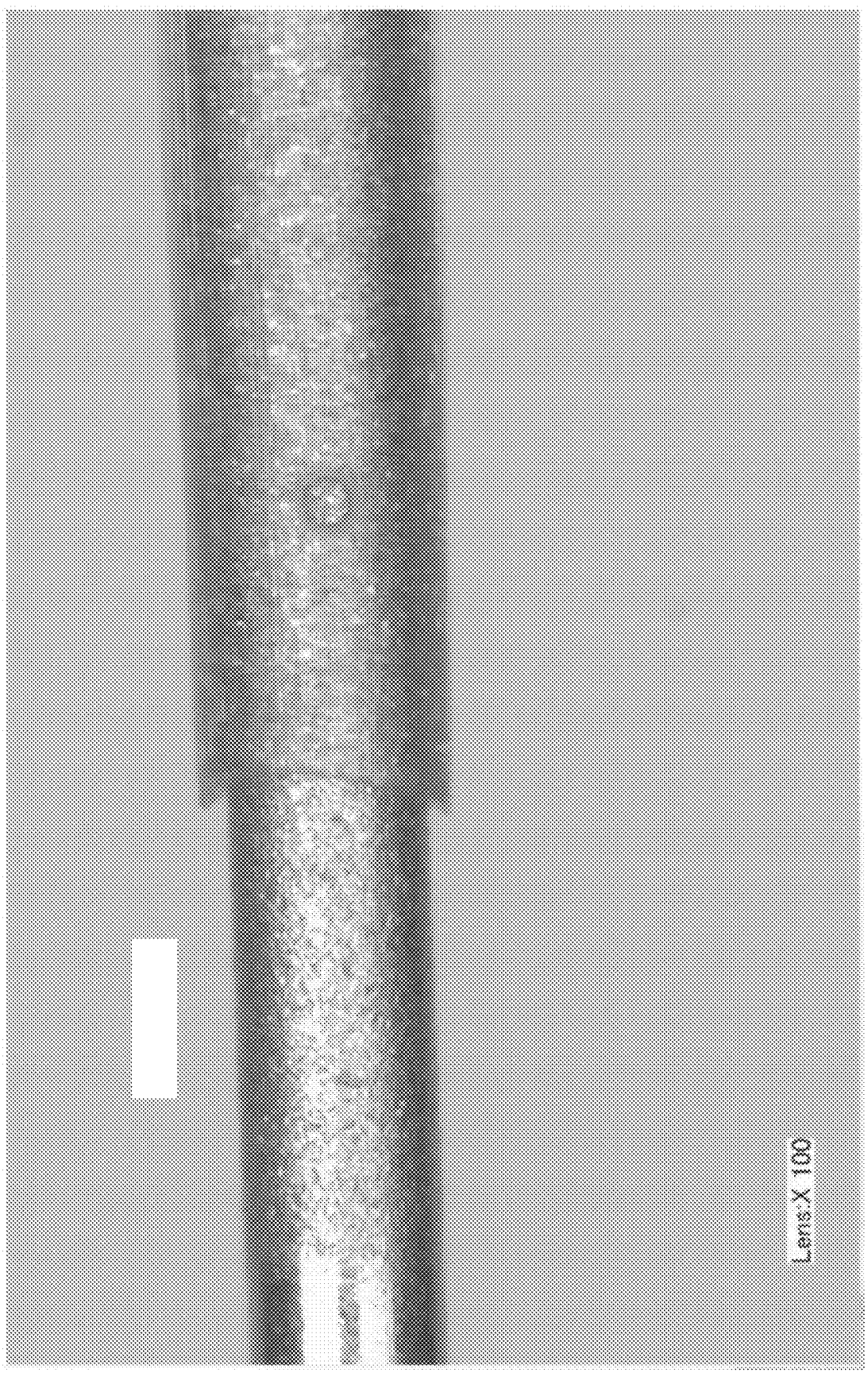
FIG. 5 shows a drug-coated cannula. The cannula material is FEP. Its wall thickness is 0.003"-0.005", inner diameter (ID) is 1.015", outer diameter (OD) at the base is 0.025", and outer diameter at the tip is 0.022".

In certain embodiments, a response-inhibiting agent is further coated onto the lumen or loaded into the well of a cannula to inhibit or reduce an immune response from subcutaneous cannula placement. Table 5 shows examples of steroids, immunosuppressant drugs, cox inhibitors, non-steroidal anti-inflammatory drugs (NSAIDS), and anti-proliferative agents that can be blended in the coating to achieve an anti-inflammatory effect. In another embodiment, the response-inhibiting agent provides an anti-coagulation effect. Additional medicinal agents, such as a steroid, immunosuppressant drug, cox inhibitor, NSAID or anti-proliferative drug, can be coated onto the lumen or loaded into the well of a cannula to achieve a further immune response inhibiting/reducing effect of subcutaneous cannula placement. FIG. 5 shows an example of a drug-coated cannula. In this exemplary implementation, the cannula material is FEP. Its wall thickness is 0.003"-0.005", inner diameter (ID) is 1.015", outer diameter (OD) at the base is 0.025", and outer diameter at the tip is 0.022".

Example 4: Reservoir and Infusion Tube Design

One or more embodiments of the invention include having a dual reservoir for dual infusion of two drugs, insulin and a response-inhibiting agent. In a separate design, the infusion tube is lined (impregnated) with a response-inhibiting agent to reduce site-loss and/or occlusion.

Drug formulation (in conjunction with insulin and an infusion set) is an important aspect to extending infusion set wear. Table 6 below shows examples of steroids, immunosuppressant drugs, cox inhibitors, non-steroidal anti-inflammatory drugs (NSAIDS), and anti-proliferative agents that can be mixed with the fluid medication, e.g. insulin formulation, (either pre-mixed or delivered separately at the infusion site) to achieve a further anti-inflammatory effect.

TABLE 6

| Drug Formulation | Type |
| --- | --- |
| Rapamycin (Sirolimus) mixed with Insulin Formulation | Immunosuppression (and anti-proliferative)/Insulin |
| Diclofenac Sodium mixed with Insulin Formulation | Anti-inflammatory; Nonsteroid/Insulin |
| Celecoxib mixed with Insulin Formulation | Anti-inflammatmy; Nonsteroid/Insulin |
| Rofecoxib mixed with Insulin Formulation | Anti-inflammatmy; Nonsteroid/Insulin |
| Naproxen Sodium mixed with Insulin Formulation | Anti-inflammatory; Nonsteroid/Insulin |
| Piroxicam mixed with Insulin Formulation | Anti-inflammatmy; Nonsteroid/Insulin |

Example 5: Extended Wear Infusion Set Study Using a Porcine Model

The objectives of this study include duplicating the site-loss phenomena observed in previous studies using a diabetic porcine model. Additionally, various infusion set configurations are evaluated for reducing site-loss and extending infusion set wear. Further, site-loss is mitigated using a response-inhibiting agent and/or infusion pump to increase reliability of wear for 3 days and extend infusion set wear beyond 3 days.

Reduction of foreign body response is accomplished by a drug impregnated infusion set (more specifically, at the cannula), through either continuous elution or drug depots. The cannula design provided reduces site-loss and/or occlusion through the use of a response-inhibiting agent. Table 7 shows the examples of various infusion configurations used in this study.

TABLE 7

Current Executed Site-Loss Study Design

| Trial | Infusion Set Configuration | Infusate |
| --- | --- | --- |
| T1 | Sof-Set | U100 Humalog ™ |
| T2 | Sof-Set | U100 Humalog ™ |
| T3 | Polymeric Cannula Infusion Set | U100 Humalog ™ |
| T4 | Polymeric Cannula Infusion Set | U100 Humalog ™ |
| T5 | 90° Polyfin (Modified Polyfin) | U100 Humalog ™ |
| T6 | 90° Polyfin (Modified Polyfin) | U100 Humalog ™ |
| T7 | 90° Polyfin (Modified Polyfin) | U100 Humalog ™ formulated with BSP |
| T8 | Sof-Set | U100 Humalog ™ with Rapamycin |
| T9 | Drug Coated Sof-Set (Drilled hole) | U100 Humalog ™ |
| T10 | Sof-Set | U100 Humalog ™ formulated with DXP |
| T11 | Drug Coated Sof-Set (Direct Coat) | U100 Humalog ™ |
| T12 | Sof-Set | U100 Humalog ™ with Pre-dose Rapamycin |
| T13 | Sof-Set | U100 Humalog ™ with Pre-dosed/Pre-mixed Rapamycin |
| T15 | Sof-Set | U100 Humalog ™ with Pre-dosed/Pre-mixed Rapamycin |
| T16 | Sof-Set with Rapamycin Coated Cannula | U100 Humalog ™ |
| T17 | Sof-Set | U100 Humalog ™ with Pre-dosed/Pre-mixed Rapamycin |

TABLE 7-continued

Current Executed Site-Loss Study Design

| Trial | Infusion Set Configuration | Infusate |
|---|---|---|
| T18 | Sof-Set | U100 Humalog™ with Pre-dosed/Pre-mixed Rapamycin |
| T19 | Sof-Set | U100 Humalog™ with Pre-dosed hyaluronidase or Tacrolimus |
| T20 | Sof-Set with BDP or Rapamycin Coated Cannula | U100 Humalog™ |
| T21 | Modified Polyfin Prototype | U100 Humalog™ with or without Pre-mixed Rapamycin |
| T22 | Sof-Set | U100 Humalog™ with Pre-dosed hyaluronidase or Rapamycin |
| T23 | Metallic cannula infusion set | U100 Humalog™ with or without pre-dosed Rapamycin |
| T24 | Sof-Set with Silver Coated Cannula | U100 Humalog™ |
| T25 | Sof-Set | U100 Humalog™ with pre-mixed hyaluronidase |
| T26 | Sof-Set | U100 Humalog™ with pre-mixed hyaluronidase |
| T27 | Sof-Set | U100 Humalog™ with pre-dosed Rapamycin or pre-mixed Heparin |
| T28 | Sof-Set | U100 Humalog™ with bolus-dosed Rapamycin |
| T29 | Sof-Set | U100 Humalog™ with pre-mixed Heparin |
| T30 | Sof-Set | U100 Humalog™ with bolus-dosed hyaluronidase |
| T31 | Modified Polyfin Prototype | U100 Humalog™ |
| T32 | Sof-Set | U100 Humalog™ with pre-mixed Heparin |
| T33 | Polyfin w/o Rapamycin Coated Cannula | U100 Humalog™ |
| T34 | Sof-Set | U100 Humalog™ with pre-mixed Heparin |
| T35 | Sof-Set | U100 Humalog™ with pre-mixed Heparin |
| T36 | Sof-Set w PC-Rapamycin Coated Cannula | U100 Humalog™ |
| T37 | Sof-Set w Heparin Coated Cannula | U100 Humalog™ |
| T38 | Sof-Set with Low Dose Heparin Depot | U100 Humalog™ |
| T39 | Polymeric Cannula Infusion Set with Anti-fouling Coating or Polymeric Cannula Infusion Set | U100Humalog™ or U100 Humalog™ with pre-mixed Dextran Sulfate |
| T40 | Polymeric Cannula Infusion Set with Anti-fouling Coating or Polymeric Cannula Infusion Set | U100 Humalog™ or U100 Humalog™ with pre-mixed Dextran Sulfate |
| T41 | Polymeric Cannula Infusion Set/Polyfin with Anti-fouling Coating | U100 Humalog™ |
| T42 | Polyfin with Anti-fouling Coating or Sof-Set | U100 Humalog™ or U100 Humalog™ with bolus-dosed BSP/DSP |
| T43 | Metallic cannula infusion set w Silver coated cannula or Polyfin w. Heparin Depot | U100 Humalog™ |
| T44 | Metallic cannula infusion set/Sof-Set with Anti-fouling coating | U100 Humalog™ |
| T45 | Polymeric Cannula Infusion Set with Heparin Depot | U100 Humalog™ |
| T46 | Polymeric Cannula Infusion Set w/o Heparin Depot | U100 Novolog™ |
| T47 | Polymeric Cannula Infusion Set with Heparin Depot | U100 Novolog™ |
| T48 | Polymeric Cannula Infusion Set | U100 Novolog™ |
| T49 | Polymeric Cannula Infusion Set | U100 Novolog™ |
| T50 | Polymeric Cannula Infusion Set | U100 Novolog™ |

BSP = Betamethasone Sodium phosphate; DXP = Dexamethasone Phosphate
Rapamycin, also known as Sirolimus, has have potent immunosuppressive and antiproliferative properties Site-loss phenomenon was duplicated for the Sof-Set™ infusion set at Sinclair using a diabetic porcine model. Compared to the Polymeric Cannula Infusion Set/Sof-Set™ infusion set (available from Medtronic™), the 90° Polyfin™ infusion set with stainless steel needle indicated site-loss much quicker (less than or equal to 3 days). Also, erythema and/or edema were observed on all the pigs. Three drugs (BSP, DXP, and Rapamycin) were evaluated for dosing with Humalog™. Rapamycin indicated signs of improvement, indicated by recovery after around 6 days.

Example 6: Effect of Infusion Set Design and Pharmaceuticals on Site-Loss

Figure 6:
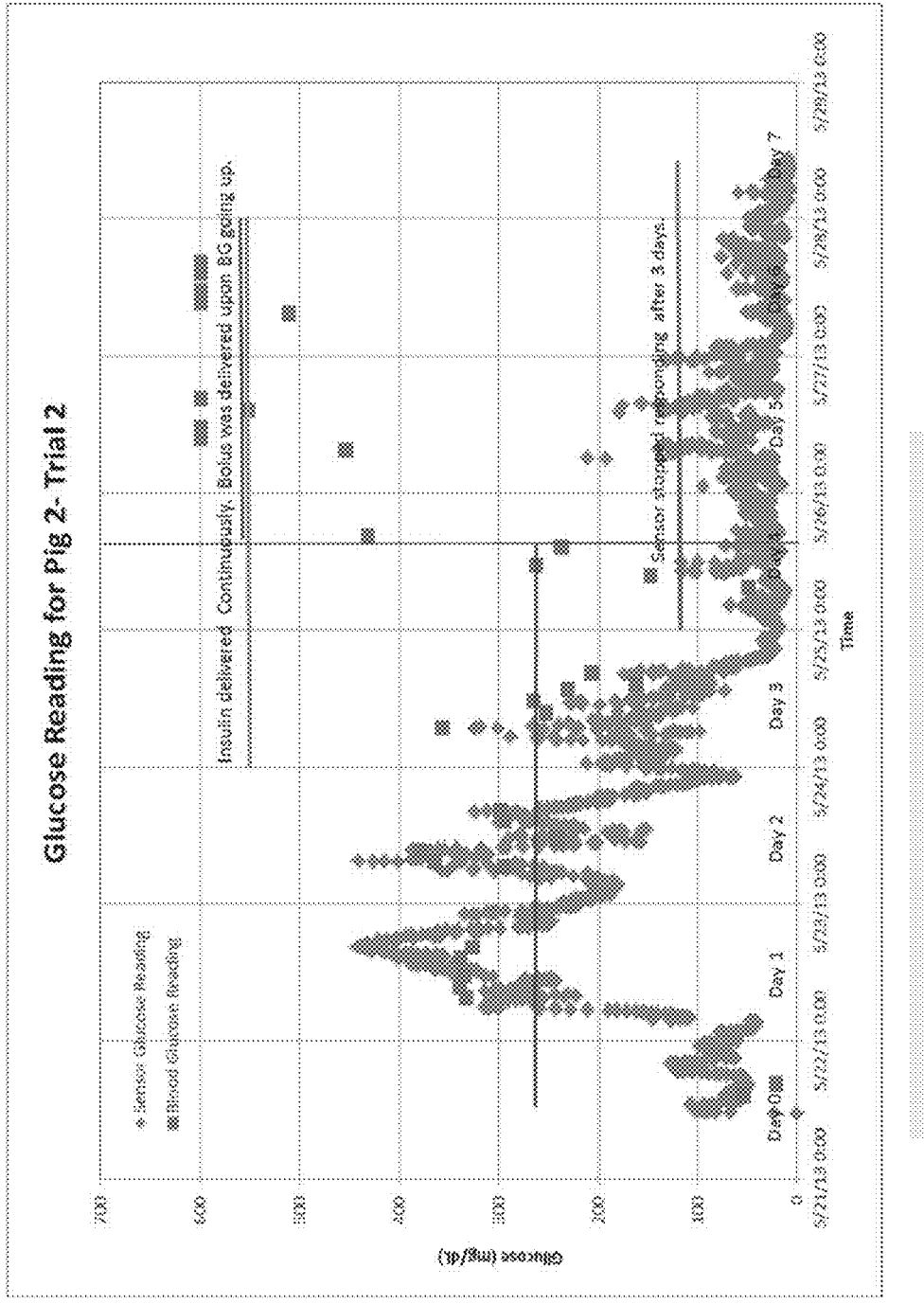
FIG. 6 is a graph of blood glucose (BG) vs. time for normal site-loss. Based on the glucose reading for pig 2, the infusion site was lost after glucose level increased.

Extended wear infusion sets are provided that increase primary therapy clinical outcomes by increasing the reliability of current label use to 3 days and increasing wear duration to 6 days. Continuous subcutaneous insulin infusion (CSII) is an effective method for diabetic care. Local site reaction/site-loss (at around 3 days) are often encountered clinically, yet poorly understood. Causes of site-loss are poorly understood, which may be due to localized coagulation, occlusion, inflammation or scar tissue formation. A diabetic porcine model was developed to understand the cause through a time-based biopsy study. The study results suggest that localized immune response to cannula insertion and insulin delivery might play an important role in site-loss. FIG. 6 is an example of site-loss in a diabetic porcine model, which shows that the infusion site was lost after glucose levels increased.

The objectives of this study include: duplicating the site-loss phenomena observed in previous studies using the diabetic porcine model; using the established diabetic porcine model to evaluate the effects of various infusion set designs on infusion site-loss; and testing if site-loss can be mitigated by direct pump infusing of immunosuppressant/anti-inflammatory drugs, and/or by modifying infusion set by drug coating. Table 8 shows various information regarding 4 diabetic pigs randomly assigned to wear one infusion set.

TABLE 8

Study Design

| Information | Diabetic Pig ID (All Male) | | | |
|---|---|---|---|---|
| | 4846-IM1 | 4706-IM2 | 4729-IM3 | 4856-IM4 |
| Birth Date | 11 Aug. 12 | 1 Jul. 12 | 5 Jul. 12 | 12 Aug. 12 |
| Diet, g/meal (2 meals/day) | 400 | 300 | 300 | 300 |
| Initial Weight (kg, 5/13) | 26.6 | 27.3 | 26.6 | 29.7 |
| Weight (kg, 8/27) | 31.6 | 31.5 | 30.3 | 31.7 |

Figure 8:
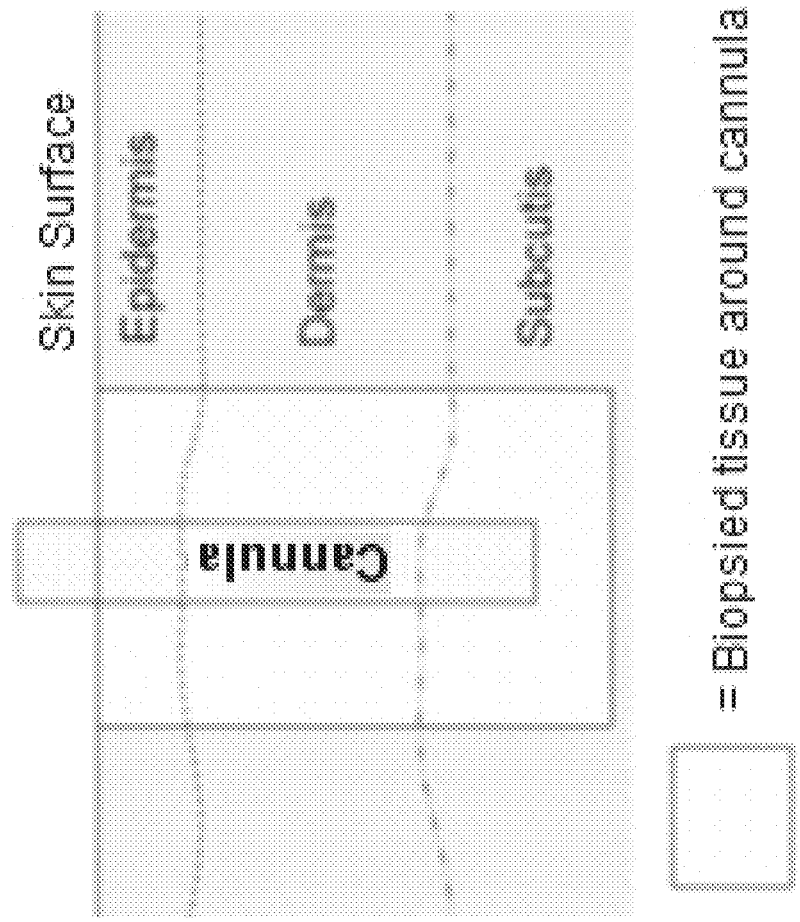
FIG. 8 is an illustration of the infusion site and the biopsied tissue around the cannula.
Figure 9:
FIG. 9 shows the infusion set and sensor placement in the set-up of this experiment (in the order of steps (a) to (d)).
Figure 9:
Figure 9:
Figure 9:

This study is designed so that each set (inserted under anesthesia) is to be worn for 1 week unless there was set failure/dislodge. Glucose is monitored by a blood glucose meter and Enlite™ sensor. The criteria for determining site loss is that blood glucose is greater than 350 mg/dl and fails to decrease following an insulin dose correction. During biopsy pumps are removed but the cannula is maintained in-situ. Site skin is examined for edema/erythema (swell/redness) (see FIG. 8). FIG. 9 shows the infusion set and sensor placement in the set-up of this experiment.

Table 9 below shows the initial results for various immunosuppressant/anti-inflammatory formulations delivered by Sof-Set™. Unexpectedly, not all immunosuppressant/anti-inflammatory formulations had a positive effect in extending the duration of wear before site-loss occurred. The formulation of insulin (Humalog) with BSP or DXP actually resulted in the onset of site-loss much earlier, performing worse than the control. However, the formulation of insulin (Humalog) with rapamycin notably extended the duration of wear to 5 days, unexpectedly performing better than the control.

TABLE 9

Initial Results for Various Formulations

| Formulation | Effect on Site-Loss | Other Observations | |
|---|---|---|---|
| U100 Humalog with 200 µg/mL BSP (Betamethasone Sodium Phosphate) | Site-Loss after 1 day for all pigs using 90° Polyfin™ Worse than Control | Animal ID 1M1: 4846 1M2: 4706 1M3: 4729 1M4: 4856 | Draize Score (erythema/edema) 0/3 0/1 1/0 1/0 |
| U100 Humalog with 200 µg/mL DXP (Dexamethasone Phosphate) | Site-Loss after 1 day for 2 pigs using Sof-Set™ Worse than Control | Animal ID 1M1: 4846 1M2: 4706 1M3: 4729 1M4: 4856 | Draize Score (erythema/edema) 1/0 1/0 1/0 1/0 |
| U100 Humalog with 20* ug/mL Rapamycin | Site-Loss after 5 days for 1 pigs using Sof-Set™ Better than Control | No erythema (skin redness) or edema (skin swell) was observed | |

*Rapamycin was later found to be degraded by assaying solution after use.

Table 10 below shows the results of further studies regarding various rapamycin dosing regimen delivered by Sof-Set™. Notably, not all rapamycin dosing strategies resulted in a delayed occurrence of site-loss. Formulations 3, 4, and 5 in Table 10 were equal or better than the control. No erythema/edema was observed in any formulation.

TABLE 10

Preliminary Results: Rapamycin Dosing by Sof-Set™

| Formulation | Pre-Dosing | Continued Infusing | Site Loss Observed |
|---|---|---|---|
| 1 | ~35 µg of Rapamycin | ~10 µg/mL Rapamycin in U100 Humalog | Site Loss 1-2 days |
| 2 | >7 µg of Rapamycin | ~5 µg/mL Rapamycin in U100 Humalog | Site Loss 2-3 days |
| 3 | Cannula coated with 50 µg Rapamycin or 2.43 µg Rapamycin + 6.38 µg BDP; infused with U100 Humalog | | Site Loss 3-5 days |
| 4 | No | <2 µg/mL Rapamycin in U100 Humalog | Site Loss ≥ 5 days |
| 5 | ~3 µg of Rapamycin at Day 0 and Day 3 | U100 Humalog | No Site Loss in 6 days |

Figure 10:
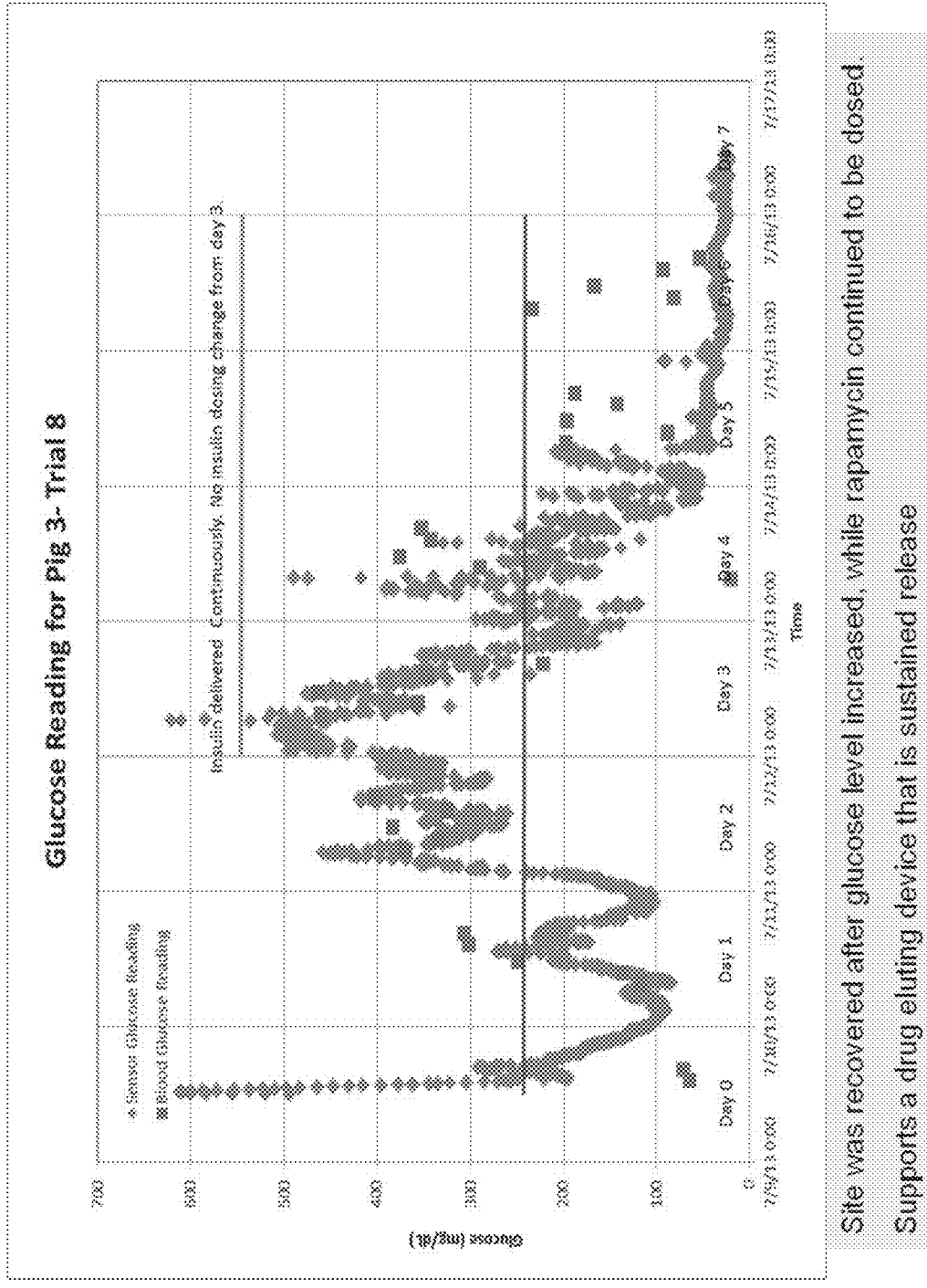
FIG. 10 is a graph of blood glucose (BG) vs. time for Sof-Set™ with rapamycin dosed-insulin. The infusion site was recovered after glucose level increased, while rapamycin continued to be dosed. These results support a drug-eluting device that is sustained release.

FIG. 6 is a graph of blood glucose (BG) vs. time for normal Sof-Set™ site-loss. The infusion site was lost after glucose level increased. FIG. 10 is a graph of blood glucose (BG) vs. time for Sof-Set™ with rapamycin dosed-insulin. The infusion site was recovered after glucose level increased, while rapamycin continued to be dosed. These results support a drug-eluting device that is sustained release.

Observations of site-loss at approximately 3 days for Sof-Set™/Polymeric Cannula Infusion Set in a diabetic porcine model have been repeated in this study. Compared to a Teflon™ cannula, a stainless steel cannula (Polyfin™) had site-loss at a slightly shorter time. Pharmaceuticals have a large impact on insulin infusion site-loss in the diabetic porcine model. Whether directly infused with insulin or coated on the cannula, the immunosuppressant/anti-inflammatory drug rapamycin showed site-loss mitigation.

Example 7: Effect of Insulin/Heparin Infusion Set on Site-Loss

Figure 13:
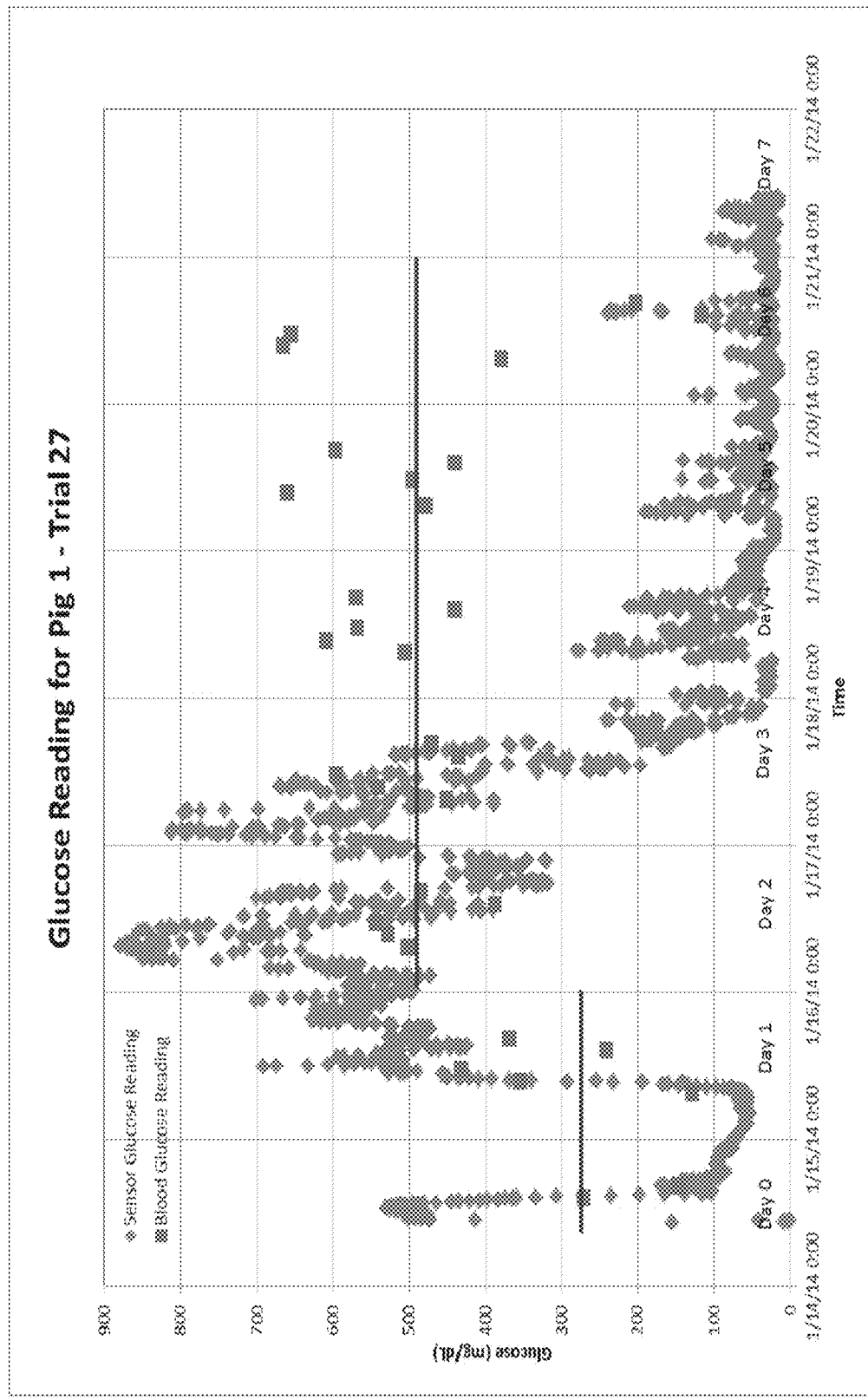
FIG. 13 is a graph of the control results for pig IM1, which shows that site-loss occurred in 2 days.

The objectives of this study include examining site-loss mitigation when heparin is used in continuous infusion along with insulin. U100 of an insulin Humalog was added with 4 mg/mL heparin sodium (purchased from Fisher™, 193 U/mg) and filtered. The actual heparin concentration was 3.55 mg/mL or 685 U/mL. The dosing scheme for pigs 3 and 4 (IM3 and IM4, respectively) are shown in Table 11 below. Based on the glucose monitoring results for IM3 and IM4 (shown in FIGS. 11 and 12, respectively), no site-loss occurred in 6 days. Control results for pig 1 (IM1) indicated site-loss in 2 days (FIG. 13).

TABLE 11

The Humalog dosing scheme

| Time Point | 1M3: 4729 | 1M4: 4856 |
|---|---|---|
| 0:00 | 0.8 U/hr | 0.8 U/hr |
| 7:30 | 6.0 U/hr | 6.0 U/hr |
| 8:00 | 0.7 U/hr | 0.7 U/hr |
| 14:30 | 6.0 U/hr | 6.0 U/hr |
| 15:00 | 0.7 U/hr | 0.7 U/hr |
| Total | 22.85 U | 22.85 U |

Example 8: Usage of Heparin for an Extended Wear Infusion Set

A heparin/insulin co-infusion system is developed to extend infusion set wear. With extended wear, the site of infusion is available for a longer period of time for insulin absorption to lower a blood glucose level. The co-infused heparin has various functions, including: 1) mitigating tissue immune-response to the insertion cannula/needle and infused insulin; 2) stabilizing insulin and preventing localized insulin aggregation; and 3) increasing insulin absorption into blood circulation.

Figure 16:
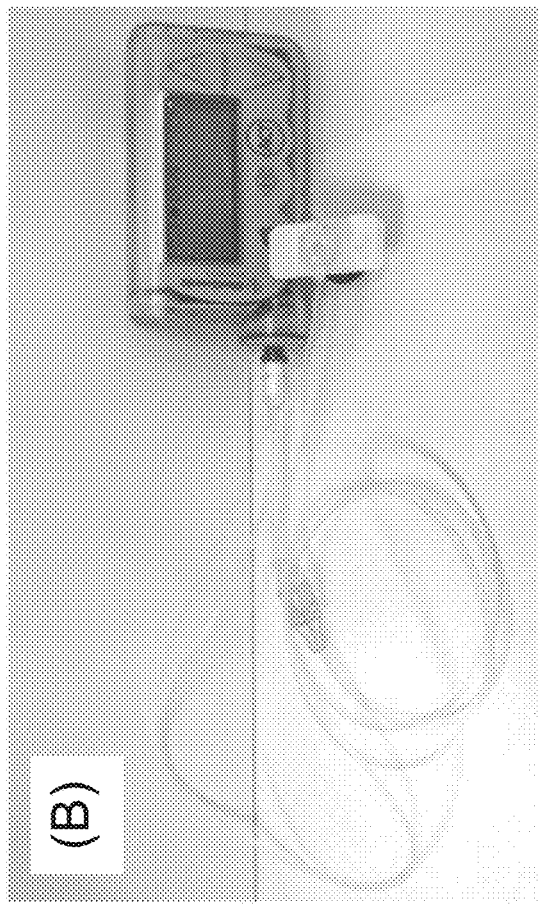
FIG. 16 is an illustration of a heparin reservoir (A) and heparin depots (B-D), in accordance with one or more embodiments of the invention.
Figure 16:
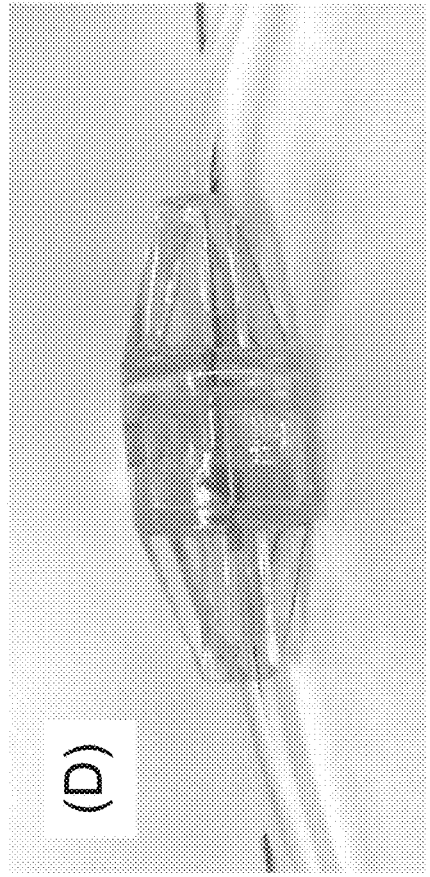
Figure 16:
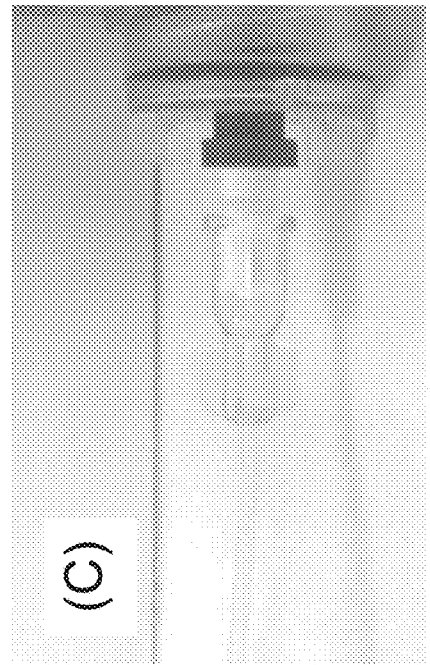
Figure 17:
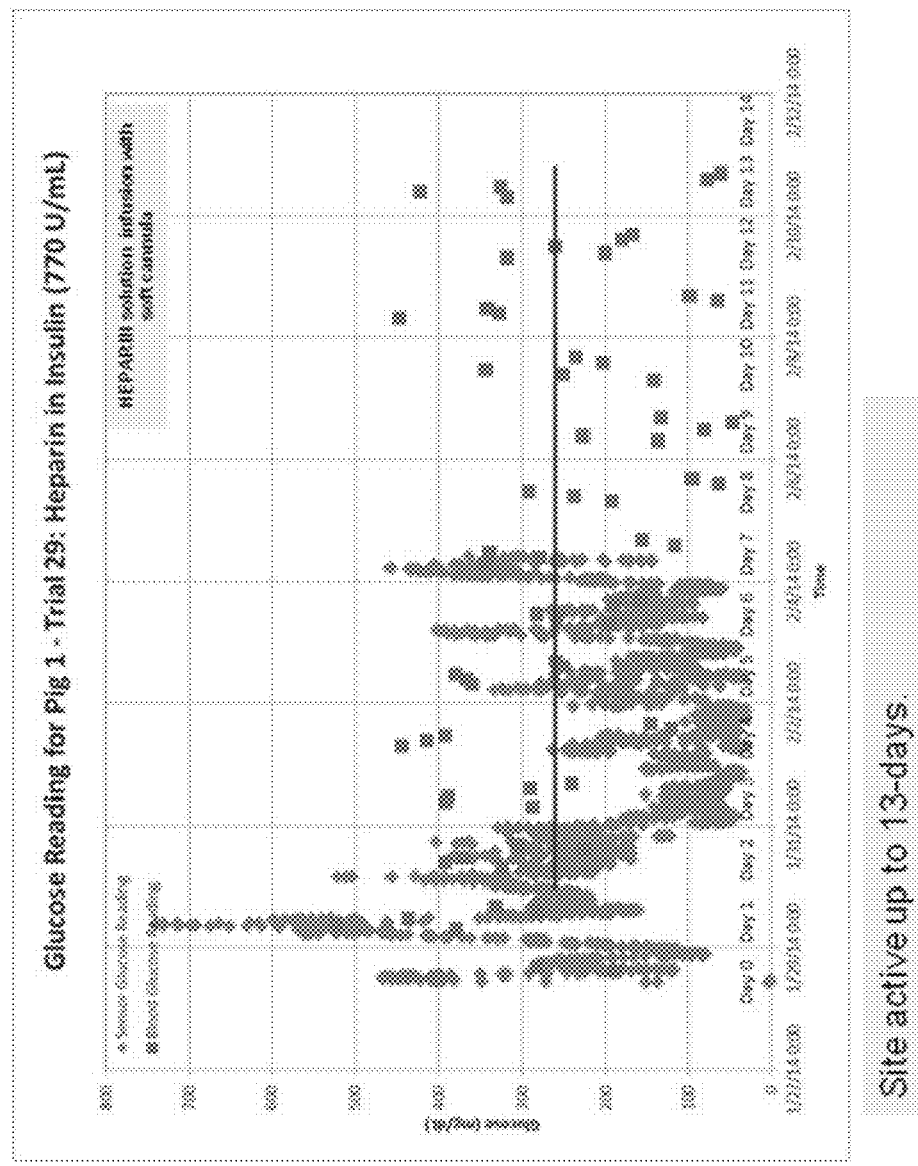
FIG. 17 is a graph of blood glucose (BG) vs. time for Sof-Set™ with heparin dosed insulin, which shows that the infusion site was active up to 13 days.
Figure 18:
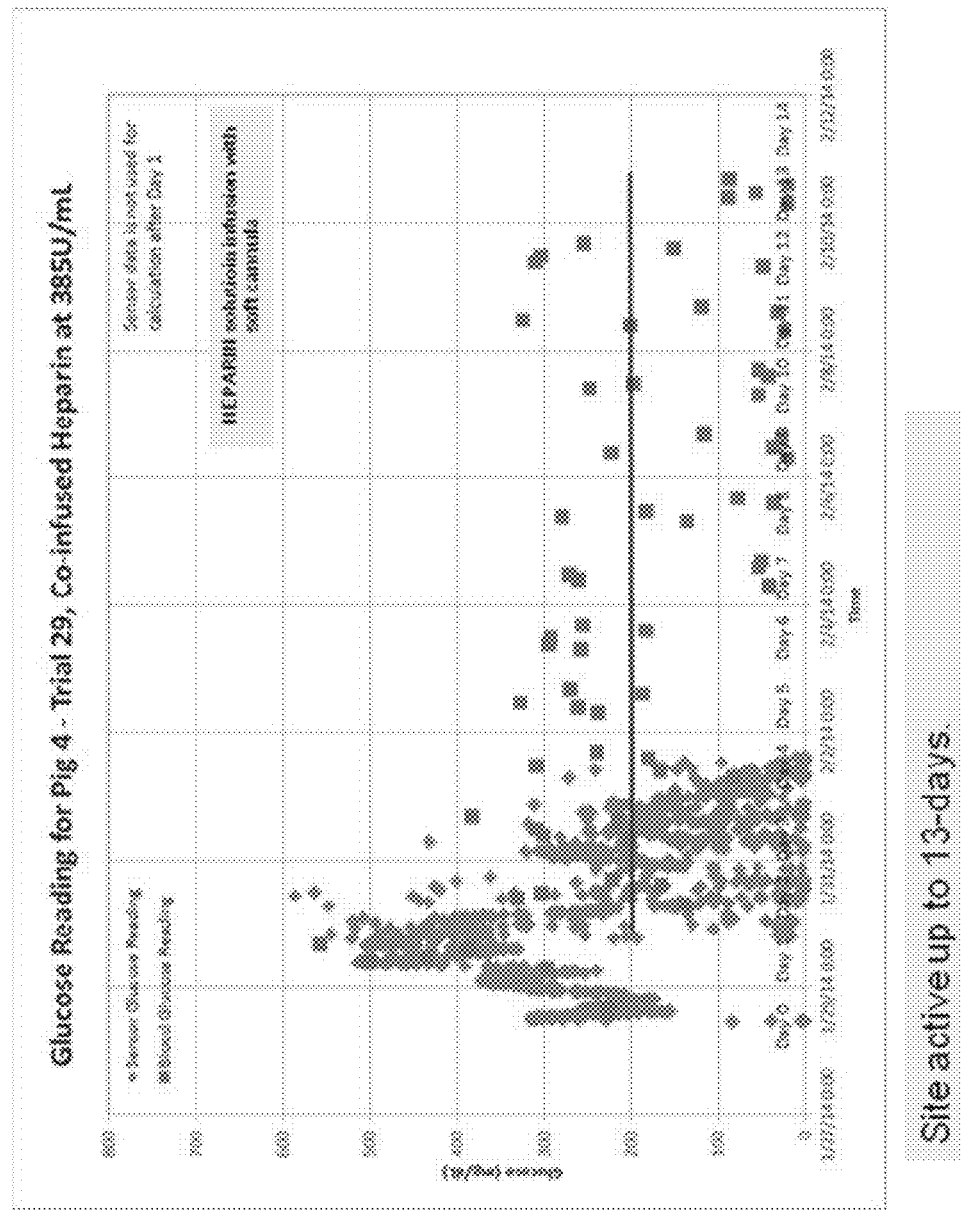
FIG. 18 is a graph of blood glucose (BG) vs. time for Sof-Set™ with heparin dosed insulin, which shows that the infusion site was active up to 13 days.

In one or more embodiments, the heparin acts as an active response-inhibiting agent. In one embodiment, a heparin reservoir is provided, wherein the heparin is pre-filled with insulin as a reservoir and re-fill bottle (as shown, for example, in FIG. 16A). This may be a pre-mix (where heparin and insulin is mixed previously) or an in-situ mix (where heparin and insulin are delivered from two different reservoirs). Original testing using the prefilled heparin/insulin with a Sof-Set™ infusion set resulted in no site loss for greater than 13 days, with a heparin dosing of 100-800 U/mL insulin (U100). No local toxicity was observed. FIG. 6 is a graph of blood glucose (BG) vs. time for normal Sof-Set™ site-loss. FIGS. 17 and 18 are graphs of blood glucose (BG) vs. time for Sof-Set™ with heparin dosed insulin, which both show that the infusion site was active up to 13 days.

Figure 19:
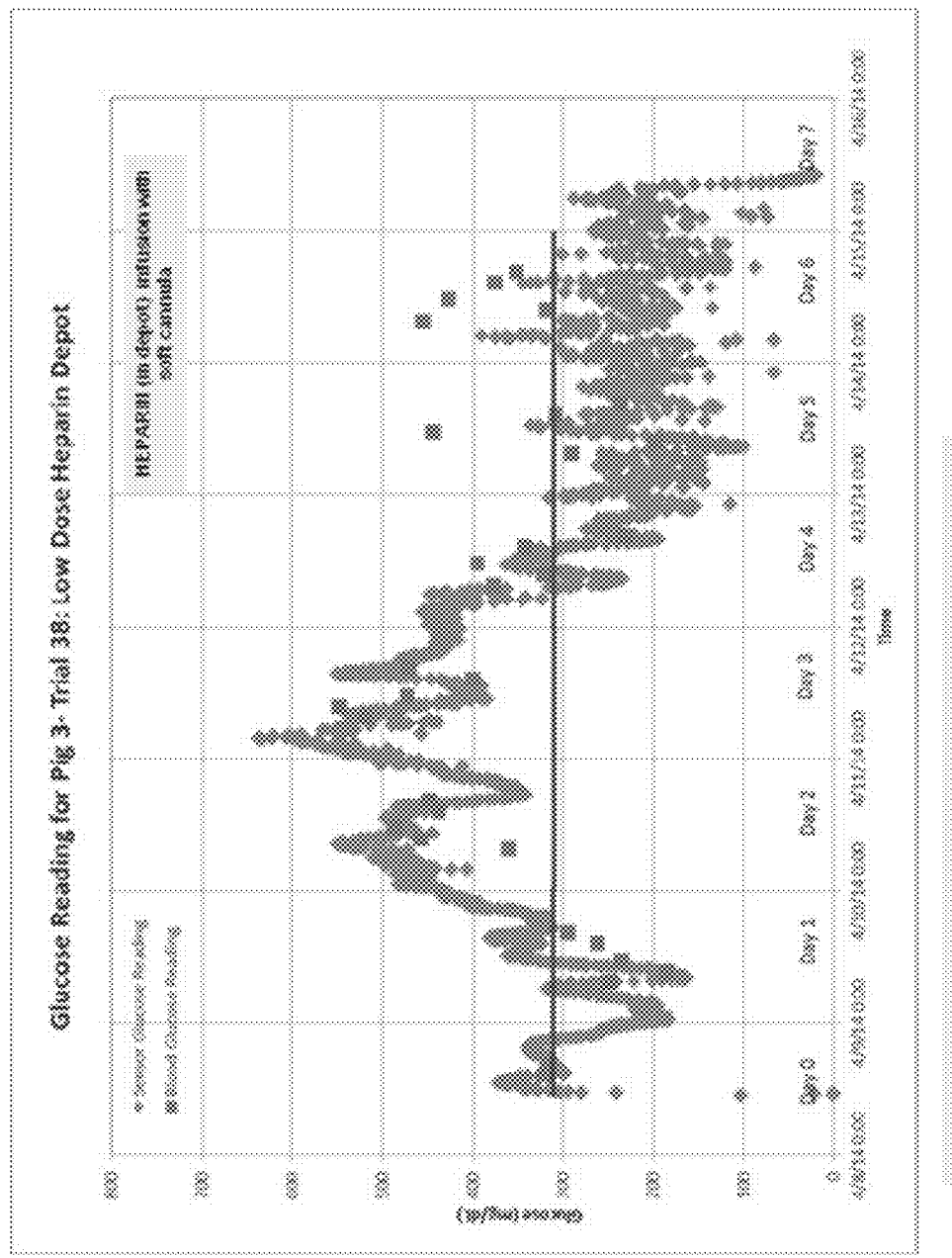
FIG. 19 is a graph of blood glucose (BG) vs. time for Sof-Set™ with a low dose heparin depot, which shows that the infusion site was active up to 6 days.
Figure 20:
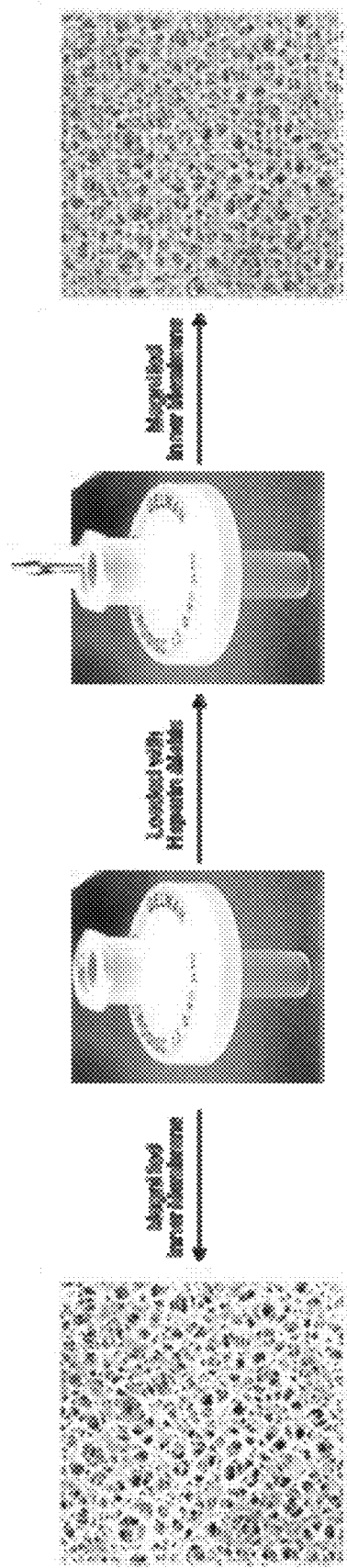
FIG. 20 a detailed structure for an illustrative heparin depot.
Figure 21:
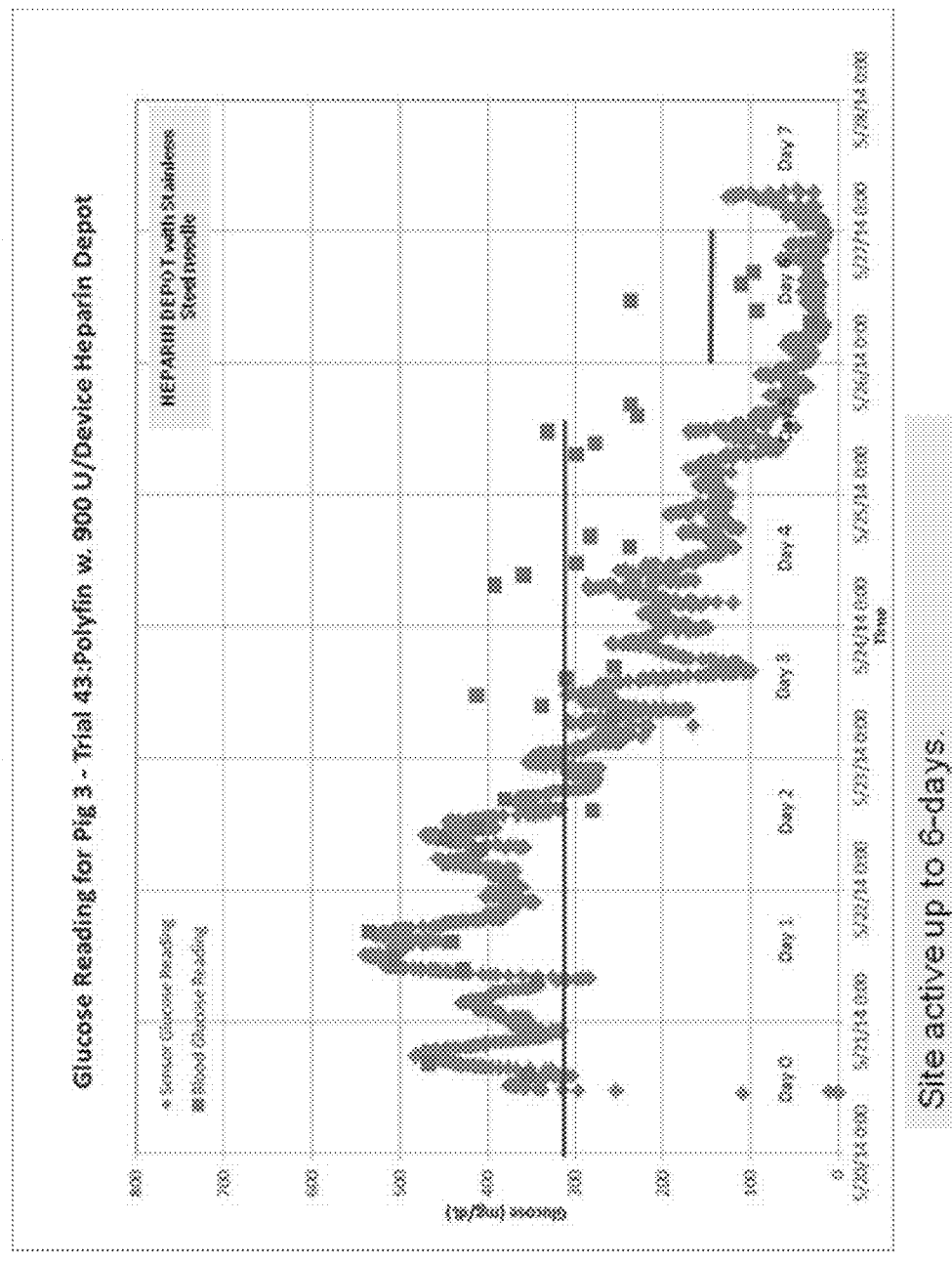
FIG. 21 is a graph of blood glucose (BG) vs. time for Sof-Set™ with a high dose heparin depot, which shows that the infusion site was active up to 6 days.

In another embodiment, an in-line heparin depot is provided for continuous heparin delivery, which can be attached to specific components (e.g. reservoir or each portion of the infusion set). The depot may be attached to various sections of the pumping fluid path in various forms. The attachment may be a filter, plug, sponge, etc. FIGS. 16B-D provide various examples of depots. In accordance with one aspect of the invention, FIG. 20 provides a detailed structure for a heparin depot. The function of the filter membrane is the provide structure support for heparin/matrix loading and to provide a filter to eliminate particulate matters (microbes or aggregates) in the insulin formulation. The function of the matrix is to control heparin release in the infused insulin solution. An initial heparin depot with 100-400 U/device demonstrated the efficacy in extending infusion set wear in diabetic porcine model from around 3 days (control) to 6 days. Table 12 below shows various heparin dosing attempted in this illustrative experiment. In certain embodiments, heparin dosing is 50 U-2000 U per device, 1 U-2000 U per day. A higher dose with different release profiles may also be used. FIG. 19 is a graph of blood glucose (BG) vs. time for Sof-Set™ with a low dose heparin depot, which shows that the infusion site was active up to 6 days. FIG. 21 is a graph of blood glucose (BG) vs. time for Sof-Set™ with a high dose heparin depot, which shows that the infusion site was active up to 6 days.

TABLE 12

Heparin Dosing Attempted

| Heparin Concentration U/mL | Daily Dose (U) | 6-day Total Dose (U) |
|---|---|---|
| 769 | 231 | 1384 |
| 385 | 116 | 693 |
| 192 | 58 | 346 |
| 96 | 29 | 173 |
| 76 | 23 | 137 |
| 60 | 18 | 108 |
| 48 | 14 | 86 |
| 24 | 7 | 43 |

In one or more other embodiments, an immobilized heparin coating on an insertion cannula/needle (surface modification) is also developed to extend infusion set wear by mitigating tissue immune-response to the insertion cannula/needle. In one embodiment, the heparin is immobilized as a non-fouling coating. The preferably durable coating may be spray-coated, dip-coated, or chemically cross-linked on the cannula/needle or any part of the infusion set or the reservoir. In certain embodiments, the heparin coating improves extended wear beyond 6 days.

Example 9: Usage of Dextran for an Extended Wear Infusion Set

A dextran/insulin co-infusion system is developed to extend infusion set wear. With extended wear, the site of infusion is available for a longer period of time for insulin absorption to lower a blood glucose level. The co-infused dextran has various functions, including: 1) stabilizing insulin and preventing localized insulin aggregation; 2) increasing insulin absorption into blood circulation by being anti-thrombotic; and 3) assisting insulin action by interaction with lipoproteins, enzymes, and cells.

In one or more embodiments, the dextran acts as an active response-inhibiting agent. In one embodiment, a dextran reservoir is provided, wherein the dextran is pre-filled with insulin as a reservoir and re-fill bottle. In another embodiment, an in-line dextran depot is provided for continuous dextran delivery, which can be attached to specific components (e.g. reservoir or each portion of infusion set). The depot may be attached to various section of the fluid path of the pump/infusion set in various forms. The attachment may be filter, plug, sponge, etc. Difference release profiles may be used with the dextran depot. FIGS. 16B-D provide various examples of depots.

Figure 22:
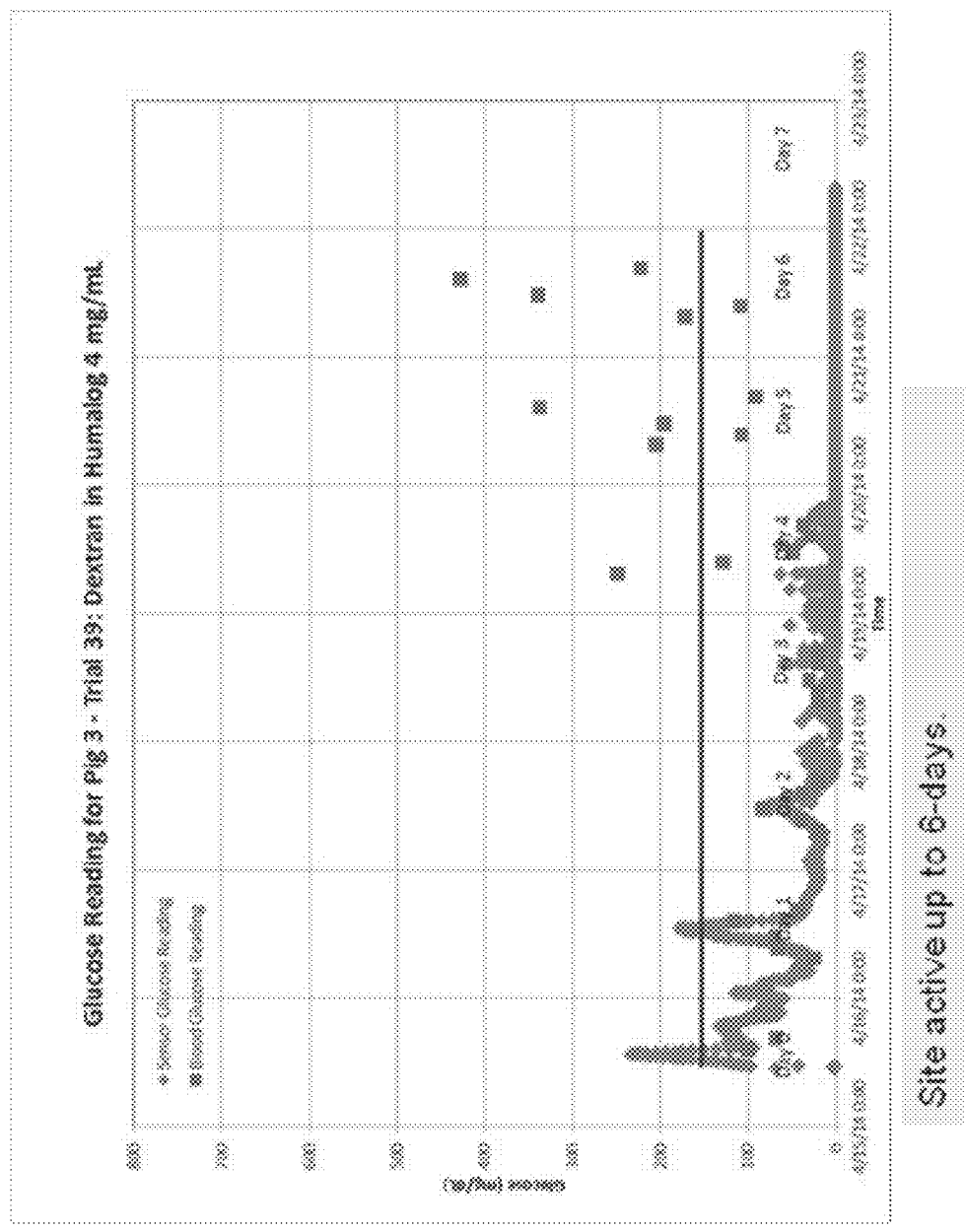
FIG. 22 is a graph of blood glucose (BG) vs. time for Sof-Set™ with dextran dosed insulin, which shows that the infusion site was active up to 6 days.

Illustrative experiments demonstrate the efficacy of dextran in extending infusion set wear in a diabetic porcine model. FIG. 22 is a graph of blood glucose (BG) vs. time for Sof-Set™ with dextran dosed insulin, which shows that the infusion site is active up to 6 days.

Example 10: Usage of Rapamycin for an Extended Wear Infusion Set

A rapamycin eluting coating for an insertion cannula or needle is developed to extend infusion set wear. The coating may also be used to coat the inner layer of infusion set to extend infusion set wear. The coating extends infusion set wear by 1) mitigating tissue immune-response to insertion cannula/needle and infused insulin; 2) reducing inflammation; 3) reducing/inhibiting scar tissue formation; and/or 4) preventing immune-response induced occlusion at the infusion cannula tip. With extended wear, the site of infusion is available for a longer period of time for insulin absorption to lower a blood glucose level.

In one or more embodiments, a coating on cannula/needle, typically of a polymer, holds and elutes (releases) the drug into the subcutaneous tissue by contact transfer. Coatings (likely durable) may be spray-coated or dip-coated. There can be one to three or more layers in the coating. In one example, there is a base layer for adhesion, a main layer for holding the drug, and a top coat to slow down the release of the drug and extend its effect. In other embodiments, the drug is loaded on the inner side of the infusion set tube.

Figure 23:
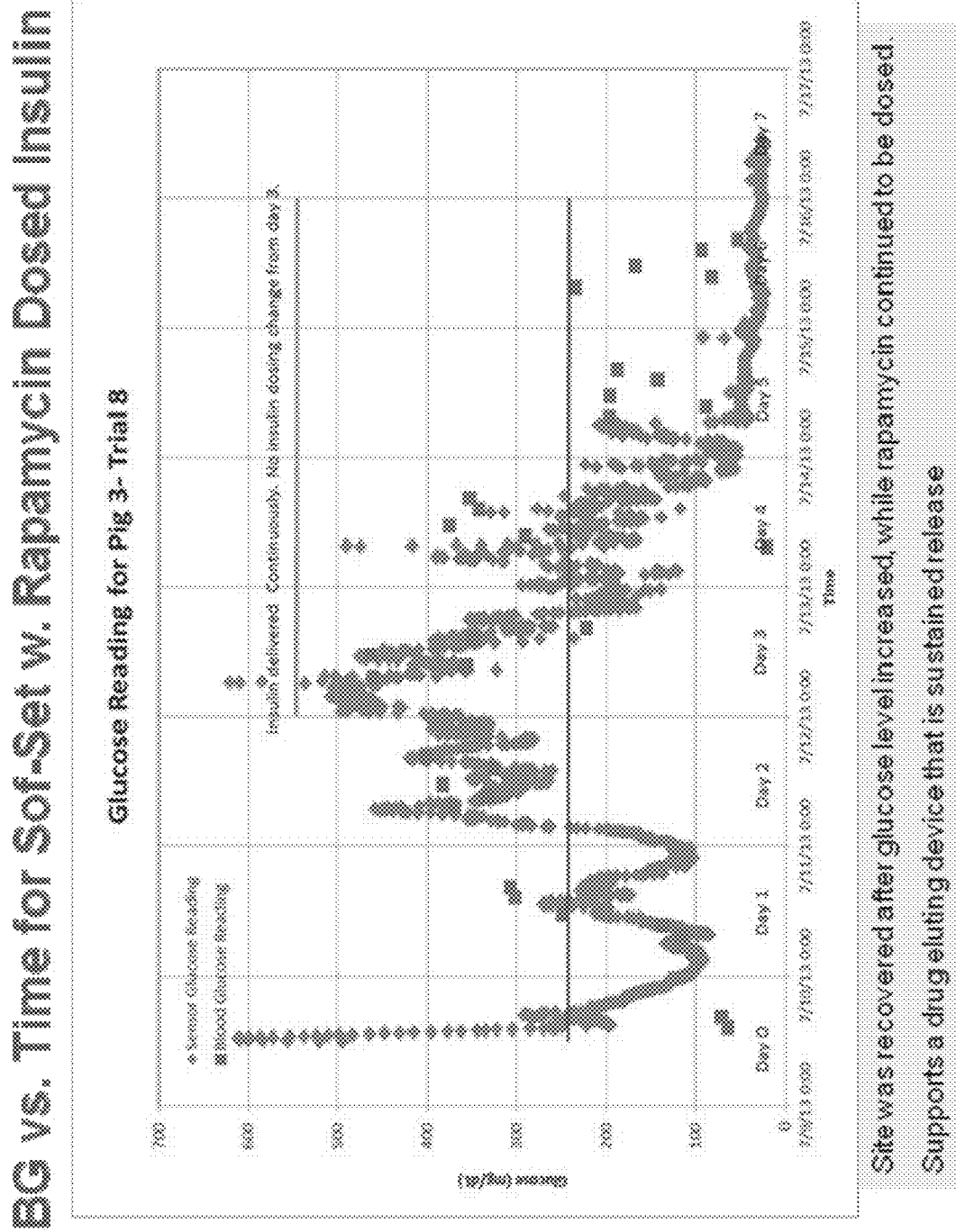
FIG. 23 is a graph of blood glucose (BG) vs. time for Sof-Set™ with rapamycin dosed insulin. The infusion site was recovered after glucose level increased, while rapamycin continued to be dosed. This supports a drug eluting device that is sustained release.
Figure 24:
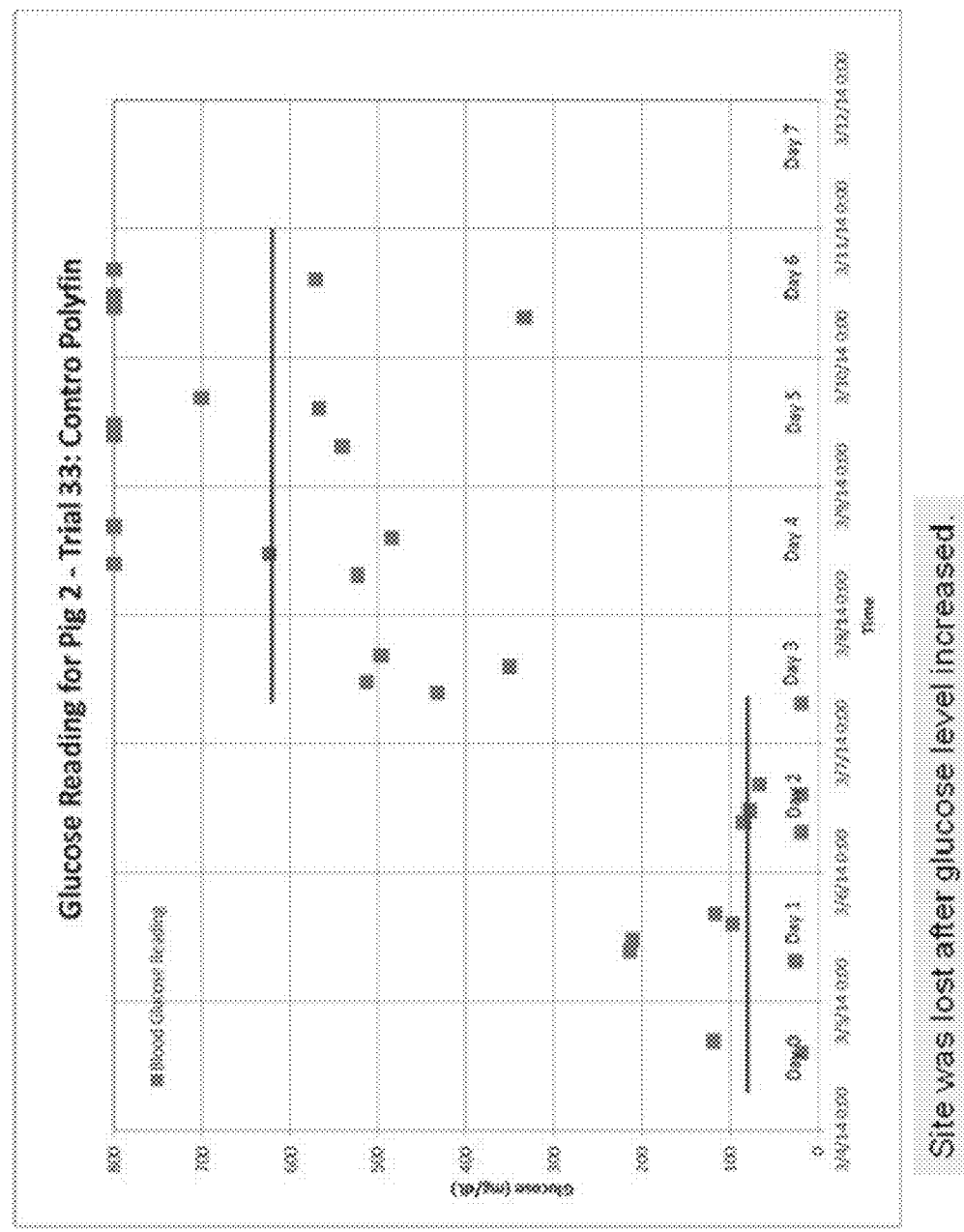
FIG. 24 is a graph of the glucose monitoring results for control Polyfin™ (IM2) showing site-loss at around 2.5 days.
Figure 25:
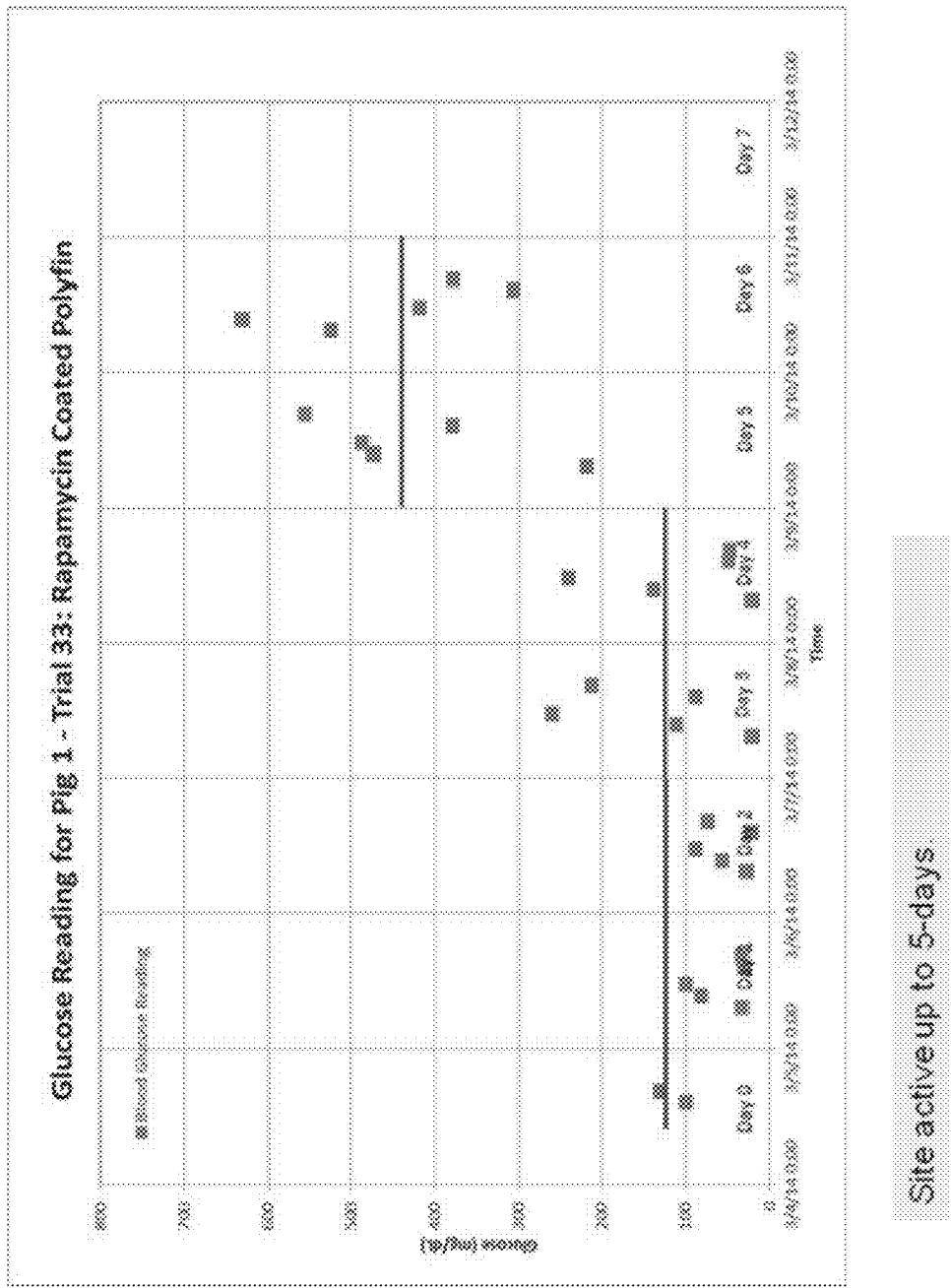
FIG. 25 is a graph of the glucose monitoring results for rapamycin coated Polyfin™ (IM1) showing site-loss at day 5.
Figure 26:
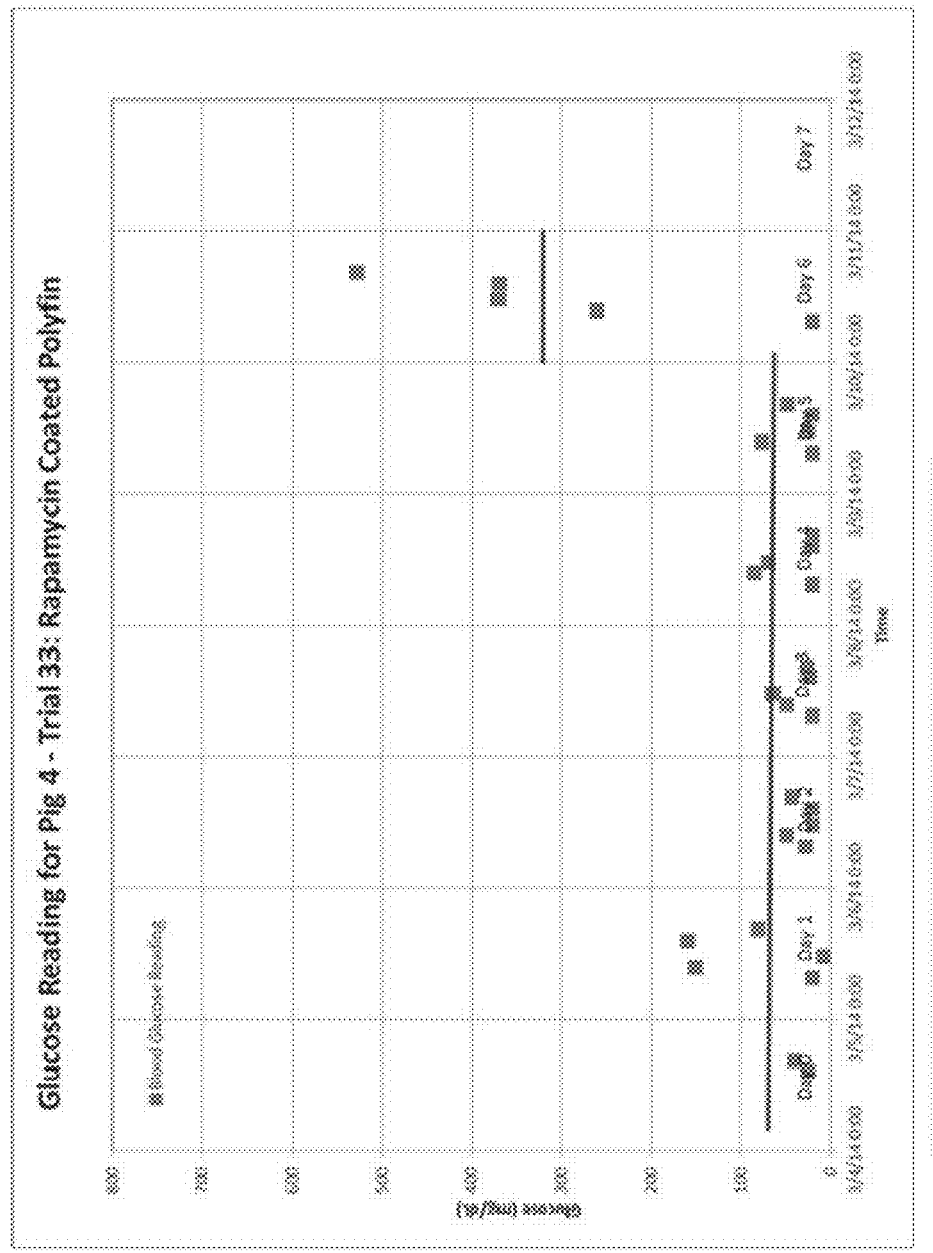
FIG. 26 is a graph of the glucose monitoring results for rapamycin coated Polyfin™ (IM4) showing site-loss at day 6.

Illustrative experiments, with rapamycin loading ranging from 0.5-10 µg/cannula, have demonstrated the efficacy in extending infusion set wear in diabetic porcine model. In one embodiment, a Sof-Set™/Polymeric Cannula Infusion Set (teflon cannula) infusion set is uniformly coated with rapamycin with a dose of 2-5 µg/cannula. An example test with a diabetic porcine model found that rapamycin spiked in insulin with a Sof-Set™ infusion set resulted in no site loss for more than 6 days, with rapamycin dosing in the pig at around 0.6 µg/day. Higher rapamycin dosing (greater than 1.5 µg/day) indicated local toxicity. FIG. 23 is a graph of blood glucose (BG) vs. time for Sof-Set™ with rapamycin dosed insulin. The infusion site was recovered after the glucose level increased while rapamycin continued to be dosed. This supports a drug eluting device that is sustained release. A rapamycin-coated Polyfin™ infusion set (stainless steel cannula) (at ~1 µg/cannula) demonstrated the efficacy in extending infusion set wear in diabetic porcine model from 2-3 days (control, FIG. 24) to 5-6 days (coated, FIGS. 25 and 26). FIG. 24 shows that the infusion site was lost after glucose levels increased. FIGS. 25 and 26 show that the infusion site was active up to 5 days and 6 days, respectively. Coating that matches dosing used in insulin-rapamycin liquid formulation, improves extended wear beyond 6 days.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching and the scope of the appended claims should be construed as broadly as the prior art will permit.

The invention claimed is:

1. A method for modulating the delivery of insulin from a subcutaneous reservoir in a diabetic patient into blood of the patient, the method comprising infusing the insulin into the subcutaneous reservoir of the patient at an infusion site using a system comprising:
    a container comprising an insulin solution;
    a cannula adapted for subcutaneous insertion into the subcutaneous reservoir of the diabetic patient;
    a fluid conduit in operable contact with the container and the cannula and adapted to deliver the insulin solution from the container to the subcutaneous reservoir;
    a depot in operable contact with the fluid conduit and comprising a polyvinyl alcohol foam material disposed therein, wherein the polyvinyl alcohol foam material:
        comprises a plurality of interconnected hollow voids;
        comprises pores having sizes between 0.1 and 5 mm;
        comprises a porosity between 50 and 95%;
        comprises a dry density of between 0.1 and 1.5 grams per cubic inch;
        absorbs an aqueous solution so as to saturate the foam material by at least 95% in a time between 0.1 and 1 minutes;
        traps insulin aggregates that form in insulin solutions; and
        traps air bubbles that form in insulin solutions; and
    allowing insulin to flow from the container through the fluid conduit, depot and cannula and into the subcutaneous reservoir so that insulin is infused into the subcutaneous reservoir of the patient.

2. The method of claim 1, further comprising a site-loss mitigating agent disposed in the depot, wherein:
    the site-loss mitigating agent is adapted to contact the insulin solution as the insulin solution flows through the depot; and
    the site-loss mitigating agent inhibits at least one of: coagulation at the site of infusion, inflammation at the site of infusion, and encapsulation of the cannula at the site of infusion.

3. The method of claim 2, wherein the site-loss mitigating agent comprises heparin in an amount sufficient to inhibit inflammation at the infusion site for at least 4, 5, 6, 7, 8 or 9 days.

4. The method of claim 1, wherein the system further comprises a membrane in operable contact with the fluid conduit, wherein:
    the membrane is formed from a polymeric material having pores that are between 0.1 µm to 10 µm in diameter;
    the membrane exhibits an ability to filter/trap particulates in insulin solutions; and
    the membrane exhibits an ability to filter/trap insulin aggregates that form in insulin solutions.

5. The method of claim 4, wherein the membrane comprises:
    an acrylic copolymer membrane with pore sizes of about 0.1 to 10 µm;
    a polyethersulfone membrane with pore sizes of about 0.1 to 10 µm;
    a mixed cellulose esters membrane with pore sizes of about 0.1 to 10 µm;
    a cellulose acetate membrane with pore sizes of about 0.1 to 10 µm;
    a cellulose nitrate membrane with pore sizes of about 0.1 to 10 µm;
    a nylon membrane with pore sizes of about 0.21 to 10 µm;
    a hydrophilic polytetrafluoroethylene (PTFE) membrane with pore sizes of about 0.1 to 10 µm; or
    a polycarbonate membrane with pore sizes of about 0.1 to 10 µm.

6. The method of claim 1, wherein the system further comprises:
- a cap for coupling the container to the fluid conduit;
- a housing engagement member comprising a detent or a thread projecting outward from a cylindrical external surface of the cap and adapted to engage an engagement member disposed in a housing recess within an insulin infusion device, wherein the cap connects with the container and both the cap and the container at least partially fit inside the housing recess of the infusion device and are insertable and removable from the housing recess within the infusion device upon rotation of the cap;
- a conduit cavity disposed in the cap and adapted to secure the fluid conduit to the cap;
- a first tab disposed on the cap so as to provide a first surface for a user to grip and twist the cap to engage the cap with the infusion device upon rotation of the cap, wherein the first tab projects outward from the cap such that the first surface of the first tab is disposed in an orientation perpendicular to a plane defined by the circumference of the cap; and
- a vent disposed in the cap that permits the passage of air and simultaneously inhibits the passage of fluids so as to permit fluid resistant venting of air through the vent and equalization of pressure inside the infusion device to atmospheric pressure outside the infusion device.

7. The method of claim 1, wherein the system further comprises at least one of:
- (a) medical tubing preventing loss of ingredients and protecting formulation integrity during insulin infusion;
- (b) medical tubing formed from a plurality of layers of polymeric materials, optionally wherein a polymeric material is formed with internal ribs designed to inhibit kinking;
- (c) medical tubing formed to include an area of color or opacity that facilitates visualization of fluid flow through the tubing;
- (d) medical tubing comprising a connector at an end of the tubing, wherein: the connector comprises:
  - (i) a matrix impregnated with heparin; or
  - (ii) a magnetic washer;
- (e) medical tubing comprising a tubing connector coupled to the heparin depot so at to allow a first tubing conduit component to connect to a second tubing conduit component; wherein the depot comprises a matrix impregnated with heparin;
- (f) an infusion hub adapted to be affixed to the skin of a patient and infuse insulin, wherein the infusion hub comprises a matrix impregnated with heparin;
- (g) an adhesive transdermal patch designed to affix an infusion catheter to a site of infusion, wherein the transdermal patch is formed from a plurality of layered materials and a movable liner, and the adhesive transdermal patch comprises a matrix impregnated with heparin; and
- (h) a reservoir connector adapted to operably connect infusion tubing to the container, wherein the reservoir connector comprises a matrix impregnated with heparin, and a luer connector.

8. The method of claim 1, wherein a protease inhibitor is not included with the insulin.

9. The method of claim 1, wherein the insulin is infused over a period of time greater than 10, 15, 30, 60 or more minutes.

10. The method of claim 1, wherein the depot comprises a site-loss mitigating agent.

11. The method of claim 10, wherein the site-loss mitigating agent inhibits inflammation at the single site of infusion for at least 4, 5, 6, 7, 8 or 9 days.

* * * * *